United States Patent
Dewey et al.

(10) Patent No.: US 12,029,654 B2
(45) Date of Patent: Jul. 9, 2024

(54) IN-SITU ADDITIVE MANUFACTURED MOTION-SPARING IMPLANTS

(71) Applicant: Warsaw Orthopedic, Inc., Warsaw, IN (US)

(72) Inventors: Jonathan M. Dewey, Memphis, TN (US); Michael L. Sutton, Coldwater, MS (US); Jerald L. Redmond, Germantown, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 1001 days.

(21) Appl. No.: 16/992,432

(22) Filed: Aug. 13, 2020

(65) Prior Publication Data

US 2021/0177603 A1 Jun. 17, 2021

Related U.S. Application Data

(63) Continuation-in-part of application No. 16/716,697, filed on Dec. 17, 2019, now Pat. No. 11,523,916, and (Continued)

(51) Int. Cl.
*A61F 2/30* (2006.01)
*A61F 2/44* (2006.01)
*A61F 2/46* (2006.01)

(52) U.S. Cl.
CPC .......... *A61F 2/30942* (2013.01); *A61F 2/442* (2013.01); *A61F 2/4611* (2013.01); (Continued)

(58) Field of Classification Search
CPC .. A61F 2/44; A61F 2/46; A61F 2/4611; A61F 2/4455; A61F 2/30; A61F 2/3094; A61B 17/70; A61B 17/7062; A61B 34/20
See application file for complete search history.

(56) References Cited

U.S. PATENT DOCUMENTS 7,051,654 B2 5/2006 Boland et al.
7,875,324 B2 1/2011 Barron et al.
(Continued)

FOREIGN PATENT DOCUMENTS

CN 204092271 U 1/2015
CN 104688388 A 6/2015
(Continued)

OTHER PUBLICATIONS

European Search Report in Application No. 21189618.8 dated Jan. 14, 2022.
(Continued)

*Primary Examiner* — Christopher J Beccia
(74) *Attorney, Agent, or Firm* — FOX ROTHSCHILD LLP

(57) ABSTRACT

An additive-manufacturing system for printing spinal implants in-situ, within a patient, is disclosed. The system may include a robotic subsystem having scanning and imaging equipment and an armature including at least one dispensing nozzle and a controller apparatus having a processor and a non-transitory computer-readable medium. The controller may control the scanning and imaging equipment to determine a target alignment of a patients spine, develop an in-situ-printing plan including an in-situ material selection plan based on the target alignment of the patients spine, an interbody access space, and a disc space between adjacent vertebra of the patients spine, and execute the in-situ-printing plan. The controller may further control the armature to dispense at least one material chosen from a rigid material and a pliable material to form at least one motion-sparing implant.

13 Claims, 49 Drawing Sheets

Related U.S. Application Data a continuation-in-part of application No. 16/716,771, filed on Dec. 17, 2019, now Pat. No. 11,523,909, and a continuation-in-part of application No. 16/907,341, filed on Jun. 22, 2020, and a continuation-in-part of application No. 16/986,869, filed on Aug. 6, 2020.

(52) U.S. Cl.
CPC ............ *A61F 2002/30065* (2013.01); *A61F 2002/30952* (2013.01); *A61F 2002/30971* (2013.01); *A61F 2002/30985* (2013.01)

(56) References Cited

U.S. PATENT DOCUMENTS

| | | | |
|---|---|---|---|
| 7,909,876 | B2 | 3/2011 | Dooris et al. |
| 9,020,788 | B2 | 4/2015 | Lang et al. |
| 9,626,989 | B1 | 4/2017 | Buch et al. |
| 10,442,182 | B2 | 10/2019 | Varanasi et al. |
| 10,492,875 | B2 | 12/2019 | Janik et al. |
| 10,736,698 | B2 | 8/2020 | Bohl |
| 11,033,336 | B2 | 6/2021 | Bohl |
| 11,523,916 | B2 | 12/2022 | Dewey et al. |
| 2003/0078667 | A1 | 4/2003 | Manasas et al. |
| 2006/0276925 | A1 | 12/2006 | Lin et al. |
| 2008/0109081 | A1 | 5/2008 | Bao et al. |
| 2014/0207235 | A1 | 7/2014 | Drapeau |
| 2016/0129155 | A1 | 5/2016 | Lin et al. |
| 2016/0288414 | A1 | 10/2016 | Ozbolat et al. |
| 2016/0374770 | A1* | 12/2016 | Janik ............... A61B 34/70 604/500 |
| 2017/0238984 | A1 | 8/2017 | Kleiner |
| 2018/0092755 | A1 | 4/2018 | Lechmann et al. |
| 2018/0243094 | A1 | 8/2018 | Jones et al. |
| 2018/0368992 | A1 | 12/2018 | Zink et al. |
| 2019/0008655 | A1 | 1/2019 | Body |
| 2019/0029842 | A1* | 1/2019 | Xiao ............... A61L 27/56 |
| 2019/0099515 | A1 | 4/2019 | Bagga et al. |
| 2021/0007778 | A1 | 1/2021 | Shoham |
| 2021/0093457 | A1 | 4/2021 | Hodrinsky et al. |

FOREIGN PATENT DOCUMENTS

| | | |
|---|---|---|
| CN | 105287059 A | 2/2016 |
| CN | 105751510 A | 7/2016 |
| CN | 106361431 A | 2/2017 |
| CN | 206491869 U | 9/2017 |
| DE | 102015222117 A1 | 5/2017 |
| EP | 3045150 A1 | 7/2016 |
| EP | 3603580 A1 | 2/2020 |
| EP | 3666231 A1 | 6/2020 |
| EP | 3954318 A1 | 2/2022 |
| WO | 2015066705 A1 | 5/2015 |
| WO | 2015131234 A1 | 9/2015 |
| WO | 2016/210081 A1 | 12/2016 |
| WO | 2017/080646 A1 | 5/2017 |
| WO | 2018185755 A1 | 10/2018 |
| WO | 2018193316 A2 | 10/2018 |
| WO | 2020069012 A2 | 4/2020 |
| WO | 2021126702 A1 | 6/2021 |

OTHER PUBLICATIONS

U.S. Appl. No. 16/716,697, filed Dec. 17, 2019, In Situ Printed Implants.
U.S. Appl. No. 16/716,771, filed Dec. 17, 2019, In Situ Printed Implants.
U.S. Appl. No. 16/907,341, filed Jun. 22, 2020, In Situ Printed Channeled Implants.
U.S. Appl. No. 16/986,869, filed Aug. 6, 2020, In-Situ Additive Manufactured Motion-Sparing Implants.
Ashammakhi Nureddin et al: "In situ three-dimensional printing for reparative and regenerative therapy", Biomed Microdevices, Kluwer Dordrecht, NL, vol. 21, No. 2, Apr. 6, 2019, pp. 1-6.
Manyi Wang et al: "The trend towards in vivo bioprinting", International Journal of Bioprinting, Jul. 2, 2015.
International Search Report for PCT/US2021/037882 dated Oct. 19, 2021.
Xie Sheng et al., "Turbulent Air Flow Field and Fiber Whipping Motion in the Melt Blowing Process: Experimental Study", Industrial & Engineering Chemistry Research, vol. 51 , No. 14, Apr. 11, 2012 (Apr. 11, 2012), pp. 5346-5352, XP055896821, ISSN: 0888-5885, DOI: 10.1021/ie202938b.
European Search Report in Application No. 21196870.6 dated Mar. 15, 2022.
European Search Report in Application No. 21191309.0 dated Jan. 18, 2022.
Cui et al. "Direct Human Cartilage Repair Using Three-Dimensional Bioprinting Technology," Tissue Engineering: Part A, 2012, vol. 18, No. 11 & 12, pp. 1304-1312.
Di Bella et al. "In situ handheld three-dimensional bioprinting for cartilage regeneration," Journal of Tissue Engineering for Regenerative Medicine, Mar. 2018, vol. 12, No. 3, pp. 611-621.
Hong et al. "3D bioprinting and its in vivo applications," Journal of Biomedical Materials Research Part B: Applied Biomaterials, Jan. 2018, vol. 106, No. 1, pp. 444-459.
O'Connell et al. "Development of the Biopen: a handheld device for surgical printing of adipose stem cells at a chondral wound site," Biofabrication, Mar. 2016, vol. 8, No. 1, 015019.
Rengier et al. "3D printing based on imaging data: review of medical applications," International Journal of Computer Assisted Radiology Surgery, Jul. 2010, vol. 5, No. 4, pp. 335-341.
Wang et al. "The trend towards in vivo bioprinting," International Journal of Bioprinting, 2015, vol. 1, No. 1, pp. 15-26.

\* cited by examiner

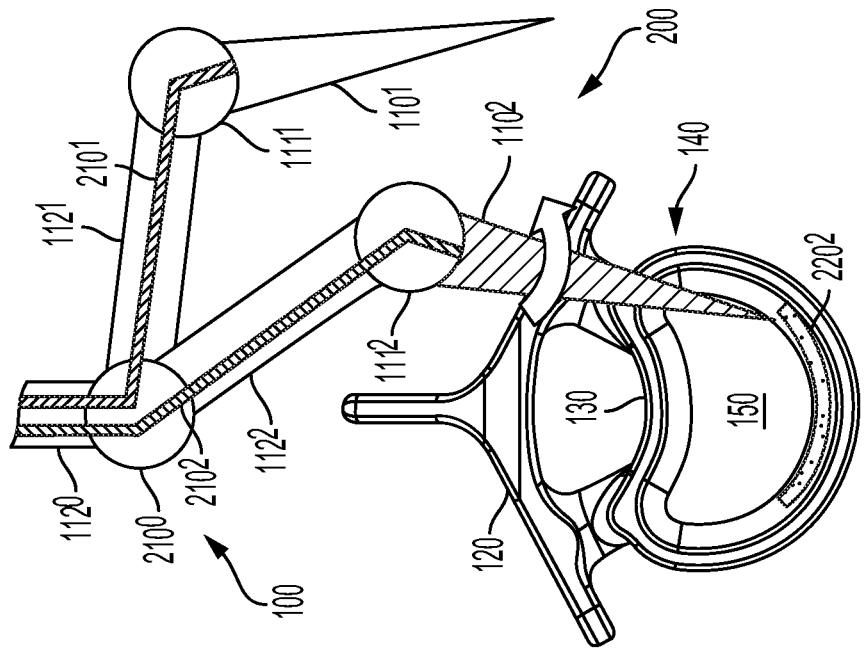
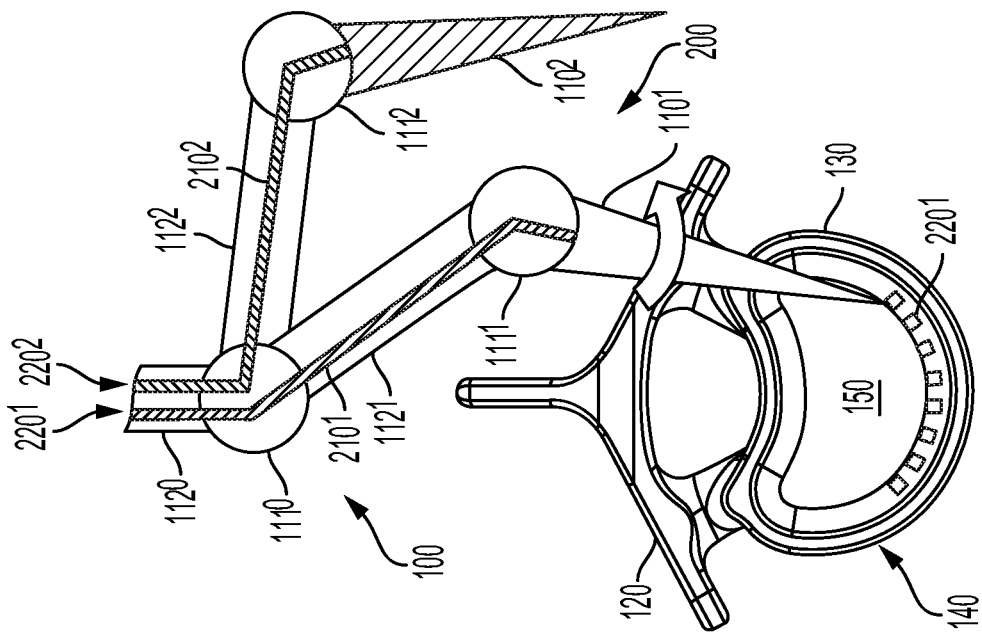

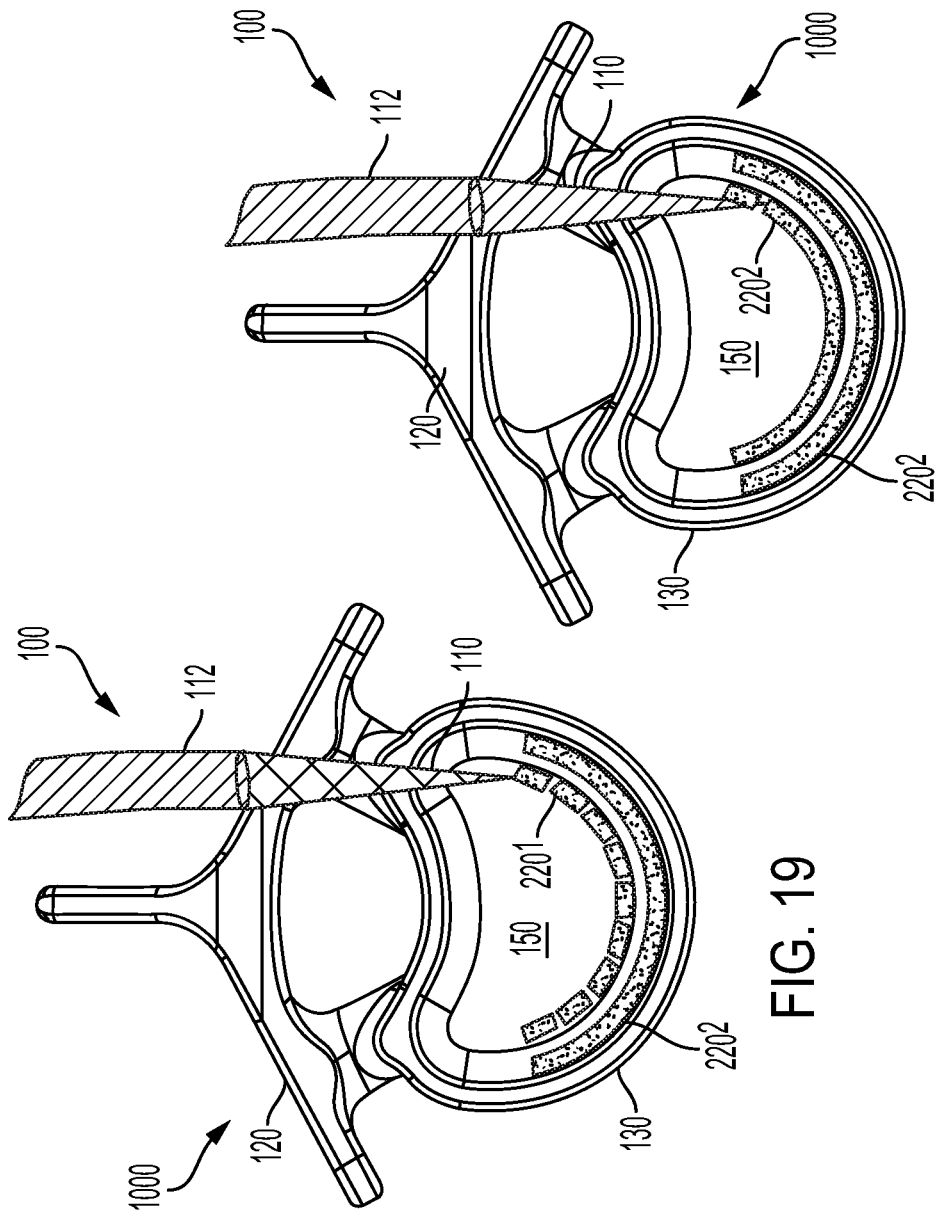

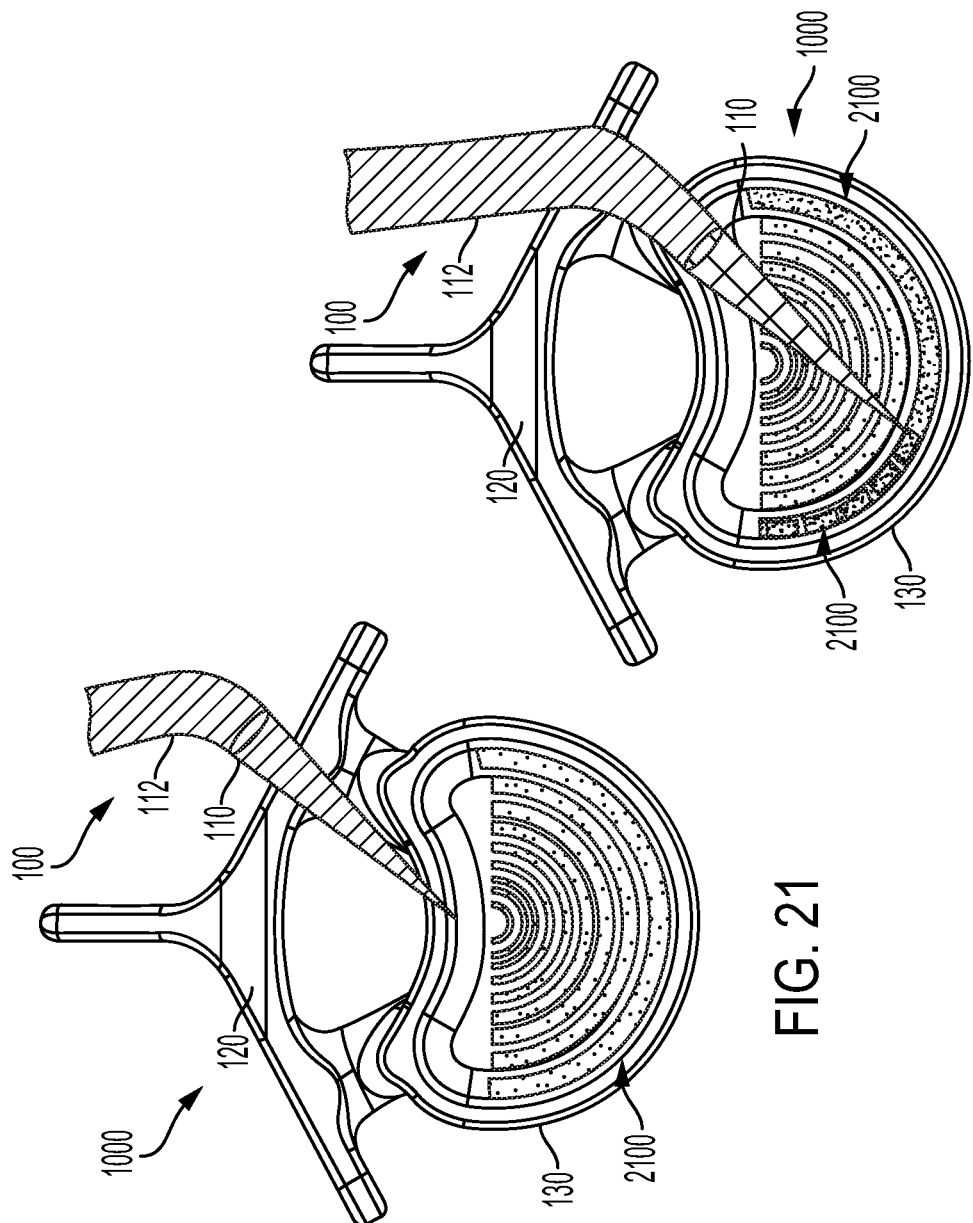

IN-SITU ADDITIVE MANUFACTURED MOTION-SPARING IMPLANTS

CROSS-REFERENCE TO RELATED APPLICATIONS

This application is a continuation in part of U.S. application Ser. No. 16/716,697, filed Dec. 17, 2019, and U.S. application Ser. No. 16/716,771, filed Dec. 17, 2019, U.S. application Ser. No. 16/907,341, filed Jun. 22, 2020, and U.S. application Ser. No. 16/986,869 filed Aug. 6, 2020. The contents of each are herein incorporated in their entireties.

FIELD

The present technology is related generally to additive-manufacturing systems and processes for forming patient implants in-situ that are motion-sparing, or motion-preserving.

BACKGROUND

Additive manufacturing processes have been used increasingly to make a wide variety of parts, including medical implants. An example implant is a spinal interbody, or cage.

Advances in additive-manufacturing technology and material science have expanded the types and configurations of parts that can be printed, including parts having internal or otherwise intricate features that were not possible before.

Conventional additively-manufactured implants may have various shortcomings.

Some of the shortcomings may relate to the fact that they are typically pre-manufactured in mass quantities. They are thus not customized, specific to particular patient anatomy, for instance. They are, rather, one-size/shape fits many.

Some product lines offer multiple size options. Even so, product geometry may still be somewhat generic.

As another shortcoming, conventional parts can be difficult or impossible to implant because of access issues. There may be patient tissue partially blocking the implant from being delivered to the target implant position. Other access related issues may occur from collapsed or partially collapsed adjacent vertebrae that block access to the area between the adjacent vertebrae.

As yet another shortcoming, there are undesirable costs related to off-site manufacture. These include cost of packaging, shipping, tracking, storage, and retrieving and preparing for implantation.

In some medical procedures, multiple parts may be implanted. In some of these cases, the parts are connected prior to or during surgery to form a construct. In some conventional spinal surgeries, for instance, a construct of pre-manufactured components is assembled to fix adjacent patient vertebrae together, to limit relative movement between the vertebrae. Fixing relative position between select vertebrae alleviates or obviates implications such as nerve impingement or problematic intervertebral contact. Such implications can result from trauma or the intervertebral disc being compromised. The fixation can also cause adjacent vertebrae to fuse, or grow, together.

In addition to the mentioned potential shortcomings of pre-made implants, shortcomings specific to implant assemblies may include additional labor associated with fitting and connecting components manually.

And no matter the type of conventional implant, there may be a challenge ensuring precise positioning in the patient.

An additional challenge with conventional spinal implants formed of rigid materials is that they may reduce the range of motion of a patient's spine and/or reduce the natural shock absorption between corresponding vertebrae of a patient. For example, conventional spinal implants formed of hard metallic materials may not allow for sufficient flexural properties to provide a desirable target range of motion. Additionally, conventional spinal implants, may eliminate and/or reduce the viability of shock absorption between the relevant vertebrae. For example, still, conventional spinal implants utilizing bone screws and/or bone growth promoting material optimized to fuse adjacent vertebrae of a patient may reduce the range of motion of the relevant vertebrae as well as eliminate and/or reduce the viability of shock absorption between the relevant vertebrae.

Solutions to the above challenges are desired for spinal surgeries, other medical procedures calling for an implant, and other industries involving some sort of device, whether or not referred to as an implant, including outside of the medical industry.

SUMMARY

The systems and process of the techniques of this disclosure relate generally to additive-manufacturing systems and processes for forming parts or devices in-situ, such as in a patient during surgery.

In one aspect, the present disclosure provides a method for printing an in-situ printed motion-sparing implant. The method may include positioning, in a first positioning step, a dispensing component within or adjacent to an interbody access space that provides access to an intervertebral disc space defined by a first vertebra and a second vertebra of a patient, and printing, in a first printing step, a rigid material within or adjacent to the interbody access space. Additionally, the method may include printing, in a second printing step, a pliable material within or adjacent to the interbody access space. In some embodiments, the rigid material is in contact with the pliable material.

In another aspect, the present disclosure provides for a method that includes providing an additive-manufacturing system including a robotic subsystem and a controller apparatus having a processor and a non-transitory computer-readable medium storing in-situ-printing instructions, and executing the in-situ-printing instructions, thereby controlling the robotic subsystem to perform the printing steps.

In another aspect, the present disclosure provides for an additive-manufacturing system that further includes a provisioning component affecting flow of printing material to or through the dispensing component, and the controller apparatus, in the printing step, controls the provisioning component based on dispensing-component movement data to control a rate at which the printing material is dispensed.

In another aspect, the present disclosure provides that each printing step includes depositing a first layer of a first type of printing material and depositing a second layer of a second type of printing material on the first layer.

In another aspect, the present disclosure provides for printing, in a third printing step, another rigid material within or adjacent to the interbody access space, and in some embodiments the pliable material of the second printing step is surrounded by the rigid material of the first and third printing steps.

In another aspect, the present disclosure provides for a motion-sparing spinal implant formed in-situ, within a patient. In some embodiments, a first endcap formed of a rigid material and has a size corresponding to a first vertebral body and a second endcap formed of a rigid material and having a size corresponding to a second vertebral body. Additionally, a pliable material configured to fill an interior space between the first and second endcaps, the pliable material being dispensed by the dispensing component and cured in-situ within the disc space of a patient.

In another aspect, the present disclosure provides that in some embodiments, the first endcap and second endcap are formed of rigid material dispensed by the dispensing component.

In another aspect, the present disclosure provides that in some embodiments the first endcap and second endcap are provided from stock material.

In another aspect, the present disclosure provides that the first endcap and second endcap are coupled to the pliable material.

In another aspect, the present disclosure provides that in some embodiments, first endcap and second endcap are configured to confine the pliable material therebetween.

In another aspect, the present disclosure provides that in some embodiments the first endcap and second endcap are coupled together by a tether configured to define a height of the interior space between the first and second endcaps.

In another aspect, the present disclosure provides that the pliable material is an expanding material configured to expand the interior space between the first and second endplates thereby placing the tether under tension.

In another aspect, the present disclosure provides that in some embodiments, the first endcap and second endcap are coupled together by at least one first tether disposed along a first radial side and at least one second tether disposed along a second radial side opposite the first radial side, and the at least one first tether is longer than the at least one second tether.

In another aspect, the present disclosure provides that the pliable material is an expanding material configured to expand the interior space between the first and second endplates thereby placing the at least one first tether and the at least one second tether under tension and thereby inclining the first endplate with respect to the second endplate.

In another aspect, the present disclosure provides for an additive-manufacturing system for printing spinal implants in-situ, within a patient. The system may include a robotic subsystem having scanning and imaging equipment configured to scan a patient's anatomy, and an armature including at least one dispensing nozzle configured to selectively dispense at least one rigid material and at least one pliable material. The system may further include a controller apparatus having a processor and a non-transitory computer-readable medium storing computer-executable instructions configured to, when executed by the processor, cause the controller to: control the scanning and imaging equipment to determine a target alignment of a patients spine, develop an in-situ-printing plan including an in-situ material selection plan based on the target alignment of the patients spine, an interbody access space, and a disc space between adjacent vertebra of the patients spine, and execute the in-situ-printing plan. In executing the in situ printing plan the controller may control the armature to dispense the at least one material chosen from the at least one rigid material and the at least one pliable material to form at least one motion-sparing implant.

In another aspect, the present disclosure provides that in some embodiments a provisioning component for affecting a rate of flow of printing material and a type of printing material through the dispensing component may be provided. In some embodiments, the controller is further configured to control the provisioning component on the basis of the in-situ-printing plan and the in-situ material selection plan.

In another aspect, the present disclosure provides that the controller is further configured to control forming the at least one motion-sparing implant from a plurality of different printing materials chosen from the at least one rigid material and the at least one pliable material.

In another aspect, the present disclosure provides for a mixing component configured to selectively mix materials chosen from the at least one rigid material, the at least one pliable material, and at least one adhesive material.

In another aspect, the present disclosure provides that the computer-executable instructions are further configured to, when executed by the processor, cause the controller to form at least one motion-sparing implant. The motion-sparing implant may include a first endcap formed of a rigid material and having a size corresponding to a first vertebral body and a second endcap formed of a rigid material and having a size corresponding to a second vertebral body, and a pliable material configured to fill an interior space between the first and second endcaps, the pliable material being dispensed by the dispensing component and cured in-situ within the disc space of a patient.

In another aspect, the present disclosure provides that the computer-executable instructions are further configured to, when executed by the processor, cause the controller to form a lattice structure having a repeating pattern of cells from the at least one rigid material and fill the cells with the at least one pliable material.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 2 is an axial view of a multi-dispensing arrangement, in a first, substrate-dispensing mode, of the additive-manufacturing system, positioned adjacent the patient vertebra according to a first exemplary embodiment of the present disclosure.

FIG. 3 is an axial view of another multi-dispensing arrangement, in a second, catalyst-dispensing mode, positioned adjacent the patient vertebra according to the first exemplary embodiment.

FIG. 19 shows the dispensing component completing deposit of the subsequent row of substrate material at the in-situ position of the patient according to the first general embodiment of the present technology.

FIG. 20 shows the dispensing component depositing catalyst over the subsequent-row substrate material at the in-situ position of the patient according to the first general embodiment of the present technology.

FIG. 21 shows an example first layer of the additive in-situ implant completed according to the first general embodiment of the present technology.

FIG. 22 shows the dispensing component beginning formation of a subsequent layer of substrate material over the first layer at the in-situ position of the patient according to the first general embodiment of the present technology.

FIG. 68B is a perspective view of an in-situ printed motion-sparing implant including a first endplate and a second endplate surrounded by a pliable material.

DETAILED DESCRIPTION

Figure 1:
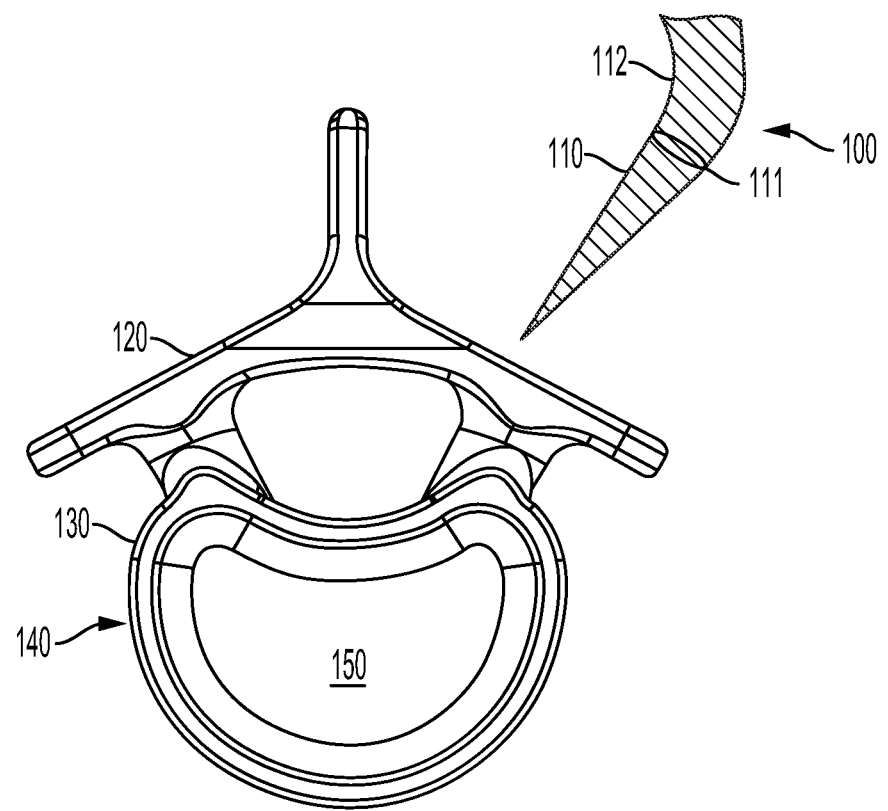
FIG. 1 is an axial view a dispensing component of a surgical additive-manufacturing system positioned adjacent a patient vertebra according to a general embodiment of the present disclosure.

While the present technology is described primarily in the context of spinal implants, the technology is not limited to use with spinal surgery, or even to use for medical procedures. The technology can be used for making devices, whether referred to as implants, for other industries, such as construction or automotive, for instance.

Descriptions provided herein regarding medical procedures can, thus, be analogized to the other industries. The descriptions are thus to be understood to include inherently disclosure of such other analogous implementations. Descriptions herein of printing a unique component between or adjacent two vertebrae, in ways that cannot be done with a conventional fully pre-made spinal implant—due to access, fit, or geometry challenges, for instance—thus include thereby disclosure of analogous processes for printing non-medical implants at least partially in-situ, for overcoming the similar access, fit, or geometry challenges. The technology can be used readily to connect more than two vertebra (a single-level procedure), in a multi-level procedure connecting any number of vertebra.

As another example of analogous interpretation, of disclosure from spinal procedures to other medical procedures and other-industry procedures, elimination of fiscal or labor costs described in connection with spinal- or medical-industry implementation relates to fiscal or labor savings achievable in any other industry in which the technology can be used.

Spinal implants are often used to fix together two or more adjacent vertebrae. Fixing relative position between select vertebrae alleviates or obviates implications such as nerve impingement or problematic intervertebral contact. Such implications can result from trauma or the intervertebral disc having become compromised. Though fusing vertebrae together limits patient flexibility, fixing relative position between select vertebrae promotes continued alleviation of said implications.

Benefits from using the technology include the ability to custom-make implants, such as spinal implants, that are particular to a subject-patient anatomy. Benefits also include the ability to make patient-specific implants having geometries that are otherwise impossible or prohibitive to make.

Advantageous geometries from growing implants in-situ according to the present technology include those that can realize a specific desired final positioning in the patient. These advantages include advantages stemming from obviating challenges in maneuvering a complete pre-manufactured implant into place in the patient.

The advantages include allowing or improving issues relating to access, fit, and part placement, including orientation. Regarding access, for instance, the present technology in many implementations allows printing of implants in spaces having clearance challenges making implantation of conventional pre-made implants difficult, prohibitive, or impossible. Fit advantages include the ability to achieve highly accurate positioning and orientation adjacent the patient, such as between or adjacent patient vertebrae.

Benefits from the present technology also include obviating or reducing any of various cost factors, such as cost of packaging, shipping, tracking, storage, and retrieving and preparing for implantation.

The present technology can also eliminate some or all manual steps involved with conventional implanting, depending on the implementation of the present disclosure employed.

As referenced, benefits from the present technology can also include any of those applicable in other industries. These can include any of those referenced herein for spinal or medical implants, such as the ability to grow or form custom-fit implants, and various cost savings (obviating part-shipping, storage, and tracking, for instance).

Another common benefit between medical and other-industry applications can include access, or the ability to deliver parts to a position or orientation that would be difficult or impossible to get the parts to otherwise.

An ability to grow or form implants in-situ also gives an ability to grow or form the implants to have more than one material, selected and printed in portions of the implant and with geometries determined best suited to perform in the patient as desired. For example, in-situ grown or formed implants may have varying mechanical properties such as strength, ductility, hardness, flexibility, impact resistance, elasticity, and fracture toughness. Furthermore, disclosed in-situ motion-sparing implants may be anisotropic in that their material properties may vary with orientation. In some applications, in-situ motion-sparing implants may be isotropic in that their material properties may be the same regardless of orientation.

In some embodiments, an additional material grown, formed, or added is a bone-growth-promoting material (BGM). The material can also be injected in-situ into the implant, such as when the implant is only partially grown or formed, and the BGM can best be deposited to desired intra-implant positions.

The present technology can be implemented with any of various additive-manufacturing techniques. The selected method would be executed at least partially in-situ, adjacent patient tissue, such as one or more vertebrae.

Care, in material preparation (e.g., heating) and in some cases material deposition (e.g., location or timing of depositing) should be taken regarding the temperature to which patient tissue is exposed.

Materials that must be at higher temperatures for initial application to the in-situ sight, such as metals, should be used strategically, or a different implementation of the present disclosure should be used. In a contemplated embodiment, a first layer or layers of a cooler powder or liquified material is applied before a layer of hotter liquified material, such as metal, is applied carefully over the first layer, and so not in contact with the patient. The amount of heat that would in this case still transfer, through the first layer, to the patient should be considered. In some implementations, the first material should be sufficiently cooled or solidified before the second is introduced, and in any event have sufficient insulative properties.

In some embodiments, material, such as powder, is put in place, by a dispensing element, and then materially altered, such as chemically or by heat. Some materials can be effectively melted by chemical treatment. For these embodiments, care should be taken to ensure that patient tissue is not exposed to undesirable affects, including by not limited to undesirable levels of heat.

Any of various printing material can be used, including material that are biocompatible, and materials that effect desired activity in the patient, such as materials promoting bone growth on, through, around, or adjacent the in-situ-grown or formed implant.

Regarding additive techniques, generally, any suitable printing method may be used. Suitable printing techniques allow generation of the implant in-situ, at least partially in the patient, without injuring the patient undesirably. Example additive techniques include, generally, Stereolithography (SLA), Digital Light Processing (DLP), Fused deposition Modeling (FDM), Selective Laser Sintering (SLS), Selective Laser Melting (SLM), Electronic Beam Melting (EBM), Laminated Object Manufacturing (LOM), and Binder Jetting (BJ).

An example in-situ printing technique is now described. In a powder technique, an implant is built at least partially in the patient by laying down a layer of powder in a desired configuration and location adjacent patient tissue (e.g., a patient vertebra). The powder can include a rigid thermoplastic, such as Poly(methyl methacrylate) (PMMA). This layer can be referred to as a substrate.

After the substrate is applied, a catalyst is applied to the substrate. Example catalysts include an adhesive, such as a medical-grade glue, a chemical additive, a curing material, or energy, such as heat, electron beams, radiation.

This process of printing layers is repeated in locations and amounts, selectively, to grow or form the desired implant geometry adjacent the patient tissue.

In another technique, beads are used. A dispensing component, such as a nozzle, introduces a layer of beads or particles at desired locations and amounts. The same nozzle, or another dispensing instrument, then applies a catalyst, such as an adhesive, curing additive, or energy (e.g., heat to melt) the beads, to convert the state of the beads, such as hardness, rigidity, flexibility, and shape.

In a contemplated embodiment, the nozzle includes an energy-applying element, such as a heating element.

A polymer, or other material, having a relatively low melting temperature could be used to avoid injuring tissue.

In some, fixed-end, embodiments, the system 100, including one or more dispensing components 110 and any other desired end effector/s, such as the mentioned heat applicators, are configured so that selected end effectors are fixedly attached (i.e., not readily removable/attachable) to robotics armature.

The dispensing component 110 may be referred to by a variety of terms, such as nozzle, dispenser, and applicator.

In other, modular, embodiments, the system 100, including one or more dispensing components 110, and any one or more other desired end effector, can be configured so that the end effectors can be readily attached to and removed from the robotics armature. The armature and the end effectors have mating features, for selective engaging each other, such as mating threads, tab/slot, other interlocking features, the like, or other. The features are for simplicity in the drawings considered illustrated schematically by reference numeral 111, which can still be a joint allowing relative articulation between the dispensing component 110 (and/or any other end effector) and arms or armature 112. The connection nodes 111 and arms 112 can include any number of nodes and arms, though either one or multiple are at times described by way of example herein.

Any of the system 100 components can be combined into a kit, in manufacture, or for sale or distribution.

To genericize descriptions of the various two-step-printing embodiments for simplicity herein, material or particles first laid on patient tissue are referred to as a substrate at times herein. And energy (e.g., heat), adhesive, chemicals, curing additives, etc., applied on the substrate are referred to generally as a catalyst at times herein. In contemplated embodiments, a single printing material is used, or more than one substrate material and/or more than one catalyst are used.

To allow desired post-operation motion in the patient, or to allow only a desired motion or motions, the printing material can include a non-rigid material. The material could be gummy, for instance, to form a motion-sparing, or motion-allowing, implant.

Turning now to the drawings, and more particularly to the first figure, FIG. 1 shows schematically a nozzle or dispensing component 110 of a surgical additive-manufacturing system 100 according to various embodiments of the present technology.

The component 110 is shown schematically in axial view adjacent a first patient vertebra 120. The vertebra includes a body 130 having a cortical rim 140 surrounding a cancellous end plate 150.

The dispensing component 110 can take any suitable shape or form. While the dispensing component 110 is shown schematically as a generally conical nozzle in the drawings, the component in various embodiments has other shapes, such as frustro-conical, cylindrical, tubular, prismatic, needle-like, and a non-descript shape, such as one that is ergonomic or custom-shaped to fit a patient-access. The component 110 can be rigid or flexible, of flexible and rigid in various portions.

The dispensing component 110 is connected to upstream components of the system 100 by at least one positioning or control arm 112. In various embodiments, connecting structure 111, shown schematically in FIG. 1, connects the dispensing component 110 and the control arm 112. Connecting structure 110 can also connect distinct components of the system armature 112, as shown by way of example in FIG. 10.

As described further below in connection with FIG. 10, the control arm 112 is actuated to position one or more dispensing components 110 as desired for depositing one or more materials in-situ to select locations in the patient. System movements are in various embodiments controlled by robotics. In contemplated embodiments, any or all control-arm movement can be controlled or assisted manually, such as by a surgeon.

In a contemplated embodiment, the system 100 is configured to enable a remotely located surgeon to control aspects of the system 100. The system 100 can be configured, for instance, to allow the surgeon to, from the remote location, control operative characteristics such as position and orientation of the dispensing component 110, and material-dispensing rates. For this, the computing components 1060 of the controller 1050 are configured to communicate with actuation controls. The remote actuation controls can include those that are (a) mechanical, such as one or more handles, control sticks, the like or other, (b) automated, such as a computer to (b)(i) present images or other data from the patient-theater controller 1050 to the surgeon, and (b)(ii) transfer data indicative of surgeon movements, from the mechanical actuation controls, to the system controller 1050, for actuating the on-site system components—e.g., pump/s 1040, robotics 1030—accordingly.

In various embodiments, any or all such remote componentry is a part of the system 100.

The pumps 1040 may be referred to by any of various terminology, such as a provision component, material-supply component, material supply, material-actuating system or subsystem, the like, or other.

The control arm 112 can include a single arm, or multiple arms or sub-parts. The control arm 112 can take any suitable shape or form. While the control arm 112 is shown schematically as generally cylindrical in the drawings, the component in various embodiments can have any suitable shape, and be rigid, flexible, or flexible and in various portions.

The dispensing component 110 is in various embodiments configured—size, shape, material, etc.—to enable careful delivery of printing material, such as powder, particles, or a stream or thread of material, such as a gel or other liquid or partially or semi-liquid material. Application of material in consistent layers is desired in some implementations, for example.

It is desirable for the dispensing component 110 to be configured to dispense precise amounts of printing material—e.g., substrate and catalyst—to specific locations within the patient.

Such features of the technology allow in-situ growing of implants having desired strength, and precise intra-patient positioning and geometry. Proper shape, make-up, and positioning ensure that the implant will function in the patient as desired, for instance, and not impinge on areas of the patient that the implant is not intended for. The dispensing component 110 could, for instance, include at least one strain gauge or other device (not shown in detail) for registering or sensing force at the component 110. While such sensing device is not shown expressly in the drawings, the dispensing component 110 is considered to by its showing include showing the gauge, as they can be generally or fully designed to be seamless, or otherwise on and/or beneath the surface of the component 110 so as not to adversely affect component 110 movement—e.g., so as not to impinge undesirably with patient tissue or any adjacent surgical instrumentation during the surgical procedure. A computing controller 1050, described further below, can be adapted to control the nozzle partially based on this nozzle gauge output.

When the nozzle (gauge) bumps into surrounding anatomy, in dispensing component approach, positioning movement, or printing movement, the nozzle can be moved accordingly to limit or avoid the bumping. In a contemplated embodiment, the gauge is sensitive to detect objects that the nozzle should not contact, before contact. The nozzle can thus be maneuvered to avoid the contact. This can be referred to as a proximity subsystem, a proximity-avoiding subsystem, or the like. In a contemplated embodiment, the system 100 includes a circuit or switch that adjusts nozzle movement to some extent based on the gauge feedback. In this case, the computing controller 1050 can do less or none of the correction based on gauge feedback.

In one embodiment, the gauge(s) is configured and used to facilitate registering patient bone quality and adjusting the implant accordingly. For instance, if the gauge senses weak, or relatively weaker bone material adjacent the dispensing component 110, the system 100 (e.g., computing controller 1050) could apply material accordingly, such as in higher volume or in a special configuration to better address the weakness, such as by a configuration that covers more surface area at, in, or adjacent the weak area. The converse can be true. That is, less material or a special configuration can be used when strong bone is detected, such as by using less material, which can save material and time, and so cost, and be less invasive. Custom inner configuration, such as void or channeling, formed custom to adjacent patient tissue condition is mentioned below.

The dispensing component 110 can as mentioned include multiple nozzles or other implements, such as an energy-application element, to accomplish the aims of the present technology.

For implementations in which multiple materials are applied adjacent patient tissue, the dispensing component 110 can include (A) an arrangement of multiple corresponding dispensing components 110, or (B) a single dispensing component 110 by which multiple materials can be dispensed selectively. Three exemplary multi-material-dispensing arrangements are described below in connection with FIGS. 2-3, 4-5, and 6-9. Although the arrangements are described as multi-material, the one described as a catalyst can as mentioned be other than a material, such as by being an energy, such as heat, electron beam, or radiation.

In various embodiments the first material $220^1$ is delivered to the first dispensing component $110^1$ via a first transport component, such as a conduit, channel, pipe, or tube. And the second material $220^2$ is delivered to the second dispensing component $110^2$ via a second transport component. Transport components $210^1$, $210^2$ are indicated schematically in FIGS. 2-10.

Various conduits, channels, and the like are described herein, such as in connection with nozzles, or dispensing components, system arms, etc. While these various elements are in some cases described separately, such as one in the nozzle connected to one in an adjacent arm, the descriptions are meant to include embodiments in which the two adjacent elements can be a single element, including in the claims. A single channel can be used when two connecting channels, or a channel and a transport component, e.g., are described or claimed.

FIG. 2 is an axial view of a first exemplary multi-material-dispensing arrangement 200 having at least two dispensing components $110^1$, $110^2$. The dispensing components $110^1$, $110^2$ are connected by connecting structure 111. The connecting structure 111 can include any suitable number of connection points or nodes $111^0$, $111^1$, $111^2$. Any of the nodes $111^0$, $111^1$, $111^2$ may be joints, for instance, about which adjacent structure (nozzle and/or arms) can move relative to each other.

An entry node $111^0$, for instance allows an entry arm $112^0$ to articulate vis-à-vis first and second delivery arms $112^1$, $112^2$. Or, vice versa—i.e., allow the arms to be controlled to articulate with respect to the entry arm. A first node $111^2$ allows the first delivery arm $112^1$ to articulate with respect to the first dispensing component $110^1$, and vice versa. And a second node $111^2$ allows the second delivery arm $112^2$ to articular with respect to the second dispensing component $110^2$, and vice versa.

Components upstream of the dispensing component 110 can be referred to as positioning components. The view of FIG. 2 shows the multi-material-dispensing arrangement in a first mode, wherein the positioning components (e.g., arms $112^0$, $112^1$) are arranged so that the first dispensing element $110^1$ is positioned to dispense a first printing material 230 in-situ to the patient, and particularly in this example to, or to and adjacent, the end plate 150 of the first vertebra 120.

The first dispensing component $110^1$ receives, via at least one transport component $210^1$, a first in-situ implant-growing material $220^1$.

The dispensing component $110^1$ is maneuvered, by moving the control arms (e.g., arms $112^0$, $112^1$) and any connecting components (e.g., connectors $111^0$, $111^1$) in any suitable manner for preparing to dispense, and dispensing, the first material $220^1$ as desired. The action is indicated by example arrow in FIG. 2.

The first material $220^1$ can as referenced be referred to as a substrate material for some embodiments. The material may include PMMA or another thermoplastic, and be in power form, as mentioned. In a contemplated embodiment, the substrate material is dispensed in any of various other forms, such as liquid, semi-liquid (e.g., gel), slurry, or another form.

In a contemplated embodiment, only the first material $220^1$ is applied for the first layer, and the second and subsequent layers include the same.

As mentioned, in various embodiments, after the first layer, of the first material $220^1$, is applied, a second layer of a second implant-printing or -growing material $220^2$ is applied in-situ, as shown in FIG. 3.

The second dispensing component $110^2$ is maneuvered, by moving the control arms (e.g., arms $112^0$, $112^2$) and any connecting components (e.g., connectors $111^0$, $111^2$) in any suitable manner for preparing to dispense, and dispensing, the second material $220^2$. The action is indicated by example arrow in FIG. 3.

Transitioning from using the first dispensing component to the second may in some cases require removing the first dispensing component from the patient to make room for inserting the second component. The same is true in these cases for transitioning from the second to the first dispensing component.

In a contemplated embodiments, relevant system components, including the dispensing components especially, are sized, shaped, and connected to other system components (e.g., armature 112, connector/s 111) so that the transition can be effected without removing them from the patient fully, or even without removing the dispensing components from the patient at all.

In FIG. 3, the second dispensing component $110^2$ is shown dispensing the second material $220^2$. The second material $220^2$ is applied to or on the first material $220^1$.

The second dispensing component $110^2$ receives, via at least one transport component $210^2$, the second in-situ implant-growing material $220^2$.

The system 100 including upstream source and actuation components (e.g., pumps), selectively push or pull the first and second materials $220^1$, $220^2$ through the dispensing components $110^1$, $110^2$, selectively Upstream components are described further below in connection with FIG. 10.

The second material $220^2$ can as mentioned be a catalyst. An example catalyst is an adhesive, or glue, but is not limited to these. The catalyst can also include an energy, chemical, additive, or other material causing a reaction such as curing for the first material $220^1$. The nozzle or other implement may be configured to apply heat, electrons, photons, lasers, radiation, the like or other, for instance.

Figure 4:
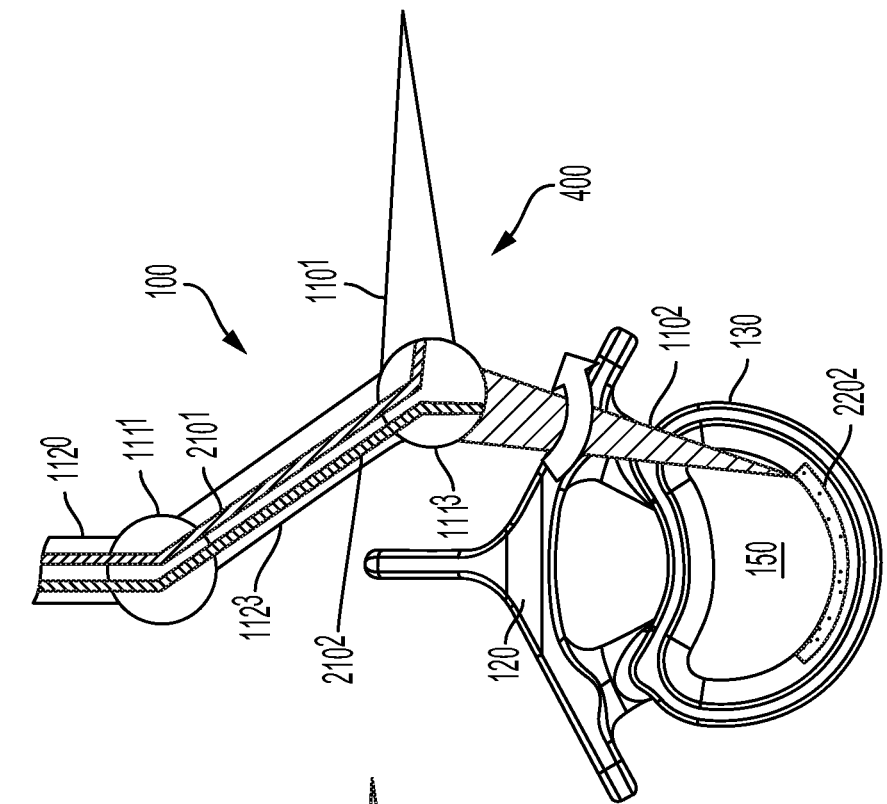
FIG. 4 is an axial view of a multi-dispensing arrangement, in a first, substrate-dispensing, mode, of the additive-manufacturing system, positioned adjacent the patient vertebra according to a second exemplary embodiment of the present disclosure.
Figure 5:
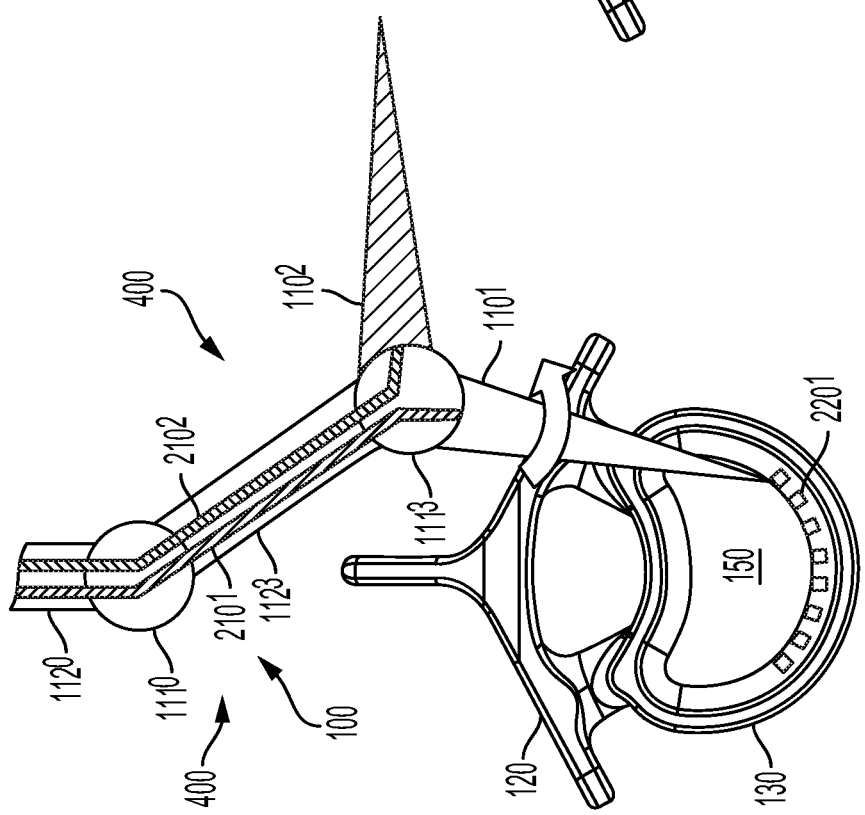
FIG. 5 is an axial view of the multi-dispensing arrangement, in a second, catalyst-dispensing, mode, positioned adjacent the patient vertebra according to the second exemplary embodiment.

FIGS. 4 and 5 show a second example multi-material-dispensing arrangement 400 for providing the substrate and catalyst $220^1$, $220^2$. The arrangement includes any number of connecting structures to which the dispensing components $110^1$, $110^2$ are connected, such as the example connecting structures $111^0$, $111^3$.

As in other embodiments, any number of connection structures can be used, of any size, shape, or material, including flexible and/or rigid. First and second transport components $210^1$, $210^2$ deliver the first and second materials $220^1$, $220^2$ to the dispensing components $110^1$, $110^2$.

The system 100 including upstream source and actuation components (e.g., pumps, augers, screws, conveyors, etc.), selectively push or pull the first and second materials $220^1$, $220^2$ through the dispensing components $110^1$, $110^2$. Upstream components are described further below in connection with FIG. 10.

FIGS. 6-9 show a third example multi-material-dispensing arrangement 600 for dispensing the first and second materials 230, 330. The arrangement 600 includes any number of connecting structures to which a single dispensing component $110^3$ are connected, such as the example connecting structures $111^0$, $111^4$ shown. As in the other embodiments described herein, any suitable or desired number of connection structures can be used, of any size, shape, or material, including flexible and/or rigid.

The system 100 including upstream source and actuation components (e.g., pumps), selectively push or pull the first and the second materials $220^1$, $220^2$ through the dispensing component $110^3$, selectively. Upstream components are described further below in connection with FIG. 10.

In contemplated embodiments, any of the system components—such as connecting components 111, transport components 210, or upstream source 1020 or actuation components 1030—include flow-control components (not shown in detail), such as valves, to regulate which material is fed to or through the dispensing component $110^3$, and in some cases by what amount or rate.

In various embodiments, either the first or second material $220^1$, $220^2$ is pushed through the transport components 210 at any one time, forcing that material through and out of the dispensing component $110^3$ and into the patient. As one of the materials ($210^1$ or $210^2$) is pushed through the dispensing component $110^3$, a sufficient amount of the other material ($210^2$ or $210^1$) residing in the dispensing component $110^3$ at the time, is forced out of the dispensing component until the material ($210^1$ or $210^2$) being pushed begins to be dispensed.

In a contemplated embodiment (not shown in detail), the dispensing component $110^3$ is configured so that when the system 100 changes from a first-material-dispensing mode to a second, the second material need not displace much or any of the first material. In this case, conduits, channels or tubing of the dispensing component $110^3$ extend to or adjacent a tip of the dispensing component $110^3$, keeping the material separate, or substantially separate prior to dispensation from the component $110^3$.

In a contemplated embodiment, multiple materials, such as a substrate/catalyst mix, are delivered to the patient via the dispensing component $110^3$ at the same time. The two materials can be combined in any of various locations, such as at (i) a facility at which the reservoir/s 1020 are filled, (ii) at the surgical facility prior to surgery—out-of-room, at a back table, or in the surgical theater, (iii) in a reservoir (1020 or other) in the system base 1010, (iv) downstream of the reservoirs $1020^1$, $1020^2$, such as (iv)(a) within the base 1010 or adjacent and outside of the base 1010, (iv)(b) in any of the armature 112, such as in, at, or adjacent the base 1010 or dispensing component 110, (iv)(c) in any part of the nozzle, or (iv)(d) as dispensed (e.g., at a tip of the nozzle or outside of the tip after the materials are dispensed separately from the nozzle). The reservoirs can be referred to by various terms, such as storage, supply, or source.

In another contemplated embodiment, only one suitable implant-forming material is delivered from the dispensing component 110. In this embodiment, there is not a separate application of substrate and catalyst, for instance.

Figure 6:
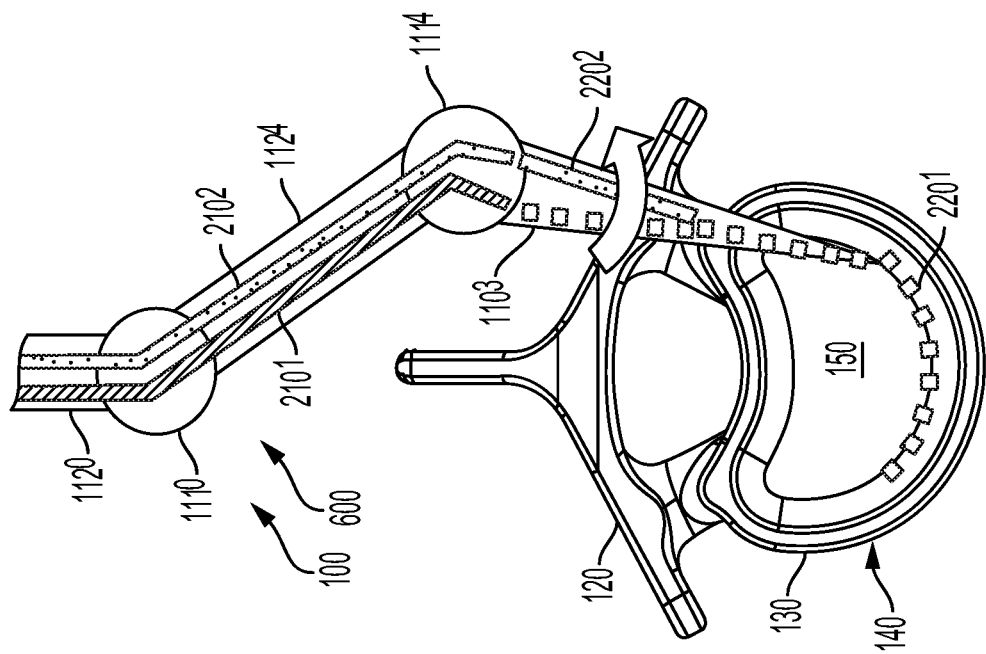
FIG. 6 is an axial view of a multi-dispensing arrangement of the additive-manufacturing system, in a first, substrate-dispensing, mode, depositing substrate material to the patient vertebra according to a third exemplary embodiment of the present disclosure.

FIGS. 6-9 also show example operation. FIG. 6 shows the first material $220^1$ being dispensed.

Figure 7:
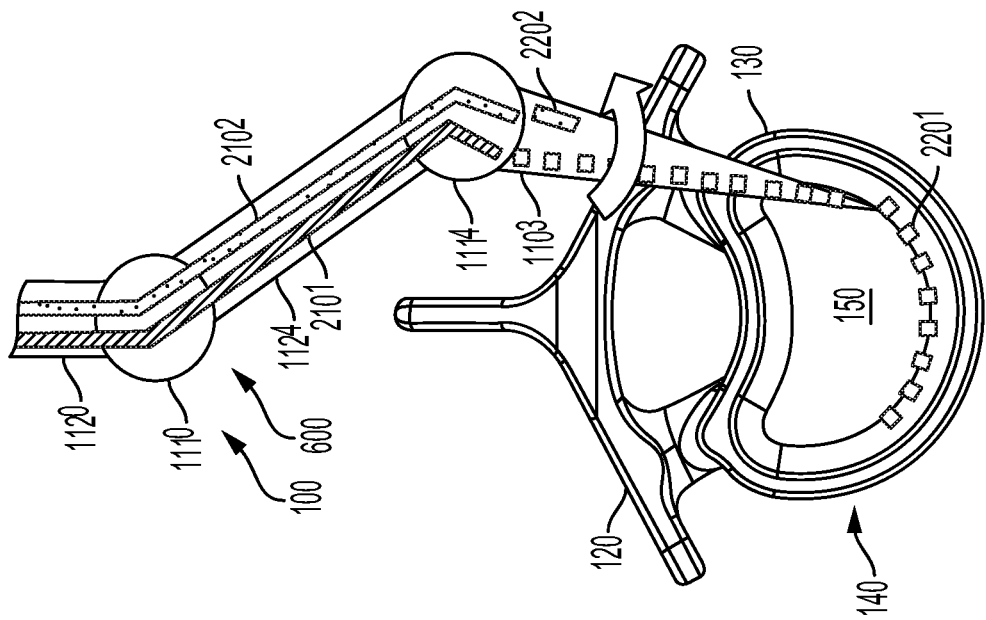
FIG. 7 is an axial view of the multi-dispensing arrangement, intra-transitional from the first mode to a second, catalyst-dispensing, mode, adjacent the patient vertebra according to the third exemplary embodiment.

FIG. 7 shows the first material $220^1$ continuing to be dispensed from the dispensing component $110^3$, as the second material $220^2$ begins to be pushed through the dispensing component $110^3$. At this point, the actuation causing or pushing the second material $220^2$, is thereby acting on the first material $220^1$ positioned still in the dispensing component $110^3$. The first material $220^1$ at this point is being forced out dispensing element $110^3$ by the force of second material $220^2$, which is being pushed through the dispensing component $110^3$. Example movement of the dispensing component $110^3$ is again indicated by arrow.

Figure 8:
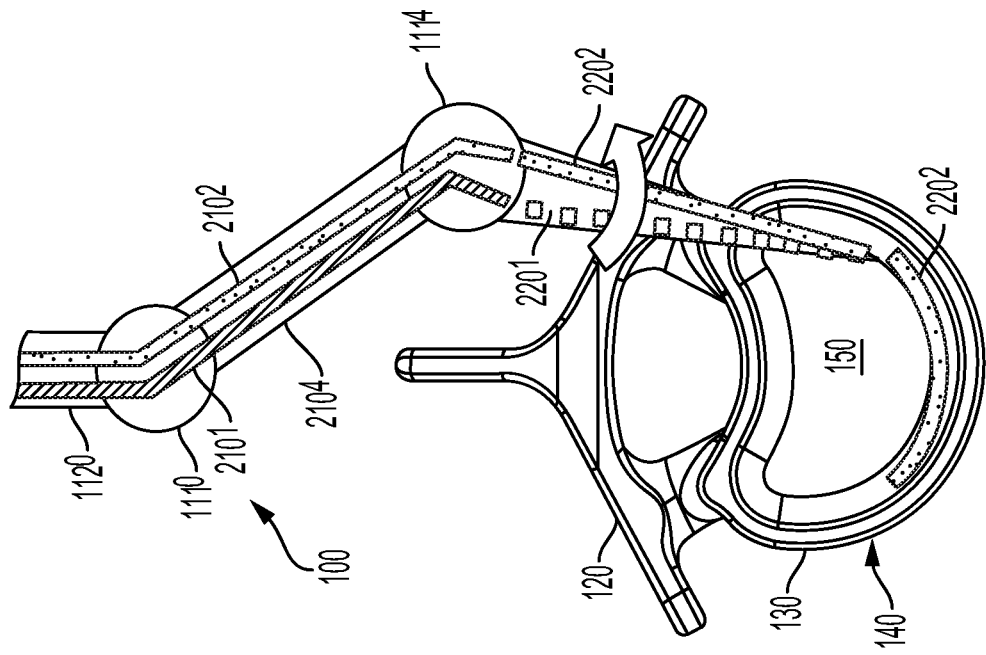
FIG. 8 is an axial view of the multi-dispensing arrangement, transitioned to in the second, catalyst-dispensing mode.

In FIG. 8, the second material $220^2$ has been pushed to the distal end or tip of the dispensing element $110^3$, so that the second material $220^2$ can now be dispense from the dispensing component $110^3$. Example movement of the dispensing component $110^3$ is again indicated by arrow.

Figure 9:
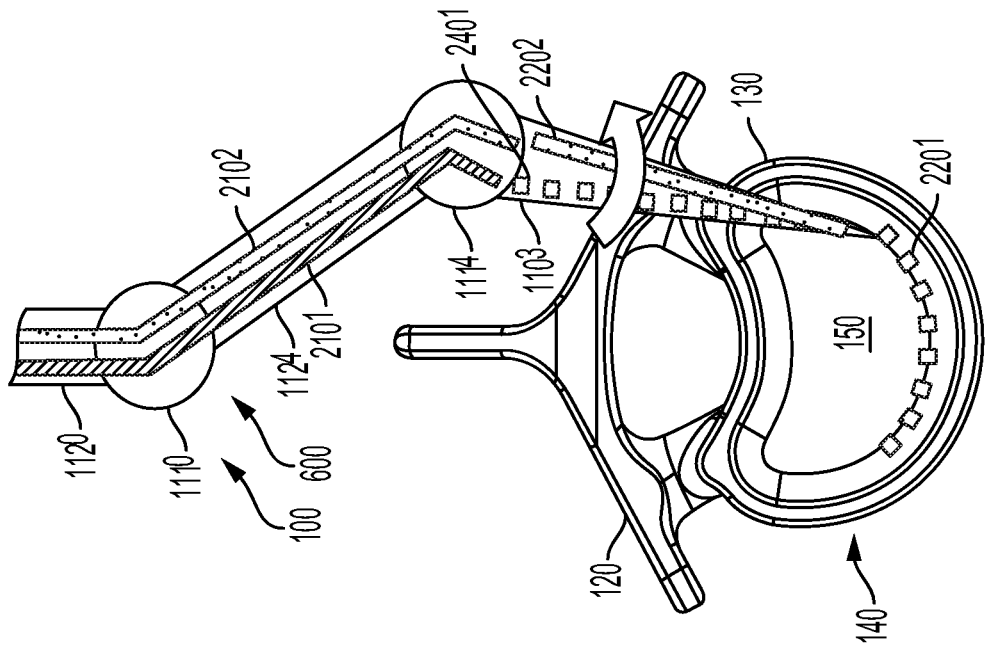
FIG. 9 is an axial view of the multi-dispensing arrangement, in the second, catalyst-dispensing, mode, depositing catalyst to the patient vertebra according to the third exemplary embodiment.

In FIG. 9, the second material $220^2$ is now being dispensed from the dispensing component $110^3$.

Figure 10:
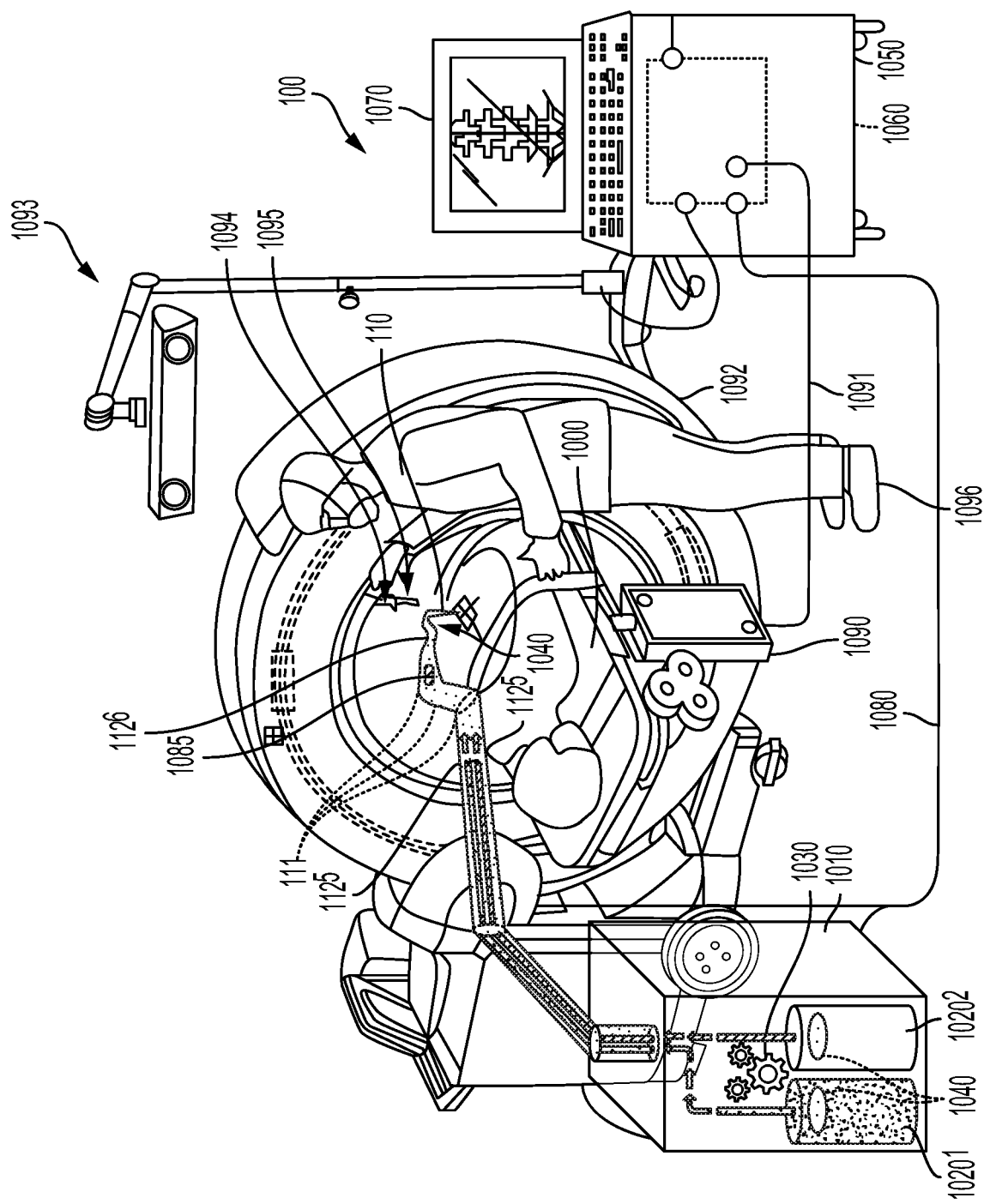
FIG. 10 is perspective view of the additive-manufacturing system positioned in theater for use with the patient.

Components of the system 100 are now described further in connection with FIG. 10.

The figure provides a perspective view of the additive-manufacturing system 100 positioned in theater for use with the patient 1000.

The dispensing component 110 extends from control arms or armature 112 and connecting components or nodes 111. The control arms 112, connecting components 111, and dispensing component 110 can be configured (numbered, sized, material, etc.) in any of various ways, including any of the ways described herein, such as in connection with FIGS. 1-9.

The structure of arms 112 may include, for instance, one or more rigid portions $112^5$ and one or more flexible portions $112^6$. The flexible and rigid locations can be positioned anywhere along the armature 112. While it is contemplated that greater dexterity will be useful closer to the end effector/s (110, etc.), flexible portions can be there, other location/s, or both.

Any armature portion may be connected by joints 111, shown schematically, to adjacent system parts, such as other arms or the dispensing component 110, as shown in FIG. 10, or a system base 1010.

The base 1010 includes at least one reservoir 1020, for holding the additive printing material 120. The reservoir 1020 is in various embodiments, whether in the base 1010, positioned adjacent or close to the end effector.

The arms 112 include or are connected to components for maneuvering the dispensing component 110 as needed for in-situ forming the additive implants of the present technology.

The control arm/s 112, connecting component/s 111, and the dispensing component/s 110 are actuated to desired positions for preparing to dispense and dispensing the implant-growing materials in-situ, to select areas adjacent tissue of the patient 1000. System movements are in various embodiments controlled by suitable robotics.

Robotics can include any suitable actuation and control componentry, is indicated schematically by reference numeral 1030.

In various embodiments, the base 1010 includes some or all of the robotics components, including controlling and actuating subsystems (not shown in detail).

The robotics equipment 1030 includes, is connected to, or is a part of the arms 112, for effecting desired arm movement, such as according to a pre-established surgical plan. The plan may be adjusted real-time based on sensing data, from a sensor with the dispensing component 110 or external to the patient. The sensing data may indicate that patient tissue is shaped or becoming shaped or positioned in a manner that was not anticipated by the plan, for instance. And a system controller, described further below, can be configured (e.g., coded) to thus make necessary adjustments to the plan, with or without surgeon or surgical staff intervention.

The robotics equipment 1030 can include or be connected to one or more pumps, indicated schematically by reference numeral 1040. The pumps 1040 are configured and positioned to push printing material $220^1$, $220^2$ selectively from the reservoirs $1020^1$, $1020^2$.

In a contemplated embodiment, the pump/s 1040, or additional pumps, are positioned upstream of the base 1010, such as in the robotics armatures 112, or in, at, or adjacent the dispensing component 110. If the upstream pump/s are provided in addition to one or more downstream pumps, the upstream pump/s can be referred to as booster pumps, amplifying pumps, or the like.

The robotics equipment 1030 includes or is connected to control componentry, such as computing equipment, indicated by reference numeral 1050 in FIG. 10.

Data communication connection between the controller 1050 and the robotics equipment 1030 and pumps 1040 can be wireless or wired, and is indicated by numeral 1080.

Reference numeral 1060 indicates components of the controller 1050. These can include any suitable automation, computing, or control componentry. Example components include (i) a communications bus, (i) a memory component storing computer-readable data, or instructions, such an in-situ-forming plan, which may be or include computer-aided-design (CAD) data, and (iii) a processor for receiving and executing the stored data to control and/or receive data from system components, such as the pump 1040 and robotics equipment 1030.

The controller 1050 in various implementations controls and/or receives data from one or more pieces of scanning equipment, any of which is considered a part of the system in some embodiments.

The memory component, of the computing components 1060 of the controller 1050, can be referred to by any of a variety of terms, such as a computer-readable medium, computer-readable subsystem, memory, storage, or storage component, and is in various embodiments non-transitory. The memory component may include any format or componentry, such as random-access memory (RAM) and read-only memory (ROM).

The controller 1050 can also include or be configured for ready connection to at least one interface for communication into and/or out of the controller 1050. The interface is indicated schematically by reference numeral 1070. The interface 1070 can include any available interface equipment, such as visual or audio input/output equipment, keyboard, etc. Visual input-and/or-output equipment can include a touch-sensitive display, such as a display screen showing an image of a portion of the spine of the patient 1000, rendered from sensing data, such as from sensing equipment 1093. In various embodiments, the sensing equipment is a part of or connected to the system 100. Visual components can include wearable visual components, such as one or more AR or VR components, such as at least one helmet, goggle or glasses, or the like, and are considered shown in the figures by the illustrated indication of i/o equipment 1070. The sensing equipment, whether part of the AR/BR component, or the illustrated remote sensors 1093, can sense surgeon movement. The system can also include one or more cameras, or visual sensing devices, such as an on-dispensing-component, on-robotic arm, camera, or other selectively positioned camera/s. The visualization equipment and such visual-sensing equipment can be connected to the controller 1050 such that (i) relevant visuals are provided to the surgeon and (ii) surgeon movements, e.g., hand movements, are translated, via the robotics, into movements or other functions of the dispensing component 110. In a contemplated embodiment, the controller 1050 can have a limited or no role in any of these functions—the wearable visual component can be connected wirelessly to the source visual sensor/s, for instance. As an example other control that the surgeon can influence in this way, outside of dispensing-component movement, a surgeon moving or squeezing her fingers together, such as toward making a fist, can to the extent of squeezing, affect amount and/or rate of dispensing of printing material 220.

The controller 1050 is communicatively connected with various apparatus by wire or wirelessly, all indicated schematically by reference numeral 1080. Example apparatus include controlled components, such as the pump/s 1040, robotics components 1030, and any other apparatus that communicates with the controller 1050, such as a scanning or imaging machine 1092. The imaging machine 1092 may include a separate computing system, as shown at left of the view of FIG. 10.

In contemplated embodiments, any or all actuations, including those for material pumping (1020), or armature 112 or dispensing component 110 positioning, can be effected or assisted manually, by surgical staff.

For some of the embodiments in which the dispensing component 110 is maneuvered manually, it is contemplated that the system 100 could include an actuator, such as a trigger, or button, or depressible portion of the dispensing component 110 or arm 112. The actuator, indicated schematically by reference numeral 1085 in FIG. 10, can also include or be connected to valves or other structure that can affect material flow as desired.

The term provision component can be used generally for any system components affecting the provision of printing material or energy to the dispensing component/s 1050 and in-situ location, such as the pumps 1040, an actuator 1085 causing material flow, a controllable valve affecting flow, or other suitable provisioning element or apparatus.

In various embodiments, the controller 1050 may be configured to control the pumps 1040. Wherever the pumps 1040 are located (in the base, or downstream thereof, e.g.), and whether the dispensing component 110 is controlled by robotics and/or manually by a surgeon, software (part of the automation components 1060) of the controller component 1050 can be configured to actuate pumping—i.e., control printing-material feed timing and/or rate, for instance—based on any of various factors.

Example factors include (a) the stage, phase, or time of a pre-established plan that the procedure is in, which plan may be programmed in software of the system controller 1050, such programming including a computer-aided-design (CAD) file, (b) position or orientation of the dispensing component 110, and (c) movement of the dispensing component 110.

Regarding the latter factor (c), it may be advantageous, for more-consistent, more-evenly, depositing, for instance, to dispense less printing material (lower-rate provision), or less material per time (rate), when the dispensing component 110 is being moved more slowly (robotically or manually), and more material (higher-rate provision) when the dispensing component 110 is moved more quickly.

For embodiments in which material feed rate is based on nozzle movement or position, the system 100 could include position- or motion-sensing componentry providing to the controller 1050 nozzle position or motion-indicating data. Data could also indicate arm 112 position or orientation, from sensors in the arms, connected to the arms, or remote sensors (see e.g., sensor 1093) in the room sensing navigation components (see e.g., components 1094). The remote features 1093, 1094 are described further below.

Sensing componentry that is in or connected to the armature or dispensing component 110 can also be considered indicated schematically by reference numeral 1085 for simplicity of the drawings.

The controller 1050, and more particularly the memory of the controller components 1060, can store a wide variety of data. Example datum include programs, patient identification or anatomy data, in-situ printing plans, machine-learning or artificial-intelligence code, or actual surgical procedure information, such as steps performed, results thereof, sensed features of the patient or printing process, etc. Any of the data, such as the surgical plan, can be partially or fully surgeon-created.

The system 100 is configured in various embodiments such that the data can be accessed, or generated, by a user, or another controller or computing system, via the controller interface 1070 or communication connection(s) 1080. Data can be transmitted from or to the controller 1050 by any suitable hardware or method, such as by wire, Bluetooth, Wi-Fi, portable drive, email, or any available communication technology.

In some embodiments, the controller 1050, by the controller components 1060, controls patient-positioning equipment, such as a surgical-table control system 1090. The controller 1050 is connected to the table control system 1090 by wire or wirelessly, both indicated by reference numeral 1091.

In a contemplated embodiment, the table control system 1090 is adjusted at least one time during the surgery, after a first stage of the in-situ printing, for improving positioning, spacing, dynamics, or the like, for a subsequent phase of the in-situ printing.

In various embodiments, the patient 1000 can be positioned at an angle with respect to horizontal, such as by tiling the table via the table control system 1090. Doing so may have a benefit of enabling printing on patient tissue (e.g., vertebral body end plate 150) while the tissue is positioned or orientated in an advantageous manner. Example advantageous manners can include, for instance, manners that (a) better allow the dispensing component 110 to fit into or be moved within the patient, (b) control, harness, or take advantage of material characteristics, such as to migrate or run when deposited on an angled surface (e.g., some powder or liquid substrates, before a catalyst is applied), and (c) avoid or harness gravity.

As referenced above, the control componentry 1050 in contemplated embodiments controls and/or receives information from sensing equipment to facilitate the in-situ implant printing. Example sensing equipment includes the scanning or imaging machine 1092. The scanning machine 1092 is positioned to obtain images of the patient in preparation for and/or during the in-situ-printing (ISP) procedure.

Pre-procedure scanning can include or be part of a registration process and surgical plan. The registration, surgical planning, and registration and plan storage can be performed by the controller 1050 and/or by other computing devices.

The surgical plan can be partially or fully surgeon-created.

Scanning data can be used by the controller 1050 to recognize and record desired patient position for the surgery, including position of patient anatomy, including injured or compromised areas. Repeated scannings can be performed—one or more prior to the surgery, typically on a day prior to the surgery, and again to prepare for the surgery, day-off, ensuring that the patient is positioned as desired. The registration can include registration data for the patient in multiple positions for the surgical plan, as mentioned above.

As mentioned, the system 100 can include or be used with navigation sensing system 1093. The navigation sensing system 1093 senses targets 1094 affixed to a navigation instrument 1095, such as a navigated guide, surgical drill, or bone-screw driver.

In various embodiments, any of the nav components 1093, 1094, 1095 are part of the system 100.

Navigation equipment 1095 can be maneuvered for its purpose by the surgeon 1096 and/or by the controller componentry 1050 and robotics 1030, based on data received from the navigation sensing system 1093. Regarding robotic control, the nav instrument 1095 could be an end effector, connected to the armature 112, of the system 100, for example. Navigation data is used by the controller 1050 or surgeon for positioning the navigation equipment 1095 precisely as needed to execute a surgical maneuver.

The maneuver facilitated can include positioning the dispensing component 110 for printing. The dispensing component 110 or distal armature 112 can include the navigation targets 1094 for this, for instance.

Whether navigated, embodiments in which robotics equipment is used for surgical functions, outside of printing functions, can include any related surgical procedures. For spinal surgeries, for instance, the system 100 can include or be connected to instruments for distraction or correction. By distraction, the robotics equipment or surgeon would apply appropriate forces to manipulate vertebral bodies as desired or needed, such as to size or shape the intervertebral space (reference, e.g., the space indicated by 3610 in FIG. 36), or to orient one or more vertebra of the spine otherwise as desired. The distraction using robotics could be used specifically to gain access to the disc space, or for correction after the implant is printed. The robotics could, for instance, move the vertebral bodies such that the printed implant (e.g., cage) doesn't contact one or both of two adjacent endplates initially, and then move the vertebral body/ies to contact cage. As another example, the implant could be printed with protrusions, such as spikes, such that moving the adjacent vertebral body/ies to contact the implant would drive the protrusions into the vertebral body/ies, promoting implant-securement in place. Such 'positive' (versus 'negative', like holes, channels, etc.) features are describe further below.

In various embodiments, the surgeon or robotics 1030 moves or otherwise adjusts the implant after it is formed.

Some example procedures will now be described further.

Figure 11:
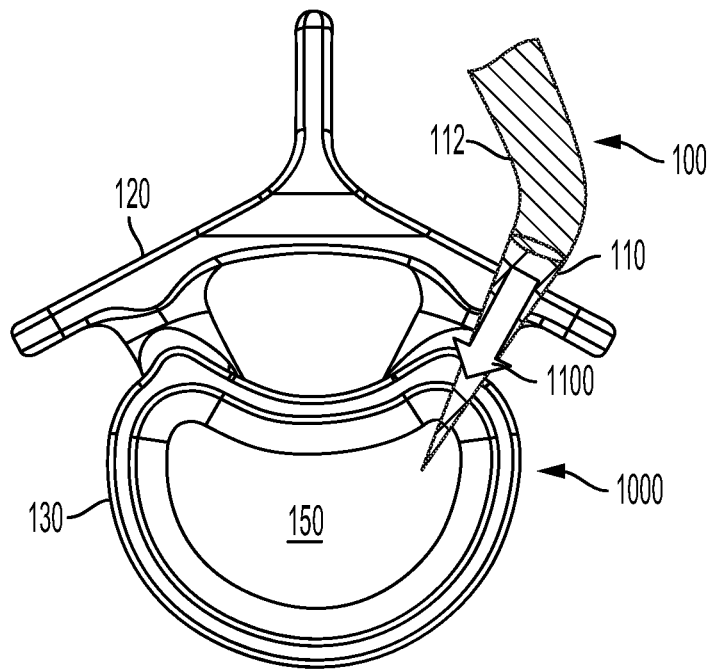
FIG. 11 is the axial view of FIG. 1 with the dispensing component of the additive-manufacturing system being moved toward an in-situ position of the patient.

FIG. 11 is the axial view of FIG. 1 with the dispensing component 110 of the additive-manufacturing system 100 being moved toward a desired or pre-planned in-situ printing position of the patient 1000 adjacent the patient vertebral body 130. Dispensing-component movement, shown schematically by arrow 1100, is in various embodiments controlled by the controller 1050 and the robotics equipment 1030.

The robust fixation between the implant being grown or formed and patient tissue 120, 122, enabled by printing a patient-shaped implant in-situ, may be enhanced by preparing printing features into or on the implant and/or preparing the tissue in a suitable manner, such as by roughening or grooving.

The implant features promoting implant-to-tissue adhesion and/or connection can include surface roughening, surface shaping (e.g., teeth, grooves, channels), and surface coating, or physical features that penetrate patient tissues, such as bony surfaces, e.g., vertebral bodies, or features for attaching post-printing devices such as eyelets for inserting screws. The surface features, whether a level of roughness, smoothness, and/or other features, can be configured to promote or control bone growth on, at, or adjacent the implant, or protect adjacent anatomy. Generally, a rougher surface promotes bone growth, while a smoother surface limits affects on adjacent anatomy.

The implant of this embodiment, or any embodiment herein, can also be formed to have geometry promoting any of strength, weight, and bone growth. Regarding the latter, the implant can be formed to have at least one hole, recess, or hollow, partially or fully through the implant, for instance, to promote bone growth into or through the implant.

Figure 12:
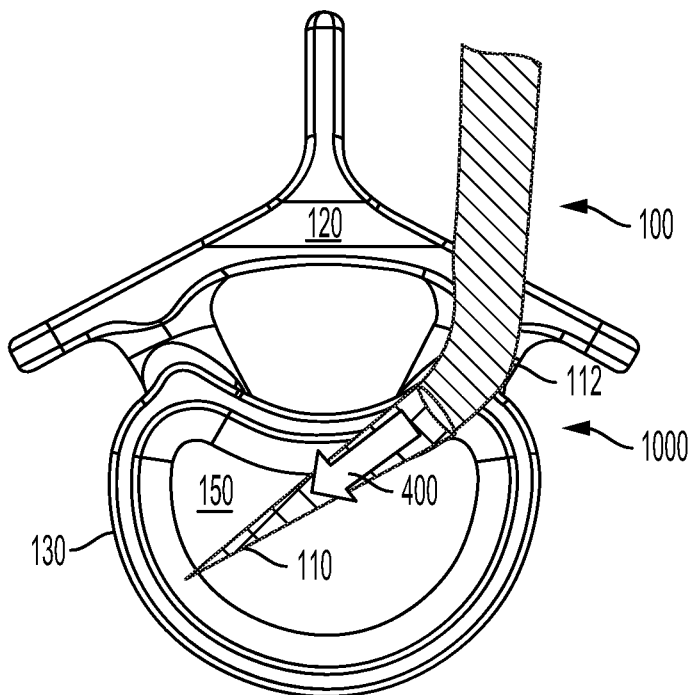
FIG. 12 is the axial view of FIG. 1 with the dispensing component moved to an example in-situ position of the patient according to a first general embodiment of the present technology.

FIG. 12 shows the dispensing component 110 moved to an example in-situ position of the patient 1000 according to a first general embodiment of the present technology. The movement is indicated by arrow 400.

Embodiments are referred to as general because they are agnostic to which particular dispensing-component arrangement is used, such the arrangements 200, 400, 600 of FIGS. 2-9.

Figure 13:
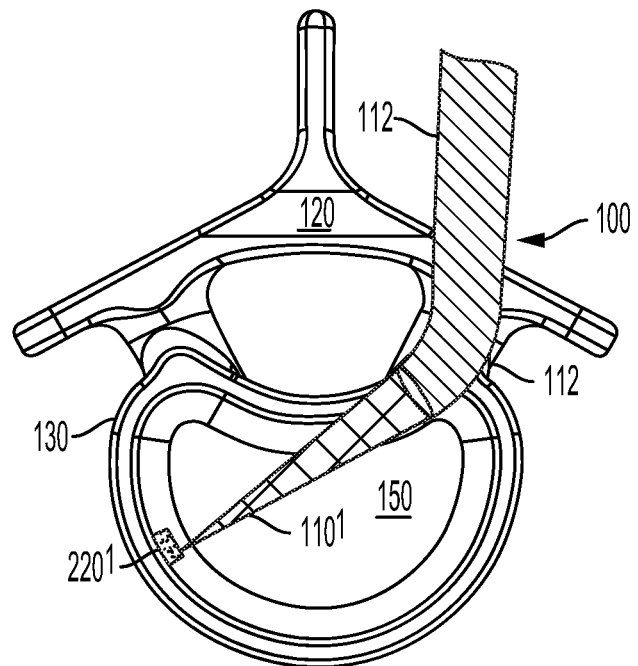
FIG. 13 shows commencement of in-situ formation of a first interbody implant, by the dispensing component, dispensing a first row of a first, substrate, material, to the in-situ position of the patient according to the first general embodiment of the present technology.

FIG. 13 shows commencement of in-situ formation of a first interbody implant, by the dispensing component 110, dispensing a first row of a first, substrate material $220^1$, to the in-situ position of the patient 1000.

The dispensing component 110 can, as described include any of those shown and described herein. The dispenser 110, applying the first material $220^1$, can be, for instance, any of the first-material dispensing nozzles $110^1$, $110^3$ described with the arrangements 200, 400, 600.

Figure 14:
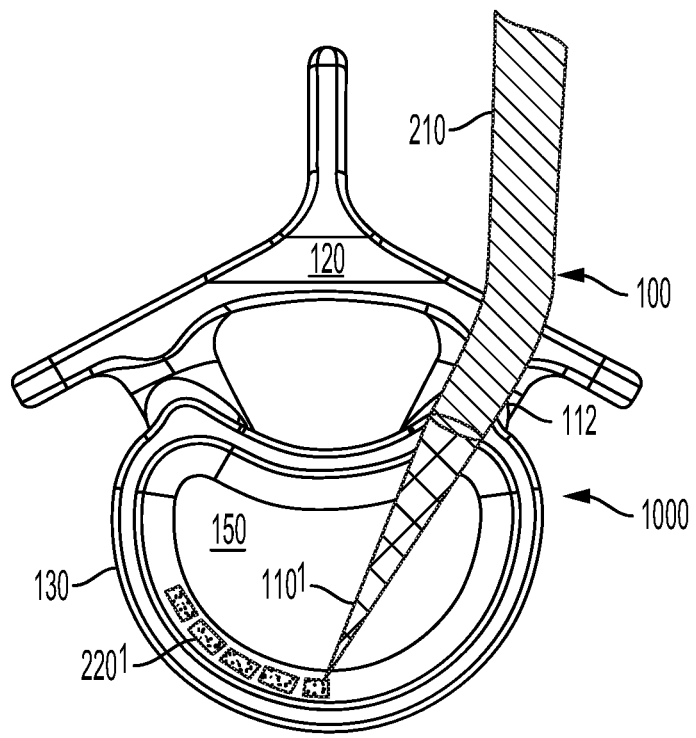
FIG. 14 shows the dispensing component continuing to dispense the substrate material to the in-situ position of the patient according to the first general embodiment of the present technology.

FIG. 14 shows the dispensing component 110 continuing to dispense the substrate material $110^1$ to the in-situ position of the patient 1000.

Figure 15:
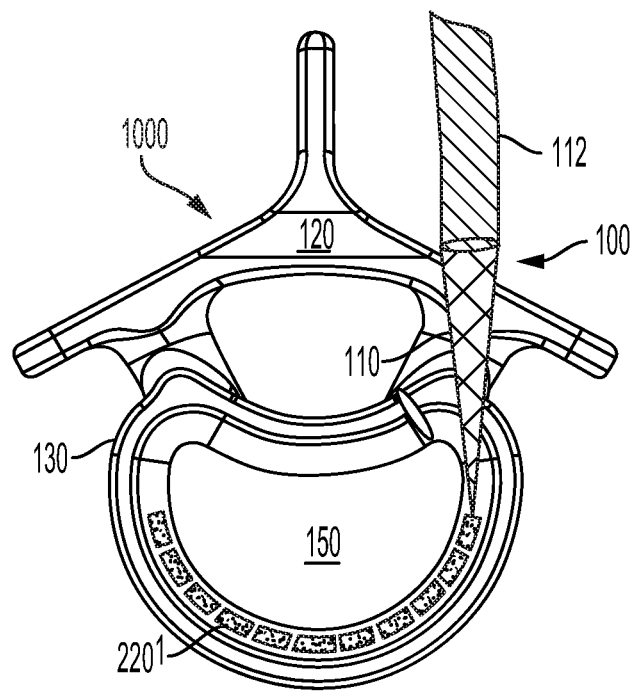
FIG. 15 shows the dispensing component completing depositing of a first row of substrate material at the in-situ position of the patient according to the first general embodiment of the present technology.

FIG. 15 shows the dispensing component 110 completing dispensing of a first row of substrate material $220^1$ at the in-situ position of the patient 1000.

Figure 16:
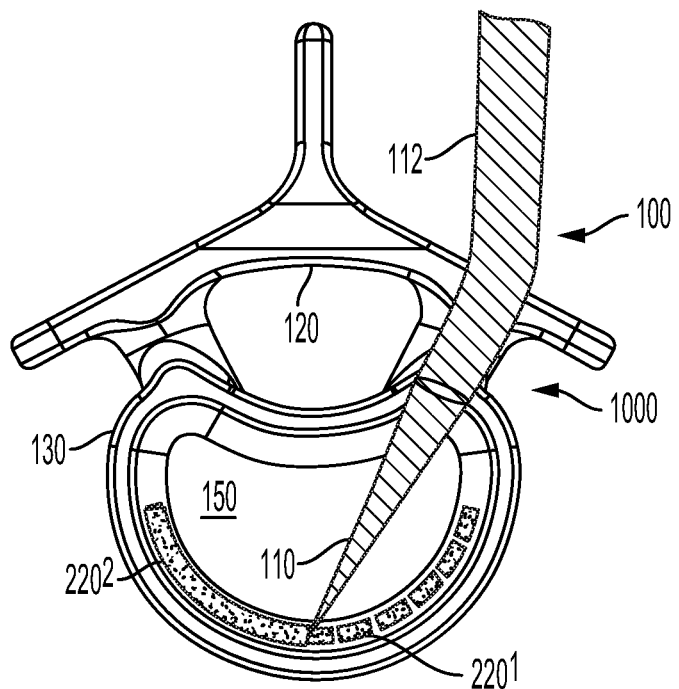
FIG. 16 shows the example dispensing component dispensing catalyst, over or to the first-row substrate material at the in-situ position of the patient according to the first general embodiment of the present technology.

FIG. 16 shows the dispensing component 110 dispensing a catalyst $220^2$ over the first-row substrate material $220^1$ at the in-situ position of the patient 1000. The catalyst can as mentioned include any of various applications, such as adhesive, curing material, or energy such as heat, electron beam, or radiation.

The dispensing component 110 can again here include any of those shown and described herein. In the view of FIG. 16, the dispenser 110, applying the second material $220^2$ can be, for instance, any of the second-material dispensing nozzles $110^2$, $110^3$ described with the arrangements 200, 400, 600.

Figure 17:
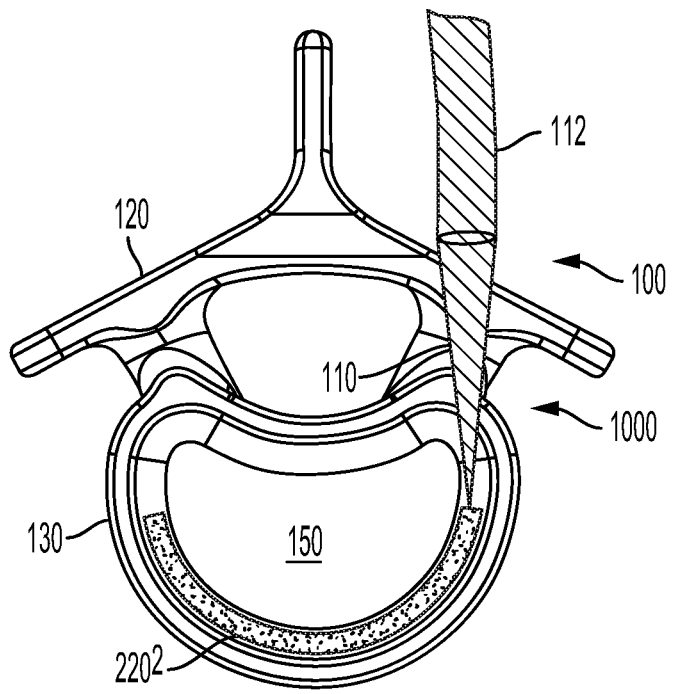
FIG. 17 shows the dispensing component completing the first row of catalyst over the first-row substrate at the in-situ position of the patient according to the first general embodiment of the present technology.

FIG. 17 shows the dispensing component 110 completing the first row of catalyst $220^2$ over the first-row substrate $220^1$ at the in-situ position of the patient 1000.

Figure 18:
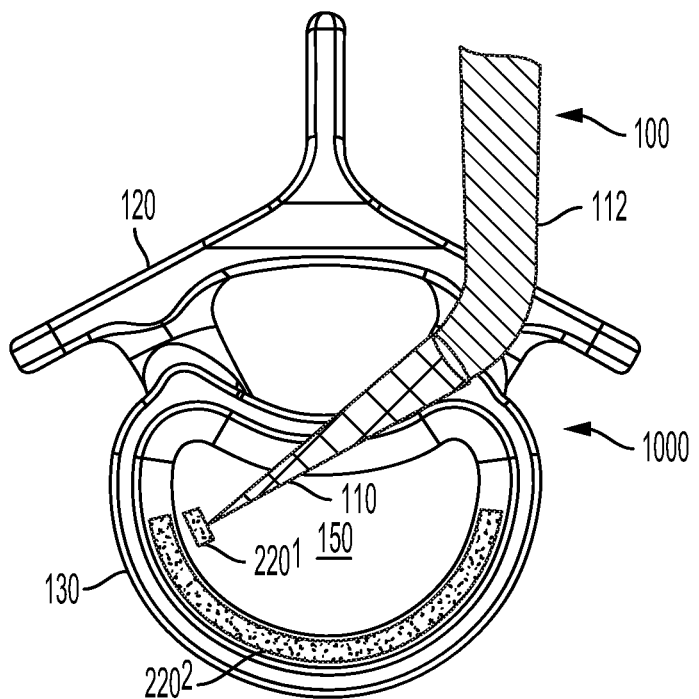
FIG. 18 shows the dispensing component dispensing a subsequent row of substrate material to the in-situ position of the patient according to the first general embodiment of the present technology.

FIG. 18 shows the dispensing component 110 dispensing a subsequent row of substrate material $220^1$ to the in-situ position of the patient.

FIG. 19 shows the dispensing component 110 completing dispensing of the subsequent row of substrate $220^1$ at the in-situ position of the patient 1000.

FIG. 20 shows the dispensing component 110 dispensing catalyst $220^2$ over the subsequent-row substrate material $220^1$ at the in-situ position.

FIG. 21 shows an example completed first-layer 2100 of the additive in-situ implant.

In various embodiments, the printing does not have to be strictly layer-by-layer. A first layer can be started, then a second, then a third, then addition to the first or second before starting the fourth, as an example.

In various embodiments components can be moved, by the system 100 (e.g., dispensing component 110 or another end effector) or surgeon, after being formed, to fit or better fit in a desired intra-patient position.

FIG. 22 shows the dispensing component 110 beginning a subsequent layer of substrate material $220^1$ over the first completed layer 2100 at the in-situ position of the patient 1000.

The process is continued, layer by layer, or portion by portion, to complete the in-situ-printed spinal implant. The particular sort of implant can be referred to as an in-situ-grown or formed interbody or cage.

Figure 23:
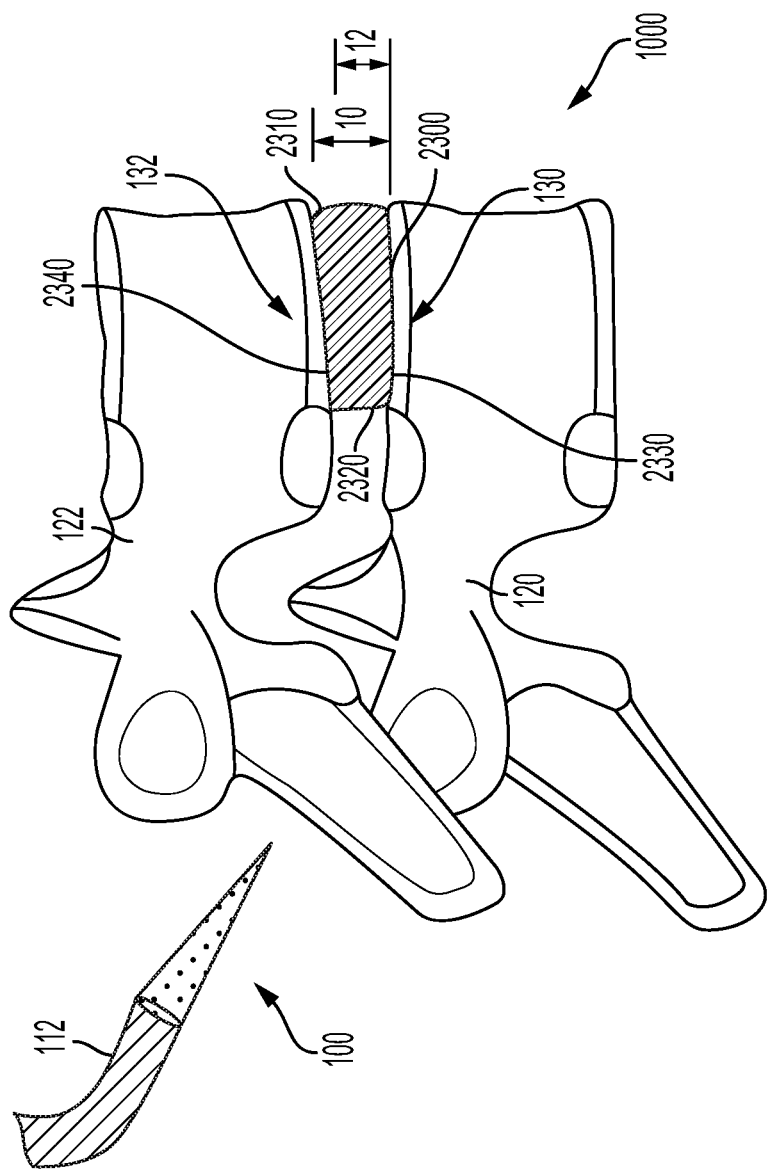
FIG. 23 is a lateral view of the first additive in-situ implant formed in-situ adjacent the first patient vertebra and a second, adjacent, vertebra.

FIG. 23 is a lateral view of the first in-situ-grown or formed implant 2300 formed adjacent the first patient vertebra 120 and a second, adjacent, vertebra 122.

The implant 2300 is grown or formed in-situ to extend from an anterior, end 2310 to a posterior, end 2320, and from an inferior end, or base, 2330 to a superior end, or top 2340. The implant 2300 can be printed in-situ to have any desired configuration (e.g., size, geometry), to accomplish needed bodily adjustment, or tissue-position maintenance, during and after the procedure. In the example shown, the in-situ-grown or formed implant 2300 is created to have a height that tapers generally from a maximum anterior height 10 to a minimum posterior height 12.

Figure 36:
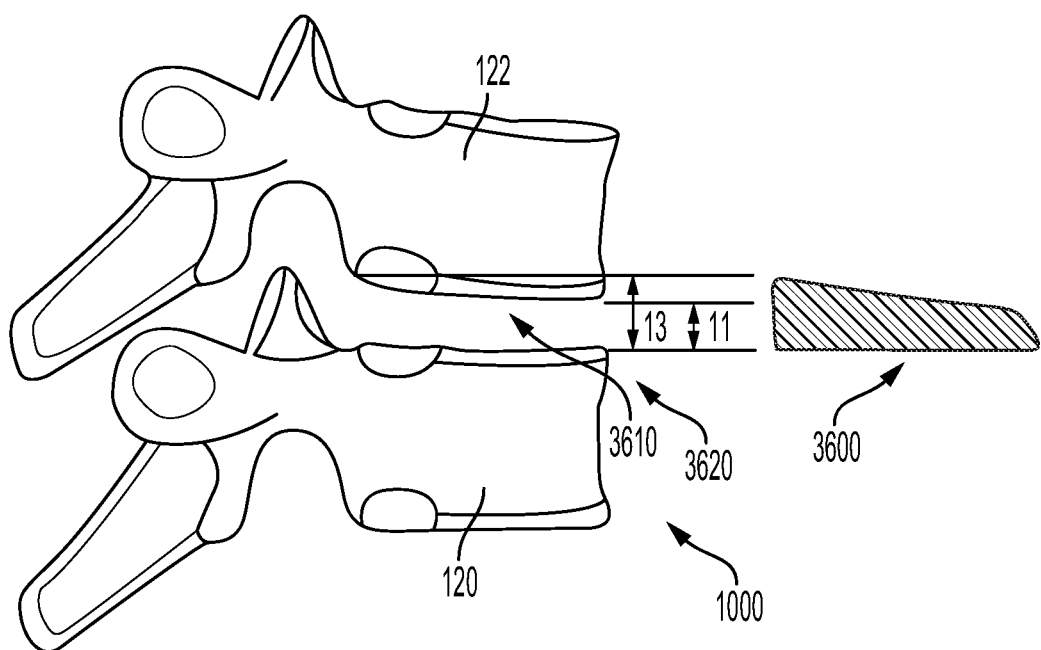
FIG. 36 is a side view of two adjacent patient vertebrae spaced such that an illustrated interbody implant cannot be readily passed to a desired inter-vertebral position.

The height is in various embodiments tapered in the other direction (down from a maximum posterior end), as shown in FIG. 23, not consistently tapered (e.g., tapered in one or more portions, but not across the entirety, and perhaps not in the same directly), or not tapered. Counter tapering (down from a maximum posterior) can be useful, for instance, when the patient anatomy or surgical strategy calls for a larger posterior portion, as shown needed in the case of FIG. 36. FIG. 36 is described further below.

In the present embodiment, and for any of the embodiments provided, geometry of the in-situ-grown or formed implant 2300 could have any features beneficial for encouraging bone growth on, through, around, or adjacent the implant. In contemplated embodiments, the material may include or be coated with any beneficial material. Example materials include medicinal material, antibiotic material, and bacteria- or virus-resistant or -fighting materials. Materials could be introduced by the dispensing component 110, as discussed above, or another nozzle or dispensing component.

Implant 2300 geometry may be shaped to avoid any remaining bony structures present, such as may occur in a partial osteotomy procedure. In a contemplated embodiment, the printing material includes material configured to affect patient tissue.

Implant 2300 geometry may include features that facilitate surgery, such as those that can be used as drill guides or for anatomical holding. As an example of the latter (anatomical holding), the implant 2300 could be shaped to (a) hold back or move a dura of the patient 1000, (b) shield exiting nerve roots, or (c) block any blood vessel from being injured in surgery. (dura, roots, and vessels not shown in detail) The facilitating features can be temporary, by being removable after they have served their purpose, which can be prior to an end of the printing steps or any time before an end of the procedure.

In various embodiments, the system controller 1050 controls other system 100 components to form an implant having geometry corresponding with patient anatomy. The controller 1050 can do this by, for instance, controlling the robotics 1030 and pumps 1040 to form implant pockets or recesses in the implant being formed. Such features can align with, or be offset from, actual patient anatomy, for instance. This may help avoid or limit unwanted implant/anatomy contact. As another potential benefit, printing the implant to have such anatomy-related, or anatomy-customized, features may allow formation of preferred wall thickness or other sizing for the implant, while still allowing the implant to fit in the desired location within the patient 1000.

Figure 24:
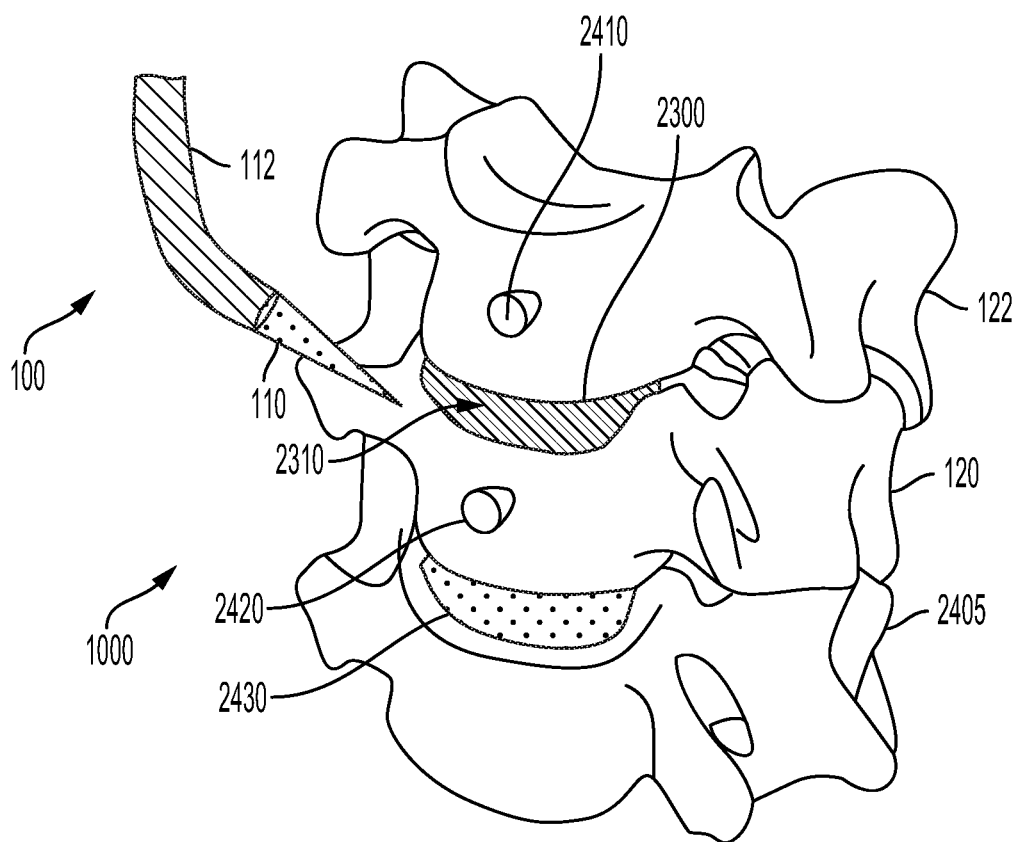
FIG. 24 is a perspective view showing the dispensing component in another in-situ position according to a second general embodiment of the present technology, which can be effected following execution of the first general embodiment.

FIG. 24 is a perspective view showing the dispensing component 110 in another in-situ position adjacent the vertebrae 120, 122 of the patient 1000 according to a second general embodiment. A native intervertebral disc of the patient, between the first vertebra 120 and a further inferior vertebra 2430, is indicated by reference numeral 2430.

The second general embodiment can include, or be effected following execution of, performance of the steps under the first general embodiment described above in connection with FIGS. 11-23. The dispensing component 110 can print the interbody 2300 from a posterior approach and/or an anterior approach. The component 110 can be moved from a completing step of dispensing from a posterior approach, to an anterior approach to commence or continue printing the plate component 2500 (FIGS. 25-28), for instance.

In a contemplated embodiment, the interbody between the patient vertebrae 120, 122 is not in-situ printed or not fully in-situ printed (see, e.g., the embodiment described below in connection with FIGS. 41-44). The interbody there can be pre-manufactured, at a manufacturing facility, for instance.

It should be appreciated that, as with the other in-situ-grown or formed implants described herein, the resulting implant 2300 of this embodiment is highly customized to the patient anatomy, being formed adjacent and on or at patient tissue, including but not limited to the vertebrae 120, 122 in primary examples.

The implant 2300 of this embodiment, or any embodiment herein, can also include interface features to promote printing-material-to-tissue adhesion and/or connection, and/or strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

FIG. 24 shows an implant in place, such as the in-situ-grown or formed interbody of FIG. 23. The figure also shows anchoring components 2410, 2420 affixed to respective anterior faces of the superior and anterior vertebrae 122, 120 of the patient 1000. An example anchoring component, or anchor, is a bone screw. In some embodiments, the anchors include any type of bone screw used conventionally in spinal surgeries. In a contemplated embodiment, the anchor 2410, 2420 is customized to facilitate the implant growing or implant qualities (e.g., shape, strength).

In various embodiments, the anchors 2410, 2420 are printed in place. The technique includes pre-forming bores in the anterior face of the vertebrae 122, 120, and growing the anchors therein, and therefrom.

In one embodiment, the anchors are mechanically driven or forced (i.e., by force, twisting, or the like, versus printing) into the bone, such as by use of a driver instrument. The anchor can be a metal screw, for instance. The anchors can be driven or forced by system components (not shown in detail), such as an anchor driver connected to an end of the robotics armature, with, or in a modular embodiment, as a driver end effector selectively instead of the dispensing component being in this case a readily removable end effector.

It is contemplated that boring equipment (not shown in detail) for this purpose can be part of the system 100. One or more boring end effectors can be attached to the robotics armature, such as an additional effector with the nozzles in the views of FIGS. 2-9. Or the boring end effector can be connected to the armature selectively, as can in some embodiments the dispensing componentry, as described above. The boring equipment can be part of the kits mentioned above. For purposes of illustration, the boring equipment, whether modular, is considered illustrated by the end effector 110 of FIG. 24.

Figure 25:
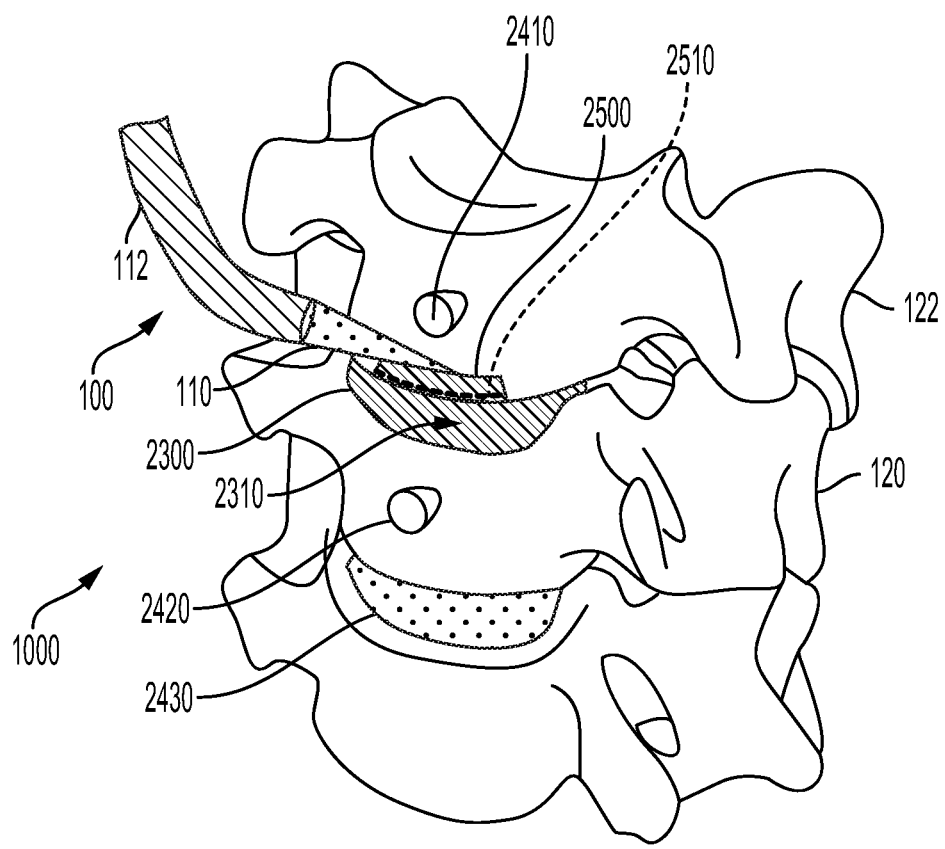
FIG. 25 shows commencement of in-situ formation of second, additional, additive implant, in the form of an inter-vertebrae plate, at a second in-situ position connected to the first additive in-situ implant, and at the second vertebra of the patient according to the second general embodiment of the present technology.

FIG. 25 shows commencement of in-situ formation of second, additional, additive implant, in the form of an inter-vertebrae plate at a second in-situ position connected to the first additive in-situ implant and at the second vertebra of the patient according to the second general embodiment of the present technology. While FIG. 25 is referenced as a commencement of formation, actual commencement can be earlier, depending on the implementation. If the interbody 2310 is printed first, that printing can be considered the commencement, or if the first in-situ printing involves growing the bone anchors 2410, 2420, that printing can be considered the commencement.

The additional in-situ-printed implant formation is indicated by numeral 2500. The extra-interbody portion can be referred to by any of a variety of terms, such as plate, surface portion, or surface connector.

In a contemplated embodiment, the pre-formed or pre-existing implant 2300 includes one or more connecting features at an interface 2510 to which the additional in-situ-printed implant 2300 is formed or connects. The connecting interface 2510 is indicated schematically by lead line in FIG. 25 at a corner formed between the additional in-situ-printed implant 2500 and the pre-implanted interbody 2300. The connecting interface 2510 however can be at any one or more location where the additional in-situ-printed implant 2500 is formed in contact with the pre-implanted interbody 2300. Example interface-feature locations include, for instance, the face 2310 of the interbody 2300, a front-top edge of the interbody, and a front-bottom edge of the interbody.

In various, embodiments, the interbody/plate combination is built in the same surgical procedure, or the combination can be created by printing one of the two in a first procedure and the other in connection with the first in a second surgery, such as on a distinct day, month, or year from the first procedure.

The first-built implant (e.g., the interbody 2300), can be used as a guide for creating the second (e.g., plate 2500) intimately connected to the first and patient tissue (e.g., bone), whether the two are built in the same or distinct surgeries.

Interface features 2310 can include any of protrusions, roughening, indentations, grooves, hooks, overhanding or underhanging elements, the like, or other, to facilitate robust connection between the interbody 2300 and the additional in-situ-printed implant 2500 being formed in connection to the interbody 2300.

And as in other embodiments described herein, robust fixation between the interbody portion and the patient tissue 120, 122, and between the plate portion and the patient tissue, from printing in-situ, customized to and directly to patient anatomy, can be enhanced by preparing the tissue as desired, such as by roughening or grooving.

Figure 26:
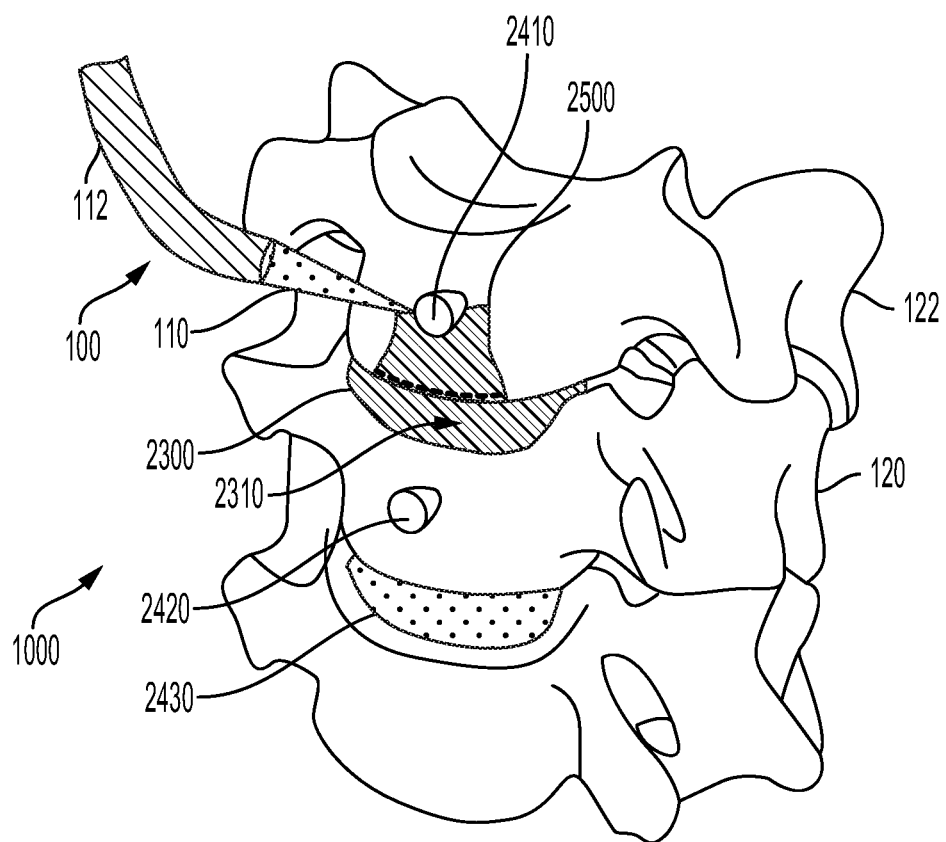
FIG. 26 shows continuation of forming the second additive in-situ implant, including forming the second implant around and in contact with a first bone anchor pre-secured to the second vertebra of the patient according to the second general embodiment of the present technology.

FIG. 26 shows continued formation of the second additive in-situ implant 2500, including forming the second implant around and in contact with the first bone anchor 2410. The in-situ printing may include any of the techniques described herein, including printing with only one material, or printing with two materials.

In one of the mentioned embodiments, in which the bone anchor 2410 is printed, the anchor 2410 can be printed in this step, before or with printing of a body of the adjacent additional in-situ-printed implant 2500. The same is possible in connection with the second bone anchor 2420, also shown in FIG. 26 and described further below in connection with FIG. 28.

Figure 27:
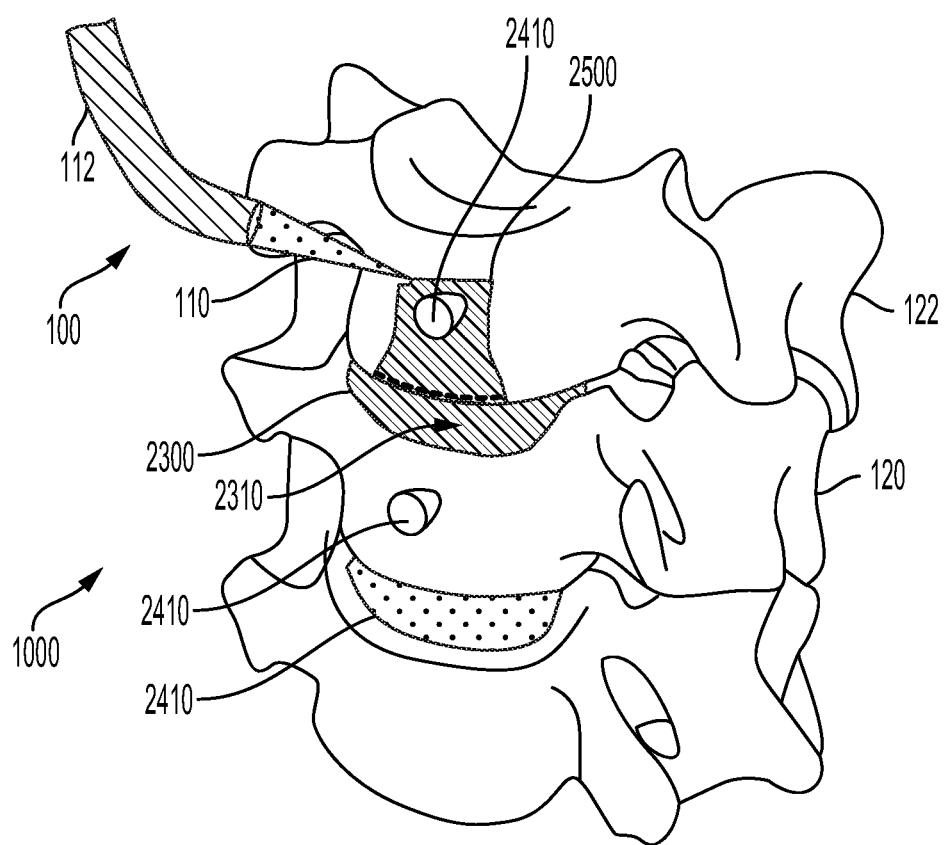
FIG. 27 shows continuation of forming the second additive in-situ implant at the second vertebra according to the second general embodiment of the present technology.

FIG. 27 shows continued formation of the second additive in-situ implant 2500 at the second vertebra 122 of the patient 100 according to the second general embodiment of the present technology.

Figure 28:
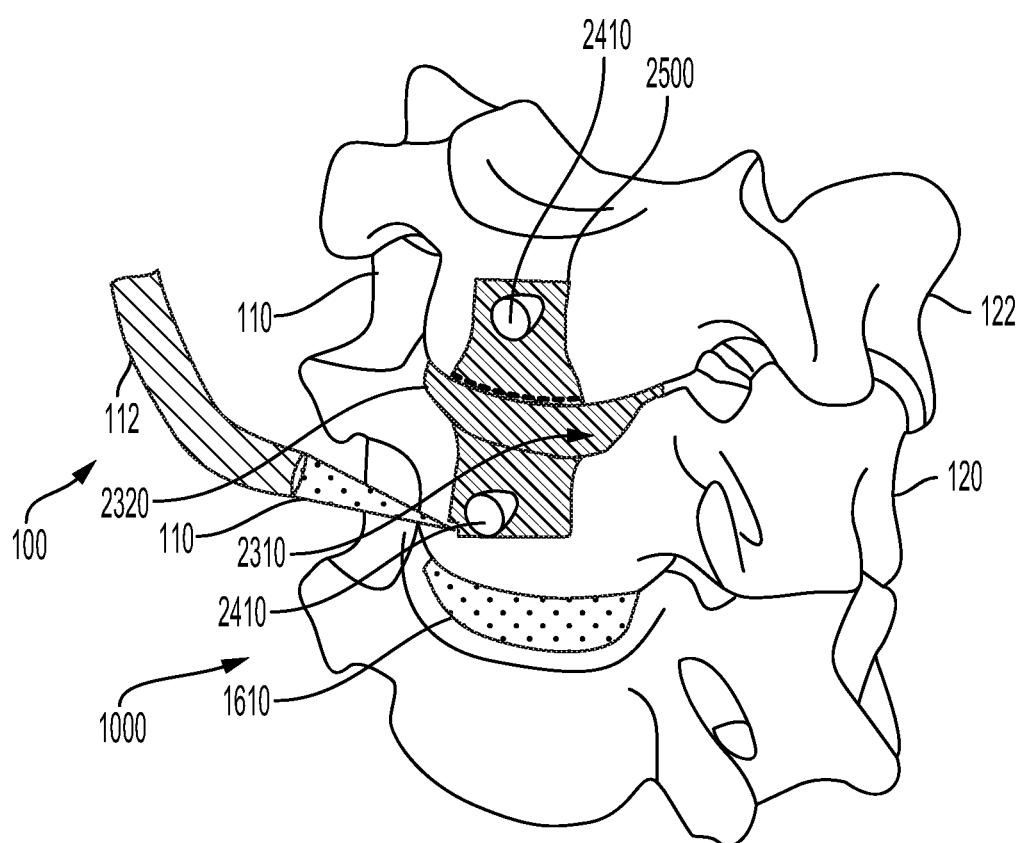
FIG. 28 shows completing of the second additive in-situ implant at the first vertebra of the patient, including forming the second implant around and in contact with a second bone anchor pre-secured to the first vertebra of the patient according to the second general embodiment of the present technology.

FIG. 28 shows completing steps of forming the second additive in-situ implant 2500 at the first vertebra 120 of the patient 100, including forming the second implantsnuggly around a second bone anchor 2420 affixed to the first vertebra, according to the second general embodiment of the present technology.

The system 100 moves and prints the additional in-situ printed implant 2500 in various embodiments to have any desired dimensions—e.g., thickness, height, width, and shape.

It should be appreciated that, as with the other in-situ-grown or formed implants described herein, the resulting implant 2500 of this embodiment is highly customized to the patient anatomy, being formed adjacent and on or at patient tissue, including but not limited to the vertebrae 120, 122 in this example.

The implant 2500 of this embodiment, or any embodiment herein, can also include interface features to promote printing-material-to-tissue adhesion and/or connection, and/or strengthen the implant. Example interface features include surface roughening, surface shaping (e.g., teeth), and surface coating. The interface features can include, for instance, eyelets on the plate for receiving bone anchors (e.g., screws), if not pre-anchored FIGS. 29-33 show another technique for forming an interbody implant by in-situ printing. The implant can also be formed to include a plate portion, as shown in FIG. 33.

Figure 29:
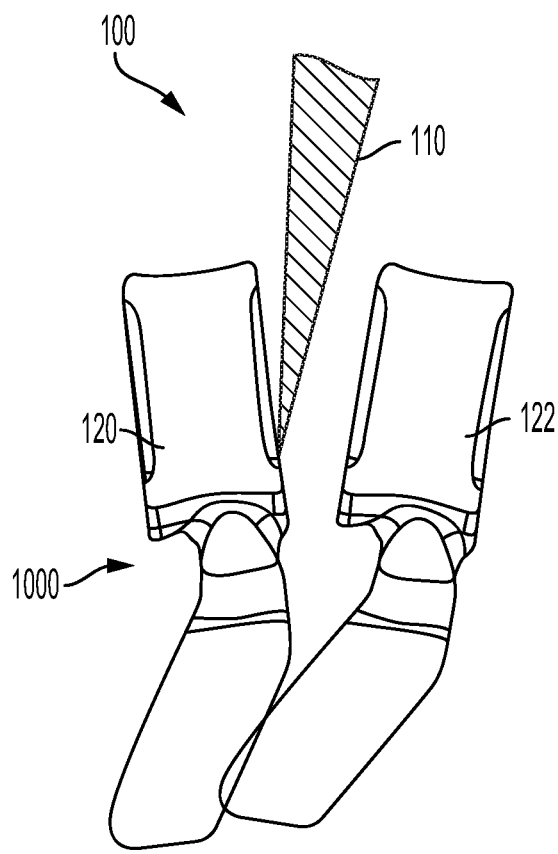
FIG. 29 is a lateral view of the dispensing component of the additive-manufacturing system positioned at an example starting position adjacent patient vertebrae according to a third general embodiment of the present disclosure.

Starting with FIG. 29, a lateral view is provided, of the dispensing component 1010 of the additive-manufacturing system 100 positioned at an example starting position adjacent the vertebrae 120, 122 of the patient 1000, according to a third general embodiment of the present disclosure.

Figure 30:
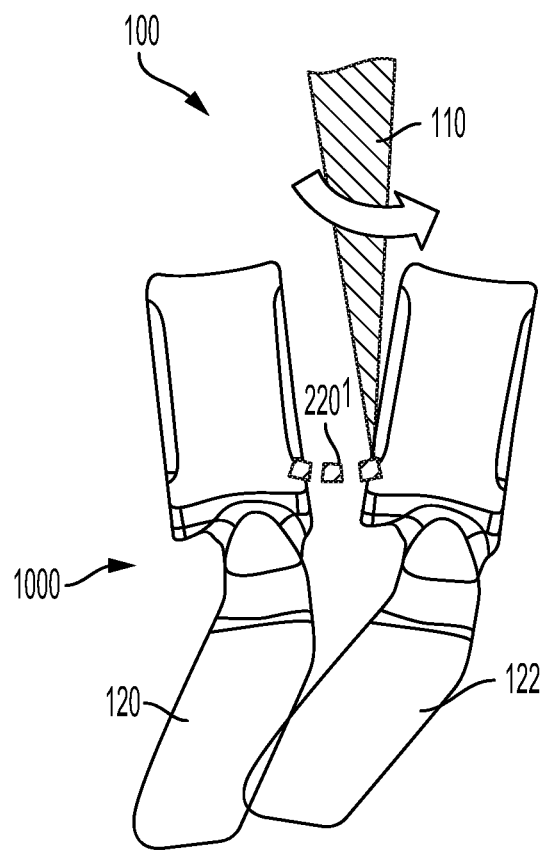
FIG. 30 is a lateral view of the dispensing component starting to dispense substrate material between the patient vertebrae according to the third general embodiment of the present disclosure.

FIG. 30 shows the dispensing component 110 starting to dispense substrate material $220^1$ between the patient vertebrae 120, 122 according to the third general embodiment of the present disclosure.

Figure 31:
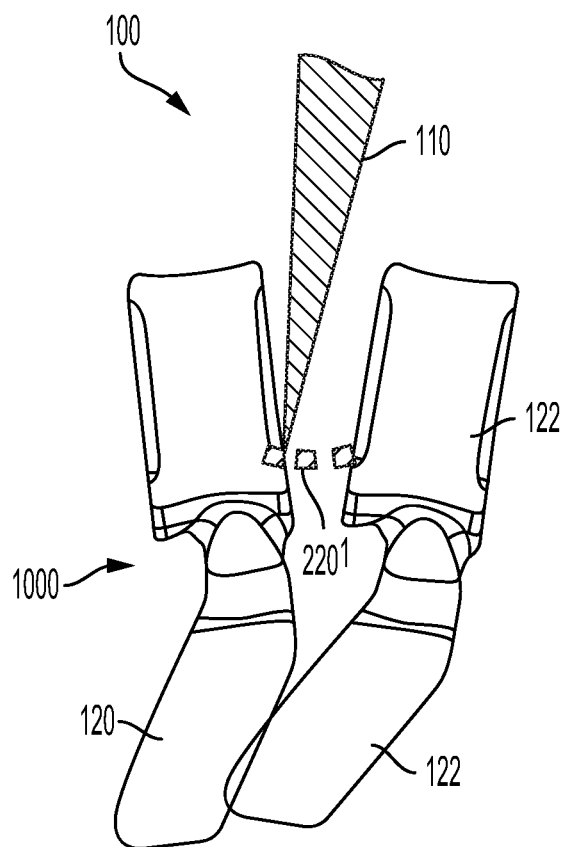
FIG. 31 is a lateral view of the dispensing component repositioned to generally the starting position for commencing depositing of catalyst according between the patient vertebra according to the third general embodiment.

FIG. 31 shows the dispensing component 110 repositioned to or adjacent the starting position (FIG. 29) for commencing dispensing of the second, catalyst, material $220^2$, according between the patient vertebrae 120, 122 according to the third general embodiment.

Figure 32:
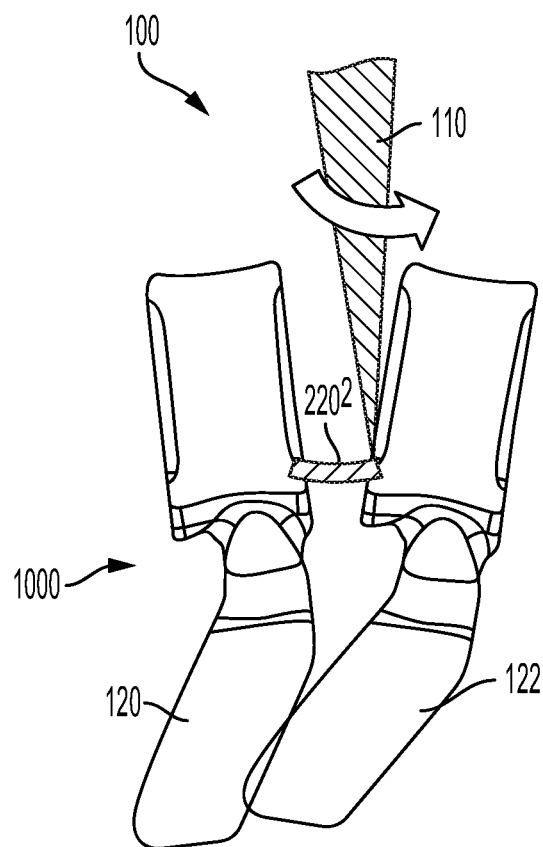
FIG. 32 is a lateral view of the dispensing component dispensing catalyst between the patient vertebra according to the third general embodiment.
Figure 33:
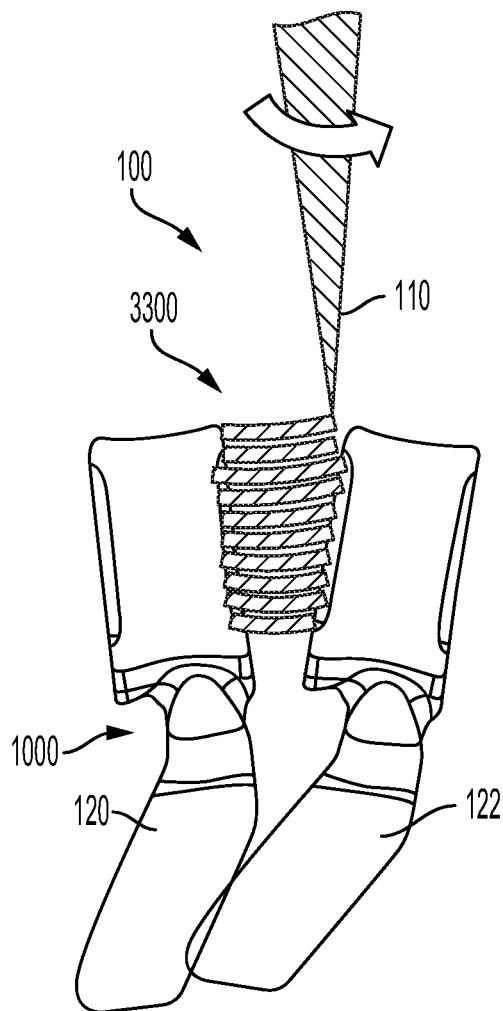
FIG. 33 is a lateral view of the dispensing component continuing to dispense printing material (e.g., substrate and adhesive) between the patient vertebra for forming the interbody implant in-situ according to the third general embodiment.

FIG. 32 shows the dispensing component 110 dispensing catalyst material $220^2$ to, on, or at the substrate material $220^1$, between the patient vertebrae 120, 122.

FIG. 33 is a lateral view of the dispensing component completing printing of material for forming the in-situ-printed implant 3300, according to the third general embodiment.

It should be appreciated that, as with the other in-situ-grown or formed implants described herein, the resulting implant 3300 of this embodiment is highly customized to the patient anatomy, being formed adjacent and on or at patient tissue, including but not limited to the vertebrae 120, 122 in this example.

Figure 34:
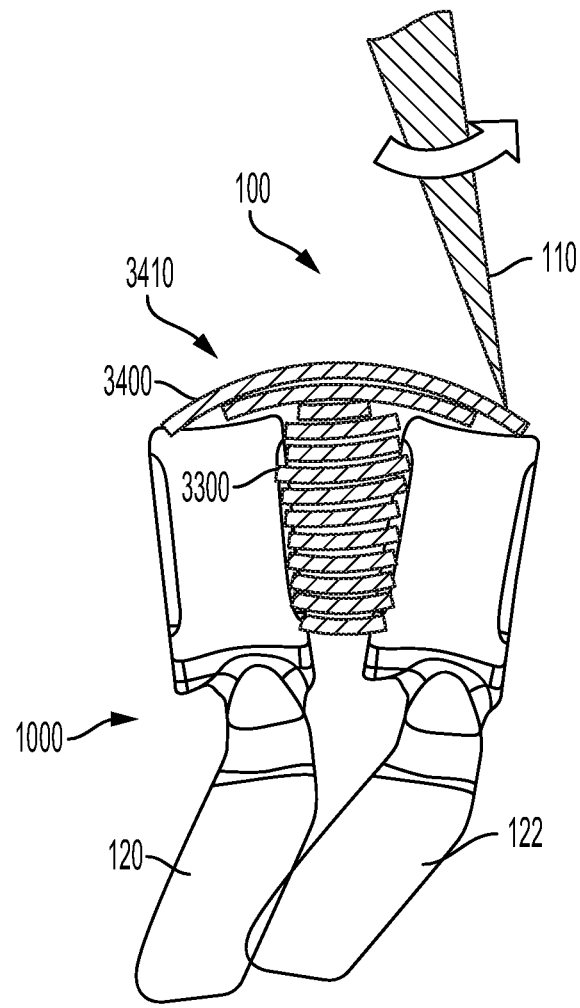
FIG. 34 is a lateral view of the dispensing component continuing to deposit substrate and catalyst, adjacent the interbody portion and the vertebrae to form a facial plate portion connected to the interbody portion, forming in-situ a combined interbody/plate implant according to the third general embodiment.

FIG. 34 is a lateral view of the dispensing component 110 continuing to dispense substrate $220^1$ and catalyst $220^2$, adjacent the previously in-situ grown or formed interbody 3300, and adjacent and in contact with the vertebrae 120, 122 of the patient 1000 to form a facial-plate portion 3400 connected to the interbody portion 3300, thereby printing in-situ a combined interbody/plate implant 3410, according to the third general embodiment.

While the term facial is used, the term is not limiting for all embodiments. The extra-interbody portion, formed outside of the interbody space and in connection with an exterior surface of at least two vertebrae. The extra-interbody portion can be referred to by any of a variety of terms, such as plate, surface portion, or surface connector.

The plate portion can be referred to by any of a variety of terms, such as plate, surface portion, or surface connector.

As in other embodiments described herein, robust fixation between the interbody portion 3300 and the patient tissue 120, 122, and between the plate portion and the patient tissue, from printing in-situ, customized to and directly to patient anatomy, can be enhanced by preparing the tissue as desired, such as by roughening or grooving.

And, as also described in connection with other embodiments, herein, either or both of two connecting implants 3300, 3400, or portions 3300, 3400 of the implant 3410 can be formed to include interface features 2310, such as protrusions, roughening, indentations, grooves, hooks, overhanding or underhanging elements, the like, or other, to facilitate robust connection between them.

The implant 3400 of this embodiment, or any embodiment herein, can also include interface features to promote printing-material-to-tissue adhesion, and/or strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

Figure 35:
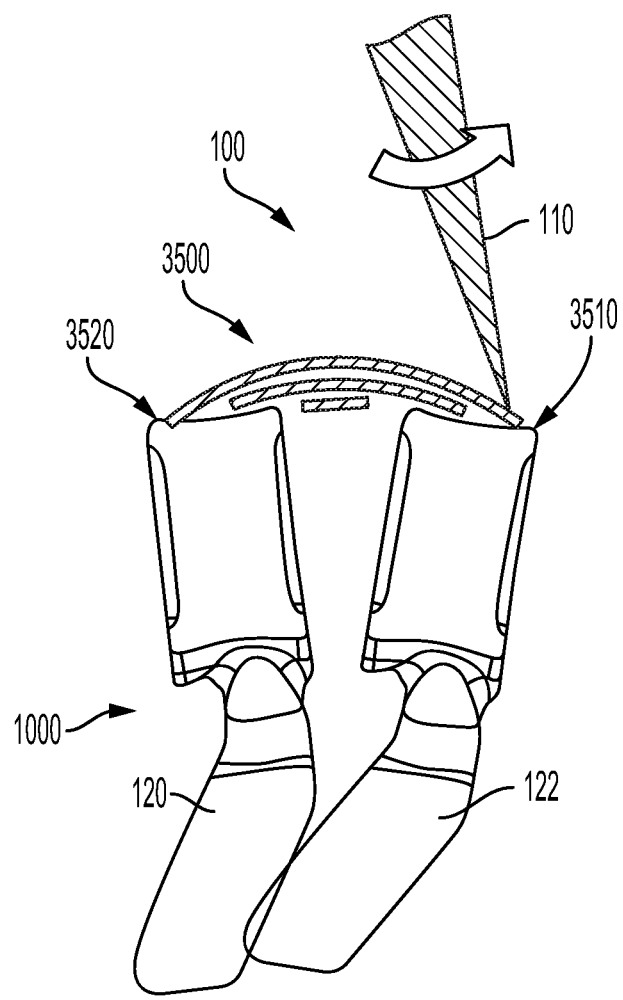
FIG. 35 is a lateral view of the dispensing component depositing printing material facially to and between the vertebrae forming in-situ a plate implant fixing the vertebrae together, according to a fourth general embodiment of the present technology.

FIG. 35 is a lateral view of the dispensing component 110 positioned by the robotics 1030 and armature 112 of the system 100 for dispensing. The system 100 by way of the dispensing component 110 deposits printing material (e.g., substrate and catalyst) to, or to and between, faces 3510, 3520 of the vertebrae 120, 122 forming in-situ a plate implant 3500 fixing the vertebrae together, according to a fourth general embodiment of the present technology.

The embodiment can include pre-implantation, or in-situ printing of bone anchors (not shown in FIG. 35) to which the plate implant 3500 is grown or formed. Anchor pre-implantation and printing is described above with the embodiment of FIG. 26.

It should be appreciated that, as with the other in-situ-grown or formed implants described herein, the resulting implant 3500 of this embodiment is highly customized to the patient anatomy, being formed adjacent and on or at patient tissue, including but not limited to the vertebrae 120, 122 in this example.

And as in other embodiments described, robust fixation between the between the in-situ-grown or formed plate 3500 and the patient tissue, from printing in-situ, customized to and directly to patient anatomy, can be enhanced by preparing the tissue as desired, such as by roughening or grooving.

And the implant 3500 of this embodiment, or any embodiment herein, can also include interface features to promote printing-material-to-tissue adhesion and/or connection, and strengthen the implant. Example interface features include surface roughening, surface shaping (e.g., teeth) and surface coating.

Some embodiments address issues related to challenging patient-tissue spacing. Sometimes an entry opening to a target implant region of the patient 100 is too small to fit a pre-made implant through. Various techniques of the present disclosure described above can be used to remedy these situations. As other example solutions, FIGS. 37-40 show a manner of doing so, and FIGS. 41-44 shows another.

As an example of such fitting challenge, FIG. 36 shows a side view of the patient vertebrae 120, 122 spaced such that a pre-printed or otherwise pre-made interbody implant 3600, sized for a particular interbody space 3610, cannot be readily passed to position in the space. Anterior interbody spacing 11, at an opening 3620, of the patient 1000 is smaller than an entry height 13 of the implant 3600.

Figure 37:
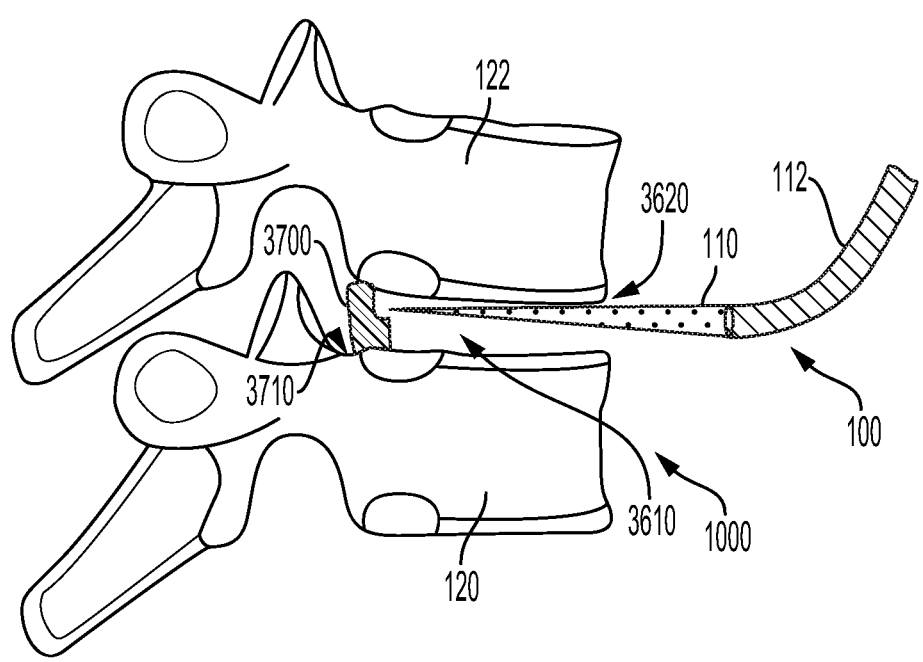
FIG. 37 shows commencement of in-situ formation of a sixth interbody implant according to a sixth general embodiment of the present technology.

As a first of the mentioned solutions for the challenge presented by context of FIG. 36, FIG. 37 shows commencement of in-situ formation of a fifth interbody implant 3700 according to a fifth general embodiment of the present technology.

The dispensing component 110 is sized, shaped, and maneuvered to easily fit through the anterior opening 3620 of FIG. 36, and extend into the inter-tissue space 3610 and to a posterior region 3710 between the vertebrae 120, 122.

Figure 38:
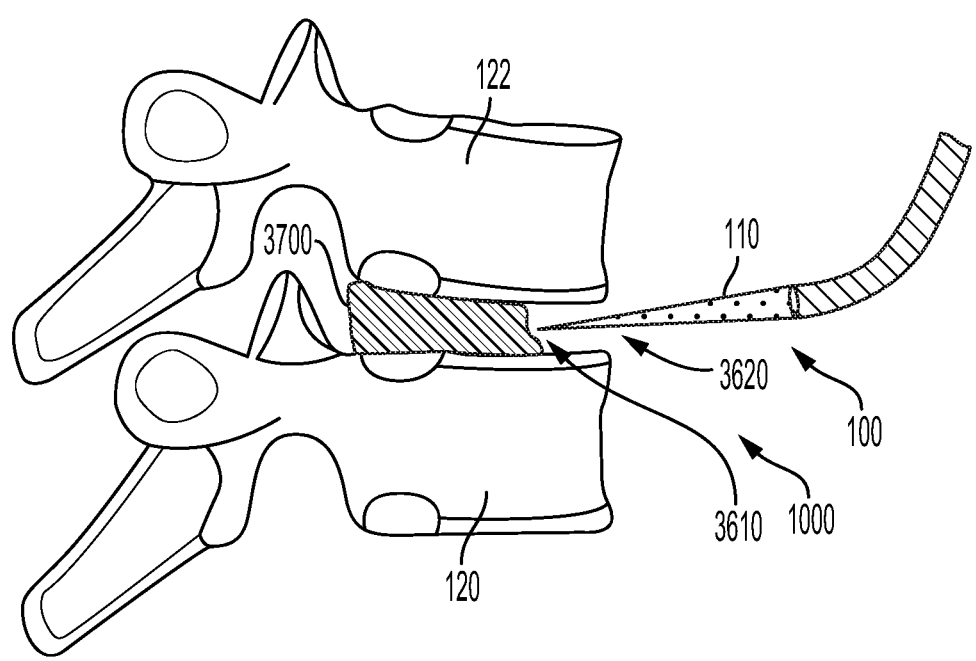
FIG. 38 shows continued in-situ formation of the sixth interbody implant.

FIG. 38 shows continued in-situ formation of the fifth interbody implant 3700, posterior-to-anterior by way of example.

Figure 39:
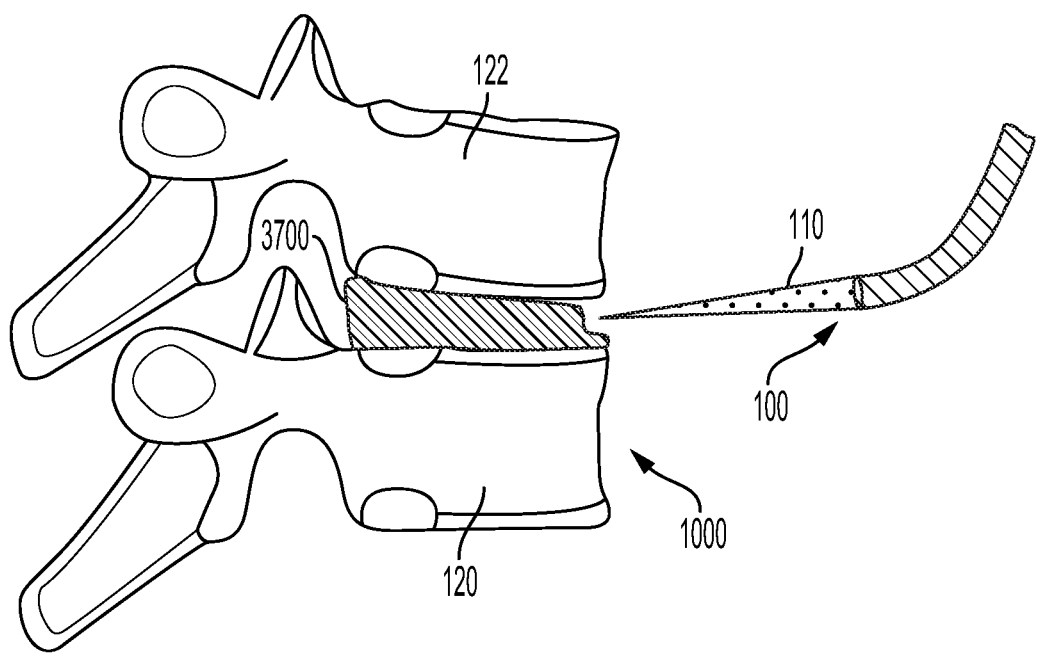
FIG. 39 shows final in-situ steps for forming the sixth interbody implant.

FIG. 39 shows final in-situ steps completing for forming the fifth interbody implant 3700.

Figure 40:
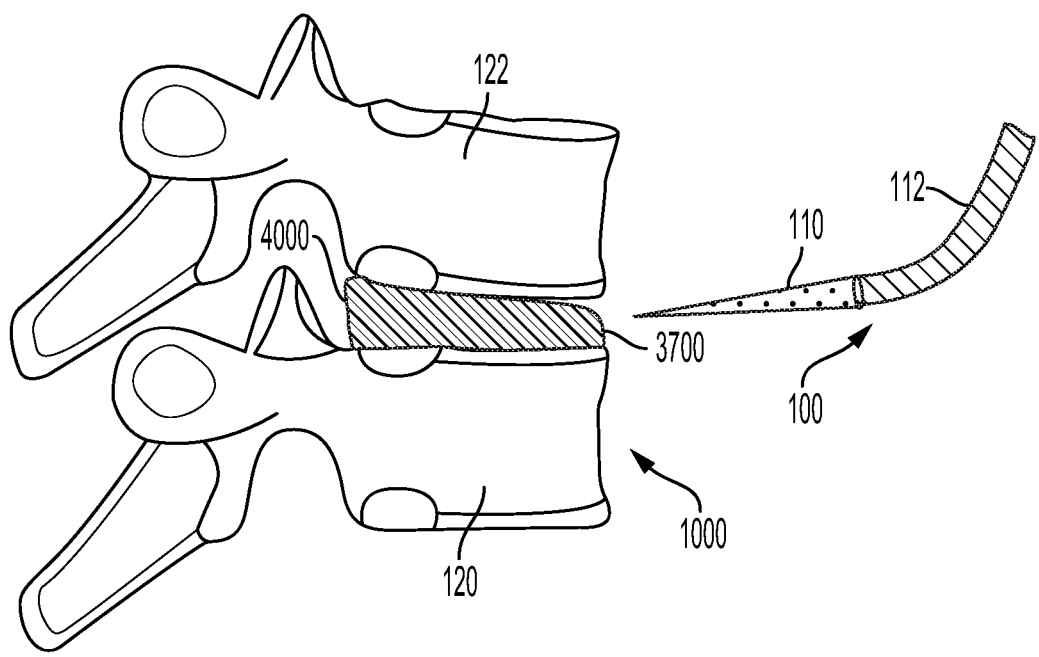
FIG. 40 shows the fourth in-situ-formed interbody completed in the patient according to the sixth general embodiment.

FIG. 40 shows the in-situ-grown or formed interbody 3700 completed in the patient 1000 according to the fifth general embodiment.

As in other embodiments described herein, the robust fixation between the interbody portion and the patient tissue 120, 122, and between the in-situ-grown or formed implant 3700 and the patient tissue 120, 122, from printing in-situ, customized to and directly to patient anatomy, can be enhanced by preparing the tissue as desired, such as by roughening or grooving.

It should be appreciated that, as with the other in-situ-grown or formed implants described herein, the resulting implant 3700 of this embodiment is highly customized to the patient anatomy, being formed adjacent and on or at patient tissue, including but not limited to the vertebrae 120, 122 in this example.

The implant 3700 of this embodiment, or any embodiment herein, can also include interface features to promote printing-material-to-anchor adhesion and/or connection, and strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

Figure 41:
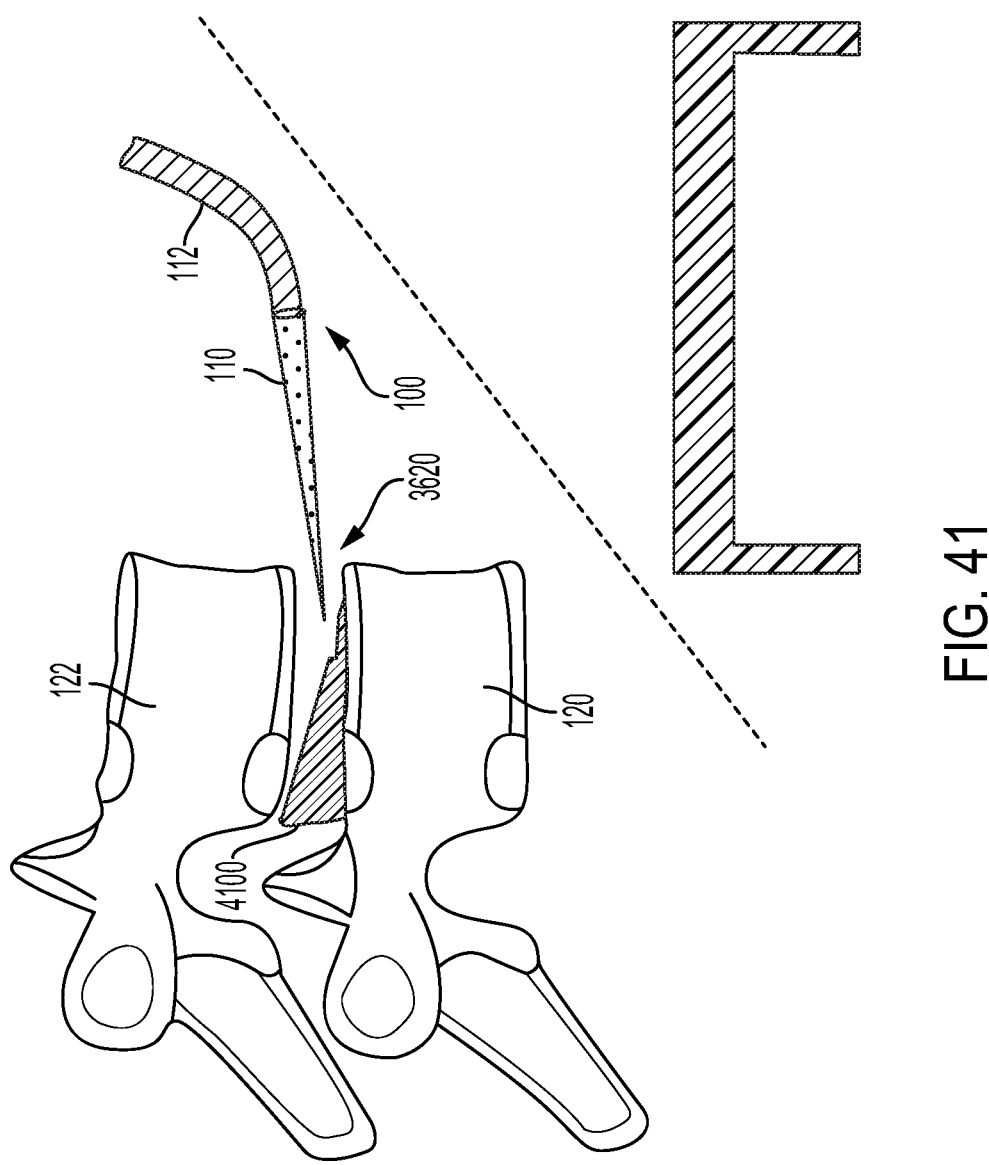
FIG. 41 shows commencement of in-situ formation of a first component of a sixth, multi-component, interbody implant according to a sixth general embodiment.

As another solution to the fit challenges indicated by FIG. 36, FIG. 41 shows commencement of in-situ formation of a first part 4100 of a multi-component, interbody implant, between the vertebrae 120, 122 of the patient 1000, according to a sixth general embodiment.

Figure 42:
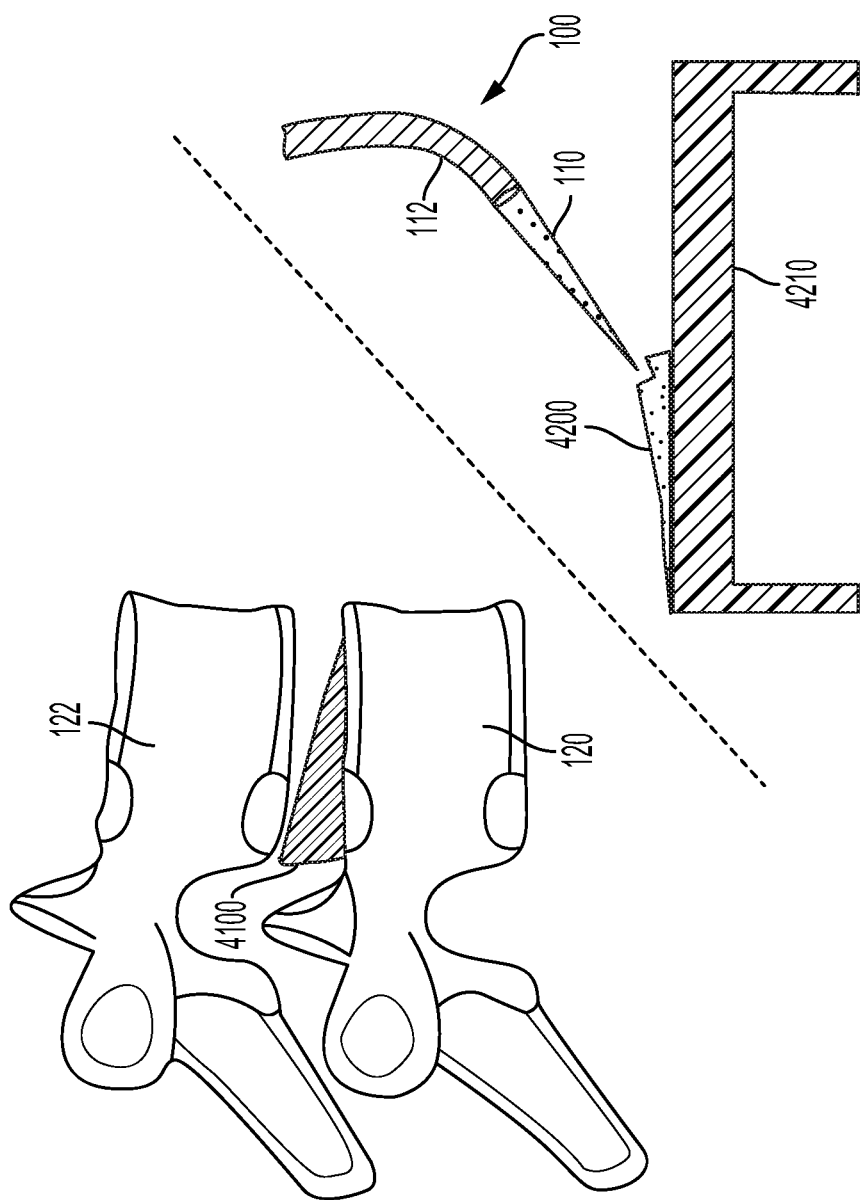
FIG. 42 shows commencement of additive formation of a second component of the sixth, multi-component, interbody implant according to the sixth general embodiment.

FIG. 42 shows commencement of additive formation of a second part 4200 of the multi-component interbody implant according to the sixth general embodiment. The formation is shown schematically on a table 4210, such as a prep table in the surgical room.

In a contemplated embodiment, the surface on which the second part is grown or formed includes a patient-tissue surface, such as an exterior of vertebra or other bone.

Figure 44:
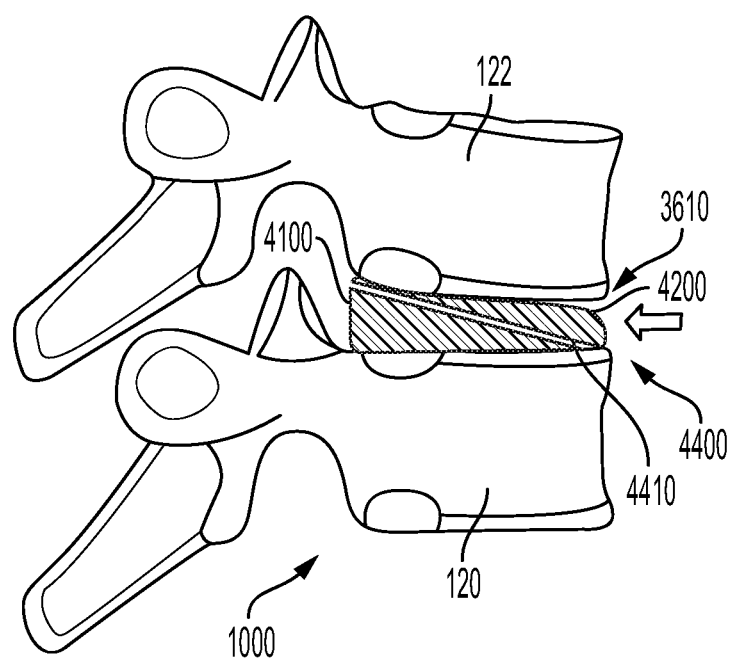
FIG. 44 shows the second component interbody implant having been forced to a desired position directly adjacent the first component, forming the sixth exemplary interbody according to the sixth general embodiment.

In a contemplated embodiment, the second part 4200 is grown or formed at least partially on the first part 4100. The connection between the two may be slight in various ways, to allow ready relative movement between the parts after the second part is completed (such as to accomplish a final, combined, implantshape, such as shown in FIG. 44) The slight connection may be from printing only one or more small pieces, such as tabs, on the first part 4100, and printing the second part on the small pieces.

The second part 4200 can then be easily pushed in a posterior direction, breaking the small pieces, the reach the final implantshape. Another example of a slight connection can be from a manner in which the second part is printed on the first, such as after a top layer of the first part has cured or solidified by an amount sufficient to enable the second part printed thereon to be easily moved relative to the first, thereby again allowing the subsequent relative movement.

The second part is in various embodiments grown or formed real-time by the system 100, as shown, or is a pre-manufactured component, whether printed. In various embodiments, the second part 4200 is made to have a size and shape corresponding to size and shape of the first part 4100 and to patient anatomy, namely the vertebrae 120, 122. Likewise, the first part 4100 is made to have a size and shape corresponding to size and shape of the second part 4200, as well as to the patient anatomy.

Figure 43:
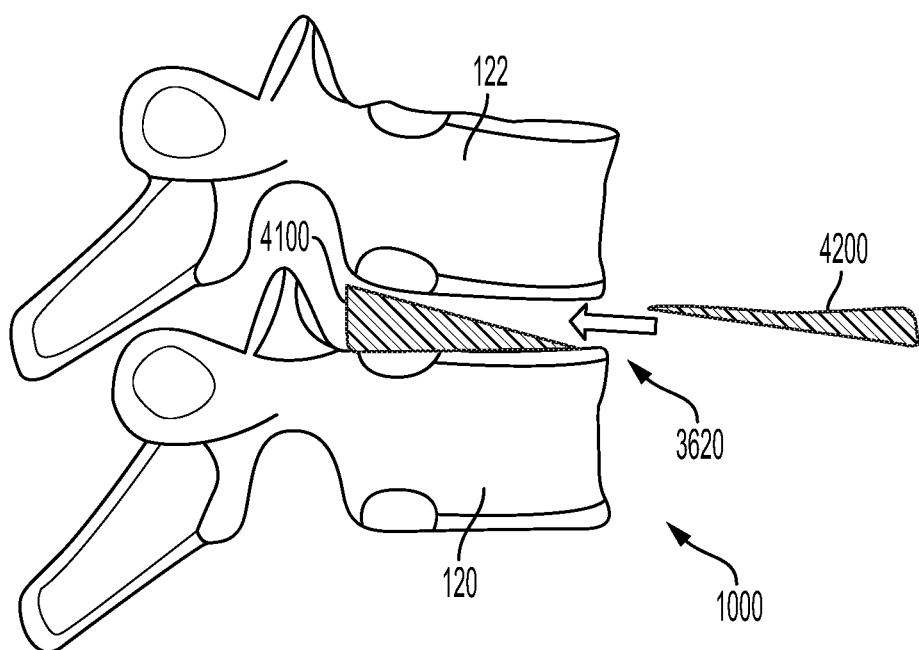
FIG. 43 shows the second component of the sixth embodiment of the interbody implant positioned for insertion to an in-situ position adjacent the first component.

FIG. 43 shows the second part 4200 of the sixth embodiment of the interbody implant positioned for insertion, adjacent the tissue opening 3620.

FIG. 44 shows the second component 4200 forced to a final position shown in FIG. 44 adjacent the first part 4100. The movement may cause the second component 4200 wedge between the first part 4100 and the second vertebra 122, which may slightly push one or both vertebra away from the other. The forcing causes the second part 4200 to, with the first part, substantially fill the inter-tissue space 3610 of the patient 1000 as desired. This forms the multi-component interbody implant in-situ (being grown or formed at least partially in-situ), according to the sixth general embodiment.

In a contemplated embodiment, the system 100 applies or is used to apply the force to move the second part 4200 into place. The dispensing component 110 may be used to apply the force, for instance, by motivation of a surgeon or the robotics 1030 controlled by the system controller 1050.

Spacing between the parts 4100, 4200 can have any size or dimension, desired, or the parts can be formed and connected so that there is no, or substantially no, space between them. Spacing may be desired in some cases, such as to allow relative movement between the parts 4100, 4200 as the patient moves and heals (e.g., inter-vertebral fusing) after the procedure.

Either or both of the parts 4100, 4200 can have interface features, indicated schematically (by location) by reference numeral 4410. Interface features 4410 can include any of protrusions, roughening, indentations, grooves, hooks, overhanding or underhanging elements, the like, or other, to facilitate robust connection between the parts 4100, 4400.

As another example, the parts 4100, 4200 can include matching features that facilitate accurate relative positioning of the two. Or have matching, or geometrically-corresponding, features promoting connection between the two, such as by one being made to have one or more rails and one having one or more corresponding slots to receive the rails. Or, to promote connection between them, and possible to also provide an indication of proper relative positioning, such as by haptic feedback to the system 100 or surgeon maneuvering the second part 4200 into place adjacent the first part 4100.

In various embodiments the second part 4200 can be pre-manufactured. In some cases, the first part 4100 is structured (sized and shaped, for instance) to accommodate (e.g., receive) the second part 4200. The first part 4100 may be grown or formed to have a recess, hollow, void, or other spacing, for instance, to which the second part 4200 can be connected and/or into which the second part 4200 can be placed.

The first part 4100 can be printed after the second part 4200 is implanted. The first part 4100 can be printed in and/or around. The first part 4100, and thus the combination, would thus be patient-anatomy optimized. Another benefit of these embodiments can be time savings, and cost savings from time and perhaps labor and material savings.

The second part when pre-made per these embodiments can have any desired form, including any existing parts for the same or similar purpose—e.g., existing spinal implants. One or more pre-made parts can be included in a set sold or provided to the surgical team.

As in other embodiments described, the robust fixation between the interbody parts 4100, 4200 and the patient tissue 120, 122, and between the resulting in-situ-grown or formed implant 4400 and the patient tissue 120, 122, from printing in-situ, customized to and directly to patient anatomy, can be enhanced by preparing the tissue as desired, such as by roughening or grooving.

The implant 4400 of this embodiment, or any embodiment herein, can also include interface features to promote printing-material-to-anchor adhesion and/or connection, and strengthen the implant. Example interface features include surface roughening, surface shaping (e.g., teeth), and surface coating, or physical features that penetrate patient tissues, such as bony surfaces, e.g., vertebral bodies, or features for attaching post-printing devices such as eyelets for inserting screws.

It should be appreciated that, as with the other in-situ-grown or formed implants described herein, the resulting implant 4400 of this embodiment is highly customized to the patient anatomy, being formed adjacent and on or at patient tissue, including but not limited to the vertebrae 120, 122 in this example.

Figure 45:
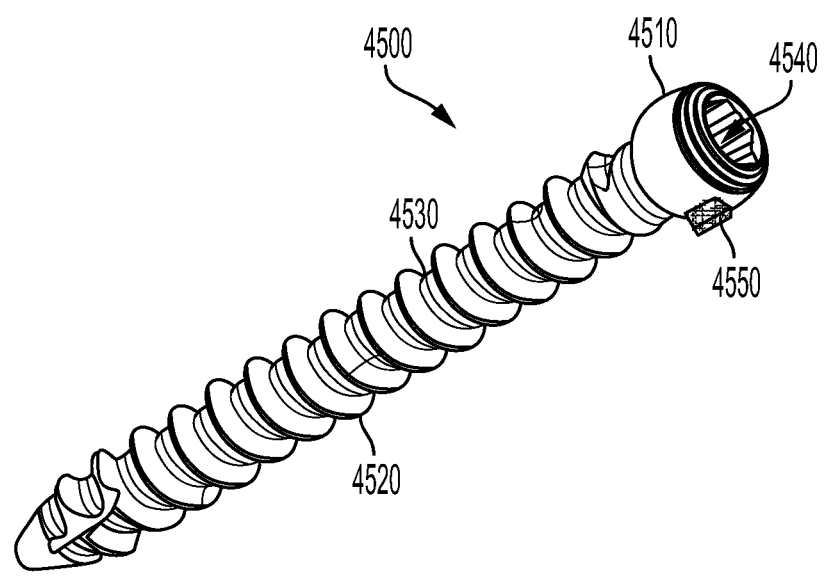
FIG. 45 shows a perspective view of an exemplary fiducial screw according to a seventh general embodiment of the present technology.

Turning to a seventh, general embodiment of the present disclosure, FIG. 45 shows a perspective view of an exemplary fiducial bone anchor implant 4500, such as a bone screw.

The bone anchor 4500 can in various implementations be referred to as a fiducial anchor, or fiducial screw, and a function thereof can include an ability to be visualized readily by scanning or imaging equipment based on a characteristic of the implant.

Example recognition characteristics include shape of features. The anchor 4500 can also include detectable features, whether for recognition in the sense used here. These can be visible, or not visible to the eye. Examples include bar codes, QR codes, RFID tags, ultraviolet inks, and surface or embedded markers. Markers can include techno-aide (TA) markers, or others having one or more select materials that look or scan/image in a unique way for anchor identification, anchor or anchor-portion recognition, position determination, or orientation determination.

In a contemplated embodiment, the recognition features include a material of the implant.

An example of the mentioned scanning or imaging equipment is the surround scanner 1092, or the navigation system 1093, of FIG. 10.

The anchor 4500 includes a head 4510, a shaft 4520, and at least one thread 4530 for fixing the implant to bone. The head 4510 includes driving features 4540 in various embodiments. The driving features are configured to be engaged by a driver instrument (not shown). An example driving feature is a hex shape, as shown in FIG. 45.

Any aspect of the anchor implant 4500 can have the fiducial, readily recognizable characteristic(s). The head 4510 is an example. The head 4510 can have any of a variety of unique, or special, fiducial shapes or geometries for the fiducial purpose. In various embodiments, the head 4510 is generally ball-shaped.

When having fiducial characteristics, the head 4510 may be referred to as a fiducial head, or fiducial portion of the anchor 4510. The fiducial head 4510 is in various embodiments configured (e.g., fiducially shaped) and/or constituted (having fiducial material, e.g.) to promote ready recognition by scanning or imaging equipment, such as the surround scanner 1092, or the navigation system 1093 sensor.

The head shape can be unique, or special, by being distinct from conventional screw head shapes, for instance. And the processor of the controller 1050, executing the instruction stored in the memory of the computing components 1060, recognizes the distinct shape in the scan data, and with that the position of the head or anchor.

Other portions of the screw, such as the shaft 4520 or the thread 4530 thereon, can also have fiducial features, along with or instead of the head, to be highly fiducial.

More particularly, the fiducial head 4510, or any fiducial component of the anchor 4500, has a specific geometry that software, of the controller 1050 of the system 100 (see e.g., FIG. 10) is programmed to recognize in scanner or image data.

In the case of the fiducial head 4510, an example geometry can be, for instance, conical, cubical, or cylindrical—such as by including, e.g., a cylindrical post.

As another example fiducial geometry, the implant 4500 can have a fiducial characteristic that is not a primary component of the implant, such as the head, shaft or thread of the implant 4500. Such characteristic can be temporary, by being removable after they have served their purpose, which can be prior to an end of the printing steps or any time before an end of the procedure.

An example add-on fiducial characteristic is a protrusion 4550. The add-on features can be formed with or added to the implant 4500, such as by printing by the system, which may also print the entire implant 4500. The protrusion or other fiducial feature can be configured and/or attached to the implant 4500 to be readily removed during the procedure. Removal can include snapping off or pulling off. While surgical staff can effect the removal, in a contemplated embodiment the controller 1050 is configured to, by the processor executing instruction stored in the controller, maneuver an instrument, such as the dispenser 110, to remove the fiducial feature.

The fiducial implant component, such as the fiducial head 4510, or fiducial add-on feature, such as the protrusion 4550, can as mentioned include material especially conducive to visualizing. The material is configured to be especially sensed and/or especially recognized by the scanner/imaging equipment and/or by the software of the controller 1050 receiving the image data. Example scanning techniques include x-ray, MRI, and camera.

The fiducial anchor 4500 in various embodiments includes interface features to promote engagement of in-situ printing material (see e.g., numeral 220 in FIGS. 49-53) to the anchor 450. Interface features can also promote printing-material 220-to-anchor 450 adhesion and/or connection, and strengthen the anchor 4500. Example interface features include surface roughening, surface shaping (e.g., teeth), and a surface coating.

Figure 46:
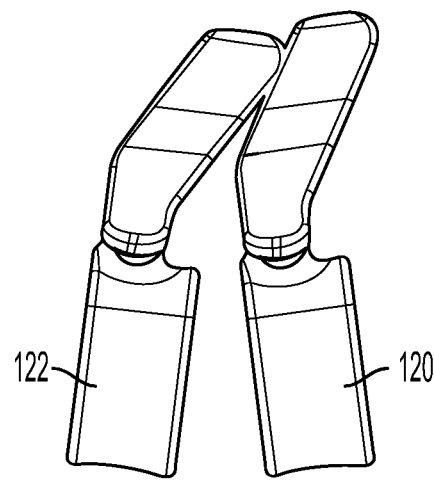
FIG. 46 shows a lateral view of patient vertebrae to be joined.

FIG. 46 shows a lateral view of patient vertebrae 120, 122 to be fused.

Figure 47:
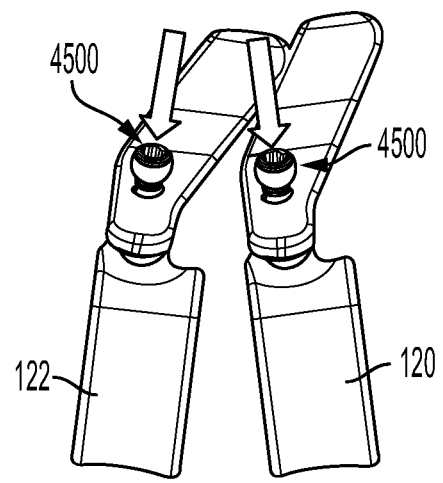
FIG. 47 shows the lateral view of patient vertebrae, each having a fiducial screw of FIG. 45 anchored to an anterior, e.g., pedical, portion thereof.

FIG. 47 shows the lateral view with bone anchors 4500 anchored into an anterior, pedical, portion of the vertebrae 120, 122.

In various embodiments, the anchors 4500 are printed in place. The technique includes pre-forming bores at the anchor locations of the vertebrae 122, 120, and growing the anchors 4500 therein, and therefrom.

In one embodiment, the anchors 4500 are mechanically driven (by threading, twisting, or otherwise forcing the anchor) into the bone, such as by a conventional driver instrument (not shown).

The anchor 4500 can be a metal screw, for instance. The anchors are in various embodiments driven in by system components (not shown in detail), such as an anchor driver connected to an end of the robotics armature 112. The driver end effector, in a modular embodiment, is a driver end effector selectively connected to the armature instead of the dispensing component and is readily removable after use. The desired dispensing end effector 110 is then connected to the armature 112 for the printing steps.

It is contemplated that boring equipment (not shown in detail) for this purpose can also be part of the system 100. One or more boring end effectors can be attached to the robotics armature, such as an additional effector with the nozzles in the views of FIGS. 2-9. Or the boring end effector can be connected to the armature selectively as a removable end effector.

Such additional equipment (driver and boring equipment), whether modular, is considered illustrated by the end effector 110 shown in FIG. 24 to simplify the drawings.

Figure 48:
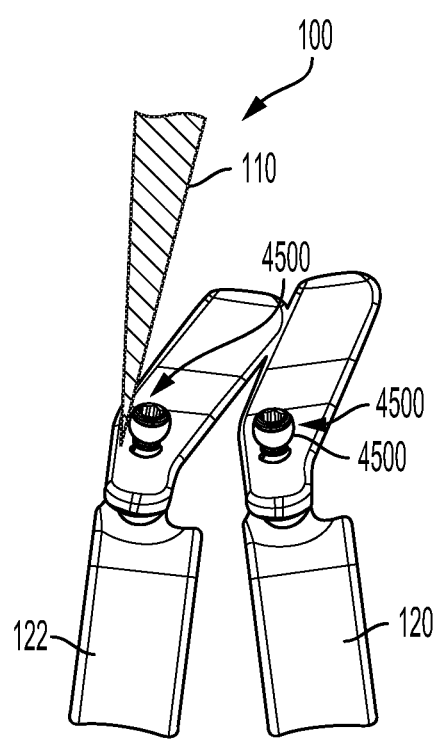
FIG. 48 is a lateral view of the dispensing component of the additive-manufacturing system positioned at an example starting position adjacent one of the fiducial screws, or at least adjacent one of the patient vertebrae, for commencing depositing printing material for growing a fusion implant in-situ, according to the seventh general embodiment of the present disclosure.

FIG. 48 is a lateral view of the dispensing component 110 of the additive-manufacturing system 100 positioned at an example starting position adjacent one of the fiducial screws 4500, or at least adjacent one of the patient vertebrae, for commencing deposit of printing material (e.g., substrate and catalyst) for in-situ printing an implant connecting the vertebrae 120, 122, according to the seventh general embodiment of the present disclosure.

The starting position can be determined by the controller 1050 based on anchor positioning determined by recognition of the fiducial characteristic of the anchor indicated in scan or image data taken prior to the dispensing component 110 positioning. The controller 1050 then controls the robotics componentry 1030 to position the dispensing component 110 accordingly.

In various embodiments, the controller 1050, also for determining the starting position, recognizes patient anatomy adjacent the implant location.

The controller 1050 may incorporate such fiducial implant and/or patient anatomy information into a pre-established in-situ printing plan, or generate the plan based on fiducial implant and/or patient anatomy information.

Figure 49:
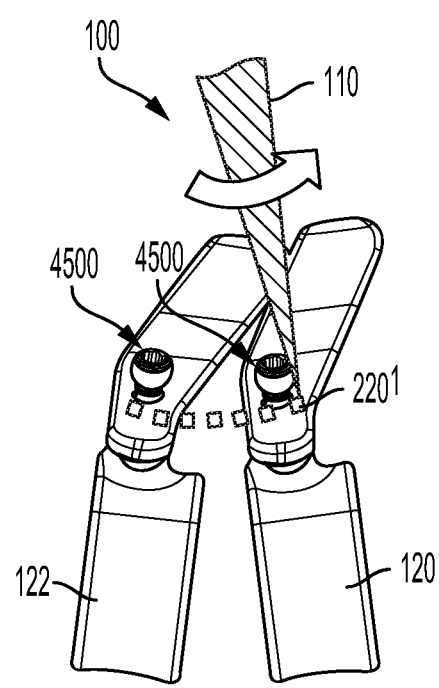
FIG. 49 is a lateral view of the dispensing component of the additive-manufacturing system applying substrate material between the vertebrae for in-situ printing the implant, connecting the screws and thereby the vertebrae, according to the seventh general embodiment of the present disclosure.

FIG. 49 is a lateral view of the dispensing component 110 of the additive-manufacturing system 100 being moved, by the robotics equipment 1030 or surgeon, and depositing substrate material $220^1$ between the vertebrae 120, 122 for in-situ printing the connecting implant, connecting the bone anchors 4500 and thereby the vertebrae.

Figure 50:
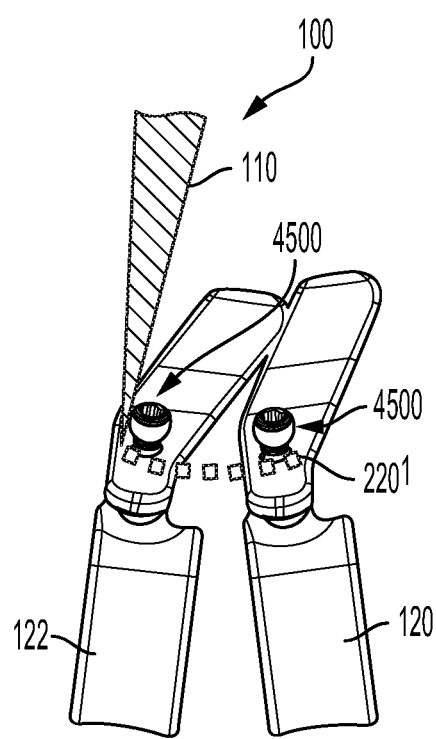
FIG. 50 is a lateral view of the dispensing component of the additive-manufacturing system repositioned to the starting position for applying substrate material between the vertebrae, connecting the screws and thereby the vertebrae, according to the seventh general embodiment of the present disclosure.

FIG. 50 shows the dispensing component 110 of the additive-manufacturing system 100 repositioned to, or adjacent to, the starting position (from FIG. 45) for applying catalyst.

Figure 51:
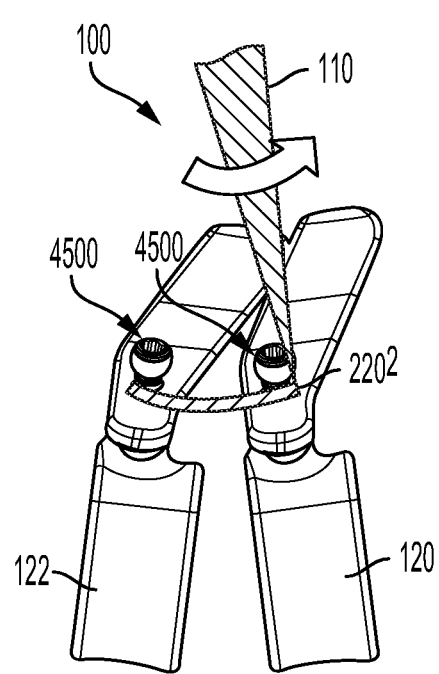
FIG. 51 is a lateral view of the dispensing component of the additive-manufacturing system applying catalyst, connecting the screws and thereby the vertebrae, according to the seventh general embodiment of the present disclosure.

FIG. 51 shows the dispensing component 110 of the additive-manufacturing system 100 being moved and applying catalyst $220^2$ on, to, or at the substrate material $220^1$, connecting the bone anchors 4500, and thereby the vertebrae 120, 122.

Figure 52:
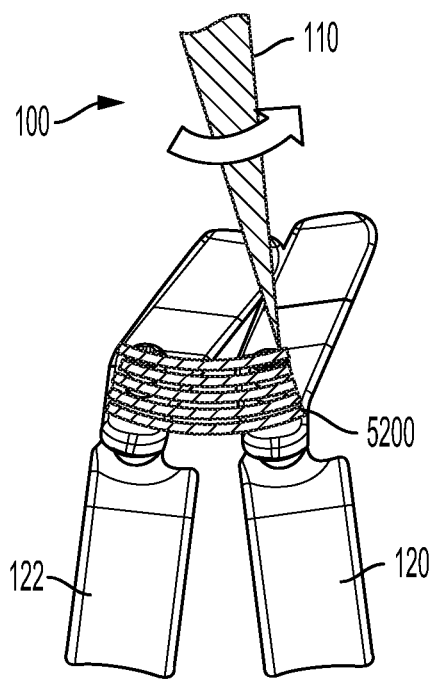
FIG. 52 is a lateral view of the dispensing component of the additive-manufacturing system completing application of printing material, connecting the screws and thereby the vertebrae, to form the in-situ implant, according to the seventh general embodiment of the present disclosure.

FIG. 52 is a lateral view of the dispensing component 110 of the additive-manufacturing system 100 completing depositing of printing material 220², 220¹, connecting the bone anchors 4500, and thereby the vertebrae 120, 122.

Figure 53:
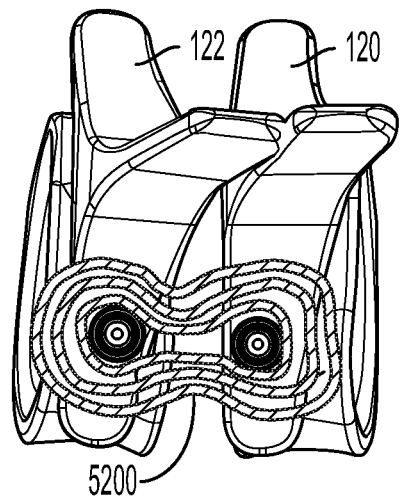
FIG. 53 shows an oblique perspective view of the printed in-situ implant, connecting the vertebrae, according to the seventh general embodiment of the present disclosure.

FIG. 53 shows an oblique perspective view of the in-situ printed connecting implant 5200, connecting the vertebrae 120, 122, according to the seventh general embodiment of the present disclosure.

Other embodiments of the present technology include in-situ-grown, printed, formed, or in-situ-manufactured motion-sparing implants, motion-sparing implants, additive manufacturing systems for forming motion-sparing implants in-situ, and methods for forming the same. In some embodiments, an in-situ manufactured motion-sparing implant may be grown or formed in discrete portions that are positioned and/or re-positioned according to an iterative process. In some embodiments, an in-situ manufactured motion-sparing implant may be grown or formed between pre-printed or pre-manufactured endplates positioned within an intervertebral disc space. In other embodiments, a plurality of in-situ manufactured motion-sparing implants may be sequentially grown or formed and repositioned or otherwise manipulated in order to fill a disc space between adjacent vertebrae and restore, support, or otherwise correct alignment, nerve endings, and/or range of motion of a patient's spine. In some embodiments, in-situ manufactured motion-sparing implants may be formed as a composite in-situ motion-sparing spinal implant selectively having rigid properties and motion-sparing properties. For example, a composite in-situ motion-sparing spinal implant may have a rigid lattice like framework that is filled or partially filled with a relatively softer pliable material. As used herein, the term "rigid" is intended to have its ordinary technical meaning referring to stiffness of a material where a material may be considered "rigid" if it is stiff or hard and in some cases a "semi-rigid material" may be marginally deformable or flexible. As used herein, the term "pliable" is intended to have its ordinary technical meaning referring to materials that are easily bent, compressed, and/or flexible.

The term in-situ manufactured motion-sparing implant, or motion-sparing implant is used primarily herein to describe the subject interbody implants 10000, 11000, 12000 or discrete components thereof, being formed with various materials and having properties that facilitate a designed range of motion and/or have flexible properties imparting advantages such as cushioning or shock absorption between adjacent vertebrae. In some embodiments, multiple in-situ manufactured motion-sparing implants are grown or formed and fused together and/or positioned adjacent one another and referred to as a single in-situ manufactured motion-sparing implant. Exemplary use cases, methods of manufacture, and corresponding illustrations thereof are not meant to be limiting, such as limiting the shape or size of the subject interbody implants 10000, 11000, 12000 unless otherwise described expressly in this specification or appended claims.

Figure 55:
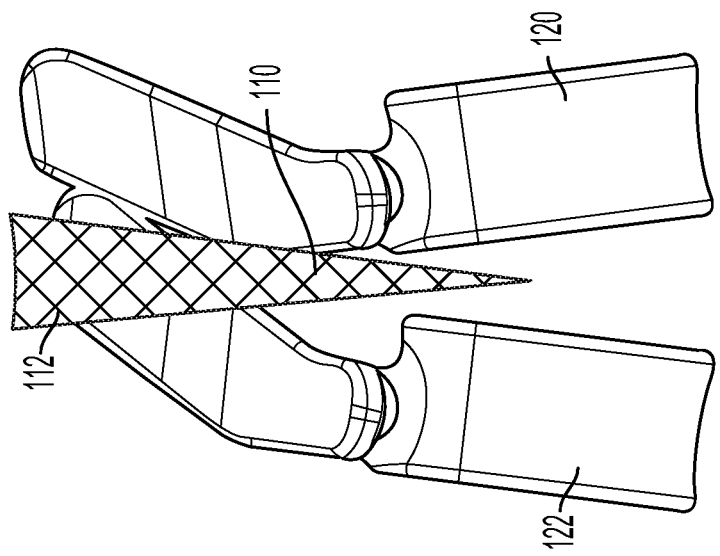
FIG. 55 shows a lateral view of patient vertebrae to be supported by an in-situ printed motion-sparing implant after an armature and dispensing component are positioned therebetween.
Figure 54:
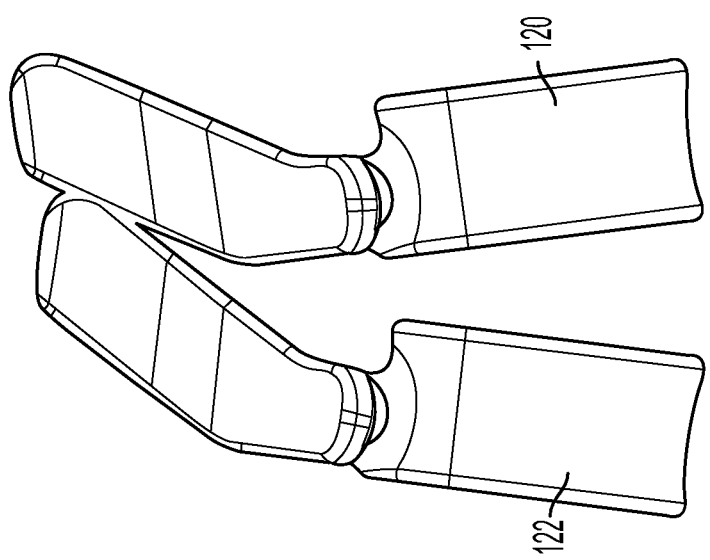
FIG. 54 shows a lateral view of patient vertebrae to be supported and/or manipulated by an in-situ printed motion-sparing implant.

FIGS. 54 and 55 may show lateral views of a patient's vertebrae to be supported and/or manipulated by an in-situ printed motion-sparing implant and/or a plurality of in-situ printed motion-sparing implants. Exemplary embodiments may be used to correct a spacing between adjacent vertebrae of a patient's spine and/or alignment of a patient's spine in the coronal or sagittal plane, for example. In some embodiments, a target alignment may be predetermined by data parsing performed by controller 1050 in coordination with scanning data, navigation equipment 1095, CT-Images, etc. which may assess a patients current spinal alignment and calculate a target alignment. For example, exemplary embodiments may include a robotic subsystem having robotics equipment 1030 including scanning and imaging equipment configured to scan a patient's anatomy. Exemplary embodiments may further include an armature 112 including a dispensing component 110 configured to dispense at least one printing material and/or mix a plurality of separately stored materials at a mixing component or mixing portion proximate the dispensing tip (not illustrated). The controller apparatus 1050 may include a processor and a non-transitory computer-readable medium. The controller 1050 may be configured to control the robotics equipment 1030 including the various scanning and imaging equipment to determine a target alignment of a patients spine, and develop an in-situ-printing plan (or in-situ printing instructions) including an in-situ material selection plan. In some embodiments, the in-situ-printing plan may be based on the target alignment of the patient's spine, and an interbody access space which may only partially provide access to a disc space between adjacent vertebra of the patients spine. In some embodiments, the in-situ material selection plan may be based on the design criteria of the particular implant, e.g., some implants and surgical situations may benefit from a substantially rigid implant whereas others may benefit from a highly flexible implant imparting cushioning benefits and a relatively greater range of motion. Controller 1050 may execute the in-situ-printing plan to thereby control the armature 112 to dispense at least one printing material from dispensing component 110 to form at least one motion-sparing implant.

In-situ manufactured motion-sparing implants may be printed, grown, or formed from a variety of materials, and combinations of materials. The materials listed herein are not exhaustive, nor are they meant to be limiting, and should be considered as exemplary in nature. For example, some materials may be substituted for other materials, especially when the substitution is with a material having the same or substantially the same material properties and/or an alternate formation that is optimized for 3-D printing technologies. The following is an exemplary listing of potential materials that may be printed by disclosed in-situ additive manufacturing systems via, e.g., dispensing component 110.

At least one printing material selectively dispensed by dispensing component 110 may be and or include polymethylmethacrylate (PMMA), commonly referred to as acrylic. PMMA may be considered a rigid polymer having a material stiffness substantially similar to bone (or at least having a material stiffness within the range of cancellous bone to cortical bone). For example, PMMA may have a modulus of elasticity of about 3 GPa which falls within the range of the modulus of elasticity of cancellous bone to cortical bone, about 0.3 GPa-20 GPa. PMMA may be capable of curing in place at relatively low temperatures making it an ideal material for in-situ printing in a patient's body. PMMA may be considered a relatively brittle polymer having a low fracture strain on the order of 1%-3% while also being a suitable material in compression and generally suitable as a filler material.

Another printing material selectively dispensed by dispensing component 110 may be and or include epoxies. Epoxies may be used as an adhesive to join separable components motion-sparing implants and/or adhere motion-sparing implants to relevant anatomical features such as, e.g., vertebrae. Epoxies may be cured in place as a single part epoxy or as a two part epoxy including a substrate material and a curing material that are mixed together at a mixing portion of dispensing component 110. Some epoxies may cure under ultraviolet light (UV) and be advantageous in the target field because of a relatively low curing temperature. Generally, epoxies may form high quality bonds with other disclosed materials, e.g., rigid materials such as PMMA and may therefore be used to couple relevant components of disclosed motion-sparing implants.

Another printing material selectively dispensed by dispensing component 110 may be and or include polytetrafluoroethylene (PTFE). At least one advantage of PTFE is that is considered a highly inert material that is chemically stable and therefore poses a relatively low risk of causing biological complications such as a host rejecting the material. PTFE may include a porous structure that may facilitate bony ingrowth therebetween the pores. Another printing material selectively dispensed by dispensing component 110 may be and or include silicone. Silicone may be considered a relatively soft elastomeric material (rubber like material) having a relatively low modulus of elasticity at about 0.05 GPa. Silicone is capable of curing in place at a relatively low temperature making it an advantageous material for in-situ printing in a patient's body. Silicone is also generally considered a highly inert material that is chemically stable and therefore poses a relatively low risk of causing biological complications such as a host rejecting the material.

Another printing material selectively dispensed by dispensing component 110 may be and or include polyurethanes. Polyurethane may be produced in many various compositions having a wide range of mechanical properties varying from pliable (soft) to rigid (hard). In at least one embodiment, a first polyurethane composition is applied as a type of cure in place compressible foam which may be suitable as a filler type material which may have material properties substantially similar to bone structures, e.g., cancellous bone. In an alternate embodiment, a second polyurethane composition is formed for a rigid application having material properties substantially similar to bone structures, e.g., cortical bone. Another printing material selectively dispensed by dispensing component 110 may be and or include Polylactic acid (PLA). PLA may be a biodegradable polymer, a special class of polymer that decomposes after its intended purpose into natural byproducts such as water, biomass, inorganic salts, carbon dioxide, and nitrogen.

In some embodiments utilizing polyurethane foam, the dispensing component 110 and controller 150 may account for a predetermined amount of expansion of the polyurethane foam that naturally occurs after mixing/curing/printing. For example, the controller 150 may develop an in-situ printing plan and in-situ material selection plan that accounts for the expansion of some materials such that the expansion does not adversely influence subsequent materials and/or layers printed on top or in contact with the polyurethane foam. For example, an initial volume of printed material may be less than the final design volume of a fully cured and expanded material and the controller 150 may initially control the dispensing component 110 to print an amount of material that is less than the designed volume (because the controller 150 recognizes that the material will expand to the design volume after fully curing and or expanding). Similarly, in other embodiments, controller 150 may determine that a disc space having a predetermined three-dimensional design volume should be filled, at least partially, with an expanding polyurethane foam that may advantageously apply a pre-load force on the superior and inferior vertebrae defining the disc space due to the expansion of the polyurethane. For example, the patient's natural anatomical features may be subjected to a pre-load from an expanding material such as polyurethane. Similarly, in other embodiments, expanding materials may apply a preload between in-situ additive manufactured endplates, e.g., between rigid materials and/or endplates.

Another class of materials that may be selectively dispensed by dispensing component 110 may be and or include hydrogel materials. In some embodiments, PMMA may be used as a hydrogel material. In other embodiments, polyvinyl may be used as a hydrogel material. Hydrogels may be composed of "smart" polymers that have mechanical properties lending itself to be used as an actuator by water absorption to an expanded, soft pliable form and by water evaporation to a contracted, rigid form. Hydrogels may resemble mechanical properties of intervertebral discs.

In some embodiments, controller 1050 may direct armature 112 and dispensing component 110 to print material by a freeform reversible printing technique. Free form reversible printing techniques may be used to print soft polymers and/or disclosed hydrogels that otherwise may not be printed in-situ in a patient due to lack of surrounding structure and/or atmospheric air. According to at least one freeform reversible printing technique, dispensing component 110 may print a liquid form pre-polymer in a gel like substance in order to generate a particular shape. In the disclosed technique, the gel like substance may provide structure, or formwork, for the liquid form pre-polymer while the liquid form pre-polymer cures. Then, after curing, the resultant polymer may be removed from the gel like substance or vice-versa. Free form printing techniques may also be used to print tissue like structures having disc like mechanical properties ranging from touch fibrous collagen to relatively softer collagen.

In some embodiments, controller 1050 may include proprietary software, such as, for example, a modified version and/or updated version of Medtronic's Mazur software platform, for analyzing and pre-operatively defining a geometry within a disc space of a patient. For example, controller 1050 may utilize the Mazur software in coordination with X-Ray Images and/or CT-Images and/or MRI Images which may be further processed to develop a three dimensional model of the disc space of the patient. In at least one embodiment, the controller 1050 generates a plan for the final three-dimensional geometry of a completed motion-sparing implant. The final three-dimensional geometry of the completed motion-sparing implant may be broken down into various segments or portions by the controller 1050 that may later be coupled or bonded together by epoxies or other bonding agents and/or other mechanical fasteners. For example, a completed motion-sparing implant may be formed in various sections where each section is formed of an alternate material having different material properties. In this way, the controller 1050 may develop an in-situ printing plan including an in-situ material selection plan. After the controller, 1050 has developed the in-situ printing plan and in-situ material selection plan the controller 1050 may control printing of the various segments or portions as individual in-situ manufactured motion-sparing implants, as will be explained in further detail below.

In some embodiments, controller 1050 may develop a pre-established in-situ printing plan including a pre-established in-situ material selection plan. Once a target alignment is determined, controller 1050 may also calculate a surgical sequence and/or installation sequence for printing at least one in-situ manufactured motion-sparing implant, e.g., in-situ manufactured motion-sparing implants of FIGS. 54-71. In those embodiments where controller 1050 determines multiple portions having different material compositions are necessary the installation sequence may involve manipulating, repositioning or otherwise coupling at least one portion to another portion before or during placement of a composite in-situ manufactured motion-sparing implant in the disc space of a patient. Controller 1050 may also determine that multiple in-situ manufactured motion-sparing implants having different shapes such as discs, wedges, etc. should be printed.

In the disclosed embodiment of FIGS. 54-63, controller 1050 may have determined that a motion-sparing implant 10000 formed of a combination of rigid and pliable material should be printed in-situ between adjacent vertebrae 120, 122 of a patient. Exemplary rigid materials may be and/or include PMMA, PTFE, polyurethanes, Polyether ether ketone (PEEK), Polyetherketoneketone (PEKK) and other thermoplastic materials and relevant biocompatible materials having a modulus of elasticity generally within the range of boney structures as explained hereinabove. In some embodiments, a rigid material may have a modulus of elasticity roughly corresponding to a vertebrae, and in other embodiments a rigid material may have a modulus of elasticity roughly corresponding to the annulus fibrosis. Exemplary pliable materials may be and or include silicone, polyurethanes, hydrogels, polyvinyl, and other relevant biocompatible materials having a modulus of elasticity generally less than the range of boney structures as explained hereinabove. In some embodiments, a pliable material may have a modulus of elasticity roughly corresponding to the nucleus pulposus and in other embodiments a pliable material may have a modulus of elasticity roughly corresponding to the annulus fibrosus. However, it shall be understood that the disclosed embodiment of FIGS. 54-63 is exemplary and that controller 1050 may determine a rigid or semi-rigid material shall be used based on the particular variables of the specific patient being treated. In this way, controller 1050 may determine a custom surgical procedure for each particular patient. Similarly, disclosed expandable cages may be printed by any above disclosed technique and with any above disclosed procedure. For example, armature 112 may dispense a dispensing component 110 as previously disclosed hereinabove that may include any sequence of forming an interbody motion-sparing implant via a substrate and/or catalyst such as is, for example, disclosed in FIGS. 13-22.

Figure 57:
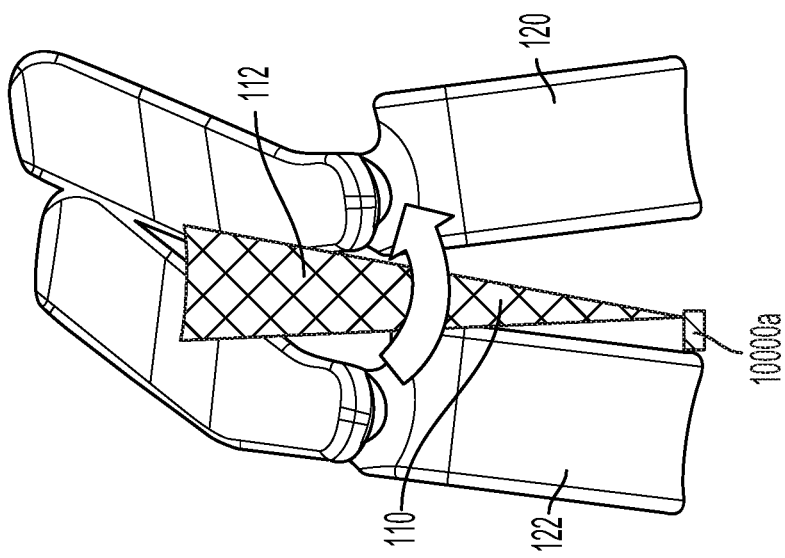
FIG. 57 shows a lateral view of patient vertebrae to be supported by an in-situ printed motion-sparing implant after an armature and dispensing component have printed a first portion of an in situ printed motion-sparing implant.
Figure 56:
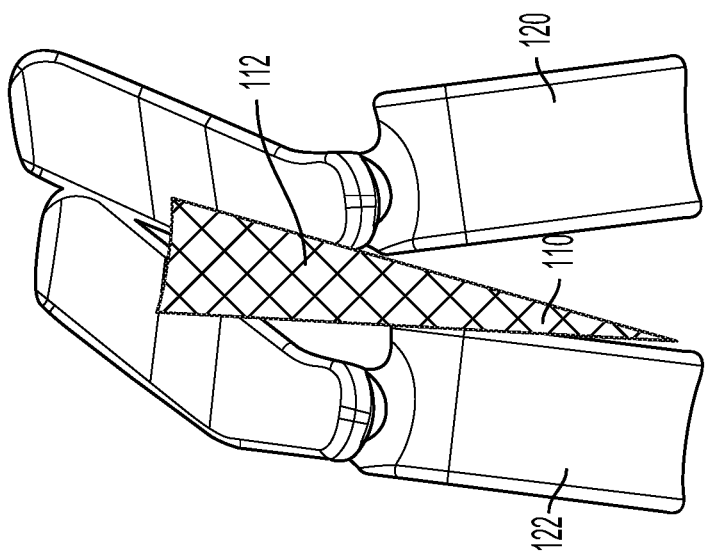
FIG. 56 shows a lateral view of patient vertebrae to be supported by an in-situ printed motion-sparing implant after an armature and dispensing component are positioned in a first printing region.
Figure 59:
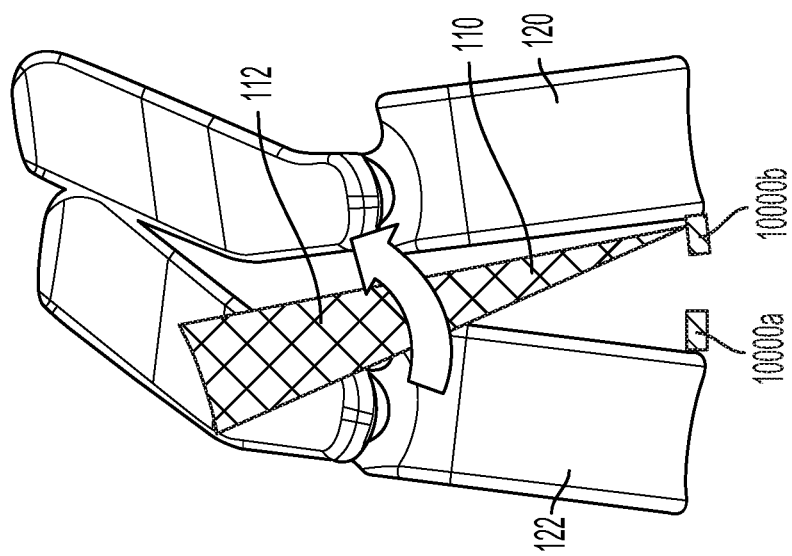
FIG. 59 shows a lateral view of patient vertebrae to be supported by an in-situ printed motion-sparing implant after an armature and dispensing component have printed a second portion of an in situ printed motion-sparing implant.
Figure 58:
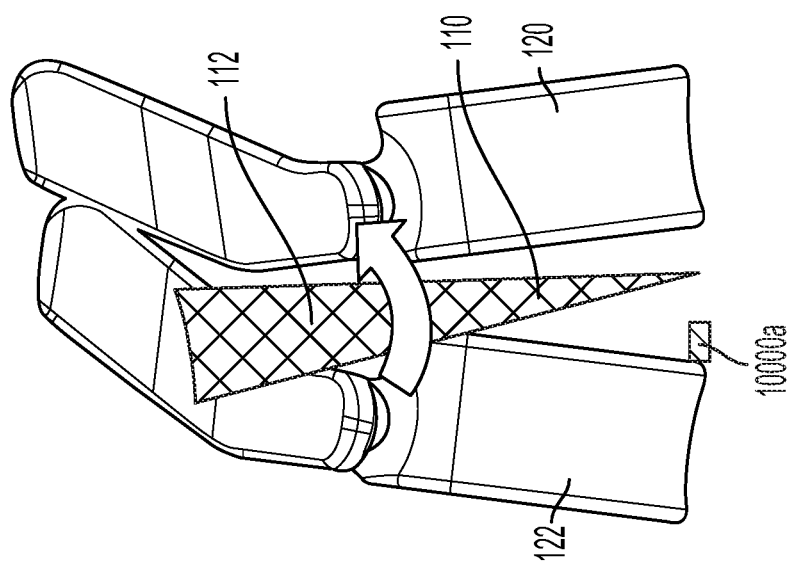
FIG. 58 shows a lateral view of patient vertebrae to be supported by an in-situ printed motion-sparing implant after an armature and dispensing component are positioned in a second printing region.

In FIG. 54, an intervertebral disc space is shown between two vertebrae 120, 122 of a patient. FIG. 55 shows the beginning of the execution of an in-situ printing plan including an in-situ material selection plan where an armature 112 and dispensing component 110 are positioned between the adjacent vertebrae 120, 122. FIG. 56 shows armature 112 and dispensing component 110 being positioned in a first printing region. The first printing region may be a region generally proximate to vertebrae 122 and extending along the interior face of vertebrae 122 in the disc space. FIG. 57 shows armature 112 and dispensing component 110 printing a first portion 10000a of an in situ printed motion-sparing implant 10000. The first portion 10000a may be formed of a rigid material abutting vertebrae 122. FIG. 58 shows armature 112 and dispensing component 110 positioned in a second printing region. The second printing region may be a region generally proximate to vertebrae 120 and extending along the interior face of vertebrae 120 in the disc space. FIG. 59 shows armature 112 and dispensing component 110 printing a second portion 10000b of an in situ printed motion-sparing implant 10000. The second portion 10000b may be formed of a rigid material abutting vertebrae 120 that is the same as or substantially the same as the rigid material of first portion 10000a.

Figure 61:
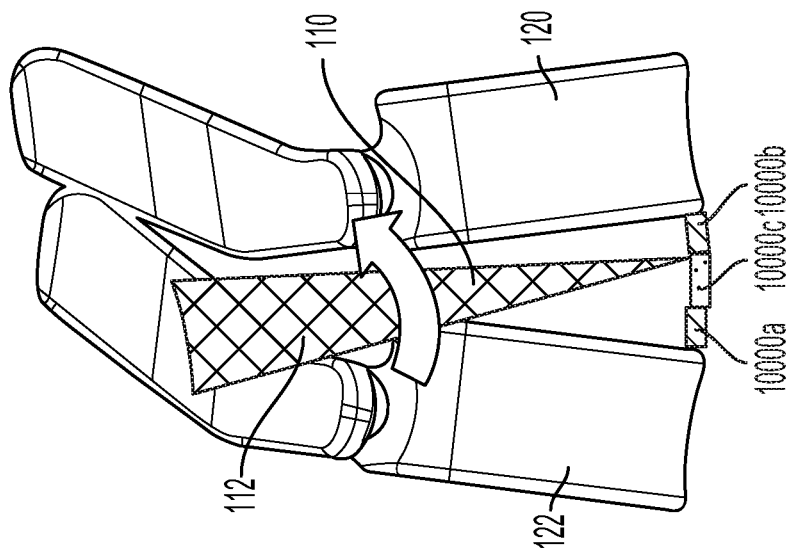
FIG. 61 shows a lateral view of patient vertebrae to be supported by an in-situ printed motion-sparing implant after an armature and dispensing component have printed a third portion of an in situ printed motion-sparing implant.
Figure 60:
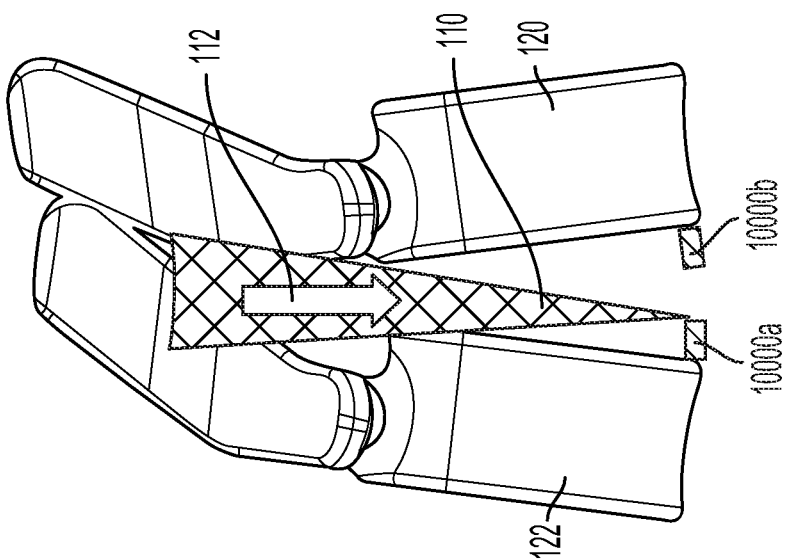
FIG. 60 shows a lateral view of patient vertebrae to be supported by an in-situ printed motion-sparing implant after an armature and dispensing component are positioned in a third printing region
Figure 63:
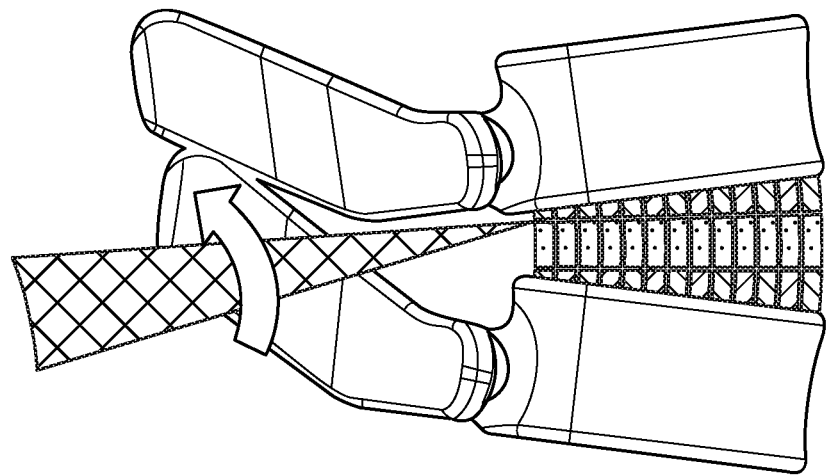
FIG. 63 shows a lateral view of patient vertebrae to be supported by an in-situ printed motion-sparing implant after an armature and dispensing component have printed an in situ printed motion-sparing implant.
Figure 62:
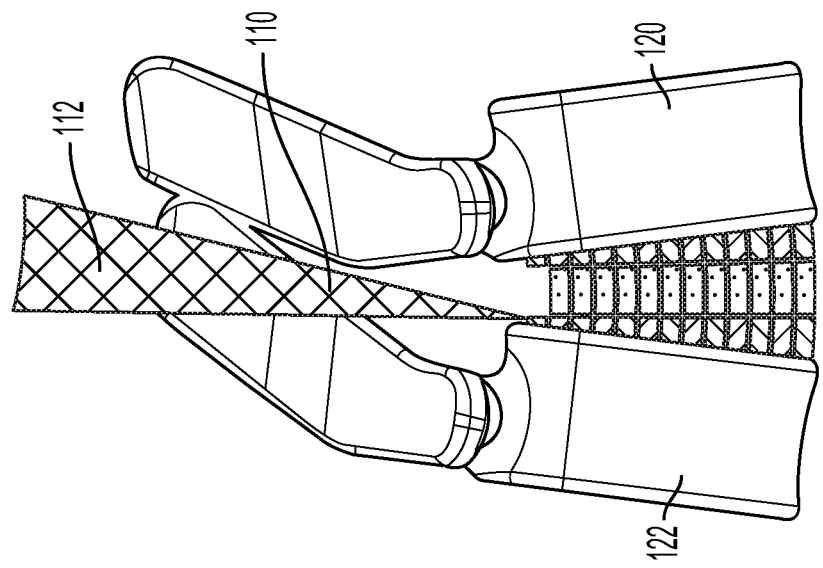
FIG. 62 shows a lateral view of patient vertebrae to be supported by an in-situ printed motion-sparing implant after an armature and dispensing component have nearly printed a complete in situ printed motion-sparing implant.

FIG. 60 shows armature 112 and dispensing component 110 positioned in a third printing region. The third printing region may be a region generally disposed in a central portion of the disc space and extending between the first region and second region. FIG. 61 shows armature 112 and dispensing component 110 printing a third portion 10000c of an in situ printed motion-sparing implant 10000. The third portion 10000c may be formed of a pliable material that is relatively softer than the rigid materials of first and second portions 10000a, 10000b. Consistent with the disclosure herein, controller 1050 may continue to direct armature 112 and dispensing component 110 to continue sequentially printing portions 10000a, 10000b, 10000c in each of first, second, and third regions until the disc space is substantially filled. For example, FIG. 62 shows armature 112 and dispensing component 110 having nearly printed a complete in situ printed motion-sparing implant 10000. FIG. 63 shows a completed in-situ printed motion-sparing implant 10000. In doing so, a composite in-situ motion-sparing implant having a top rigid end portion abutting a superior vertebra, a bottom rigid end portion abutting an inferior vertebrae, and a pliable shock absorbing portion therebetween may be formed by the disclosed additive manufacturing system.

It shall be understood that in some embodiments, portions 10000a, 10000b, 10000c may be fused together during the printing process by, e.g., an epoxy dispensed from dispensing component 110 at relevant end surfaces of adjacent portions 10000a, 10000b, and 10000c. For example, an epoxy may selectively fuse, bond, or couple the rigid material of portions 10000a, 10000b to the pliable material of portion 10000c. Additionally or alternatively, the rigid material of portions 10000a, 10000b may be fused to the corresponding adjacent vertebrae 120, 122 by epoxy. In other embodiments, silicon may be used to fuse, bond, or couple the rigid material of portions 10000a, 10000b to the pliable material of portion 10000c. In some embodiments still, the rigid first portions 10000a are fused to one another, the rigid second portions 10000b are fused to one another, and the pliable material therebetween is merely confined between the rigid first and second portions 10000a, 10000b. In other embodiments, it may be desirable for each portion 10000a, 10000b, 10000c to be independently printed by above disclosed free forming techniques and simply maintained in place due to being surrounded by vertebrae 120, 122.

Figure 64:
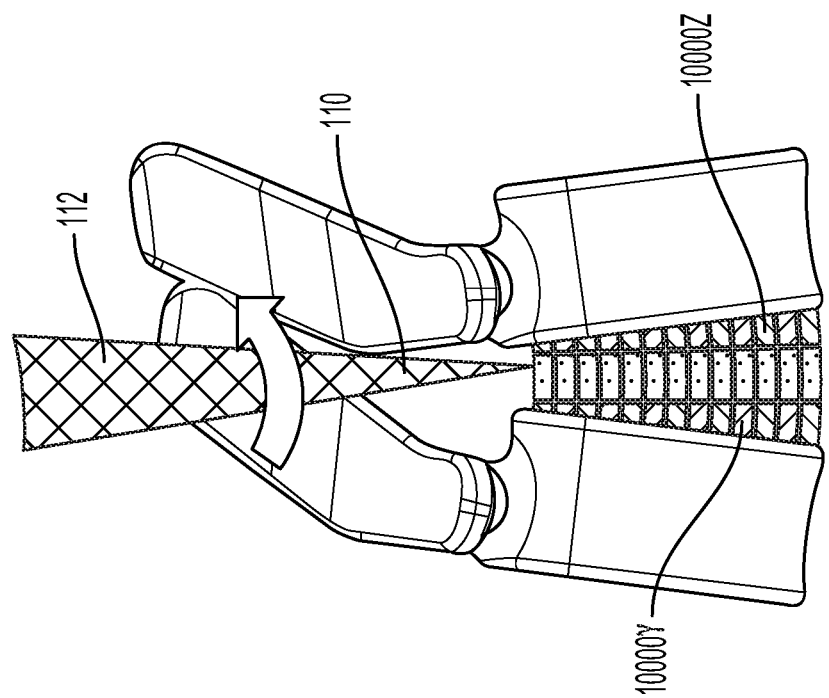
FIG. 64 shows a lateral view of patient vertebrae to be supported by rigid endplates and an in-situ printed motion-sparing implant after an armature and dispensing component have printed the in situ printed motion-sparing implant between the rigid endplates.

FIG. 64 shows a lateral view of patient vertebrae 120, 122 to be supported by a composite in-situ printed motion-sparing implant 10000'. Composite in-situ printed motion-sparing implant 10000' may include first and second rigid endplates 10000y, 10000z and an in-situ printed motion-sparing implant 10000 having the same, substantially the same, or similar properties as the in-situ printed motion-sparing implant 10000 of FIGS. 54-63. In some embodiments, first and second rigid endplates 10000y, 10000z may be preformed of stock material, i.e., preformed rigid material from a stock supply off the shelf, and insert into the disc space by a robotic arm or the like, i.e., not necessarily printed in-situ or printed according to additive manufacturing processes disclosed herein. Similarly, in some embodiments, first and second rigid endplates 10000y, 10000z may be printed by disclosed embodiments according to the in-situ printing plan and in-situ material selection plan and configured to normalize the adjacent vertebrae. For example, first and second rigid endplates 10000y, 10000z may be printed with guide walls and/or angled geometry such that they may be configured to operably engage with or guide a preformed pliable material from a stock supply off the shelf into a desired position, e.g., pliable material of portion 10000c may not necessarily be printed in-situ or printed according to additive manufacturing processes disclosed herein. In other embodiments, first and second rigid endplates 10000y, 10000z may be printed according to additive manufacturing processes disclosed herein within the intervertebral disc space or proximate the intervertebral disc space, e.g., in an operating room. Exemplary materials first and second rigid endplates 10000y, 10000z may be formed of may include PMMA, PTFE, polyurethanes, and even other biocompatible metallic materials having a modulus of elasticity generally within the range of boney structures as explained hereinabove. However, it shall be understood that first and second rigid endplates 10000y, 10000z shall not be limited to the specific materials and/or shapes disclosed herein.

Figure 65:
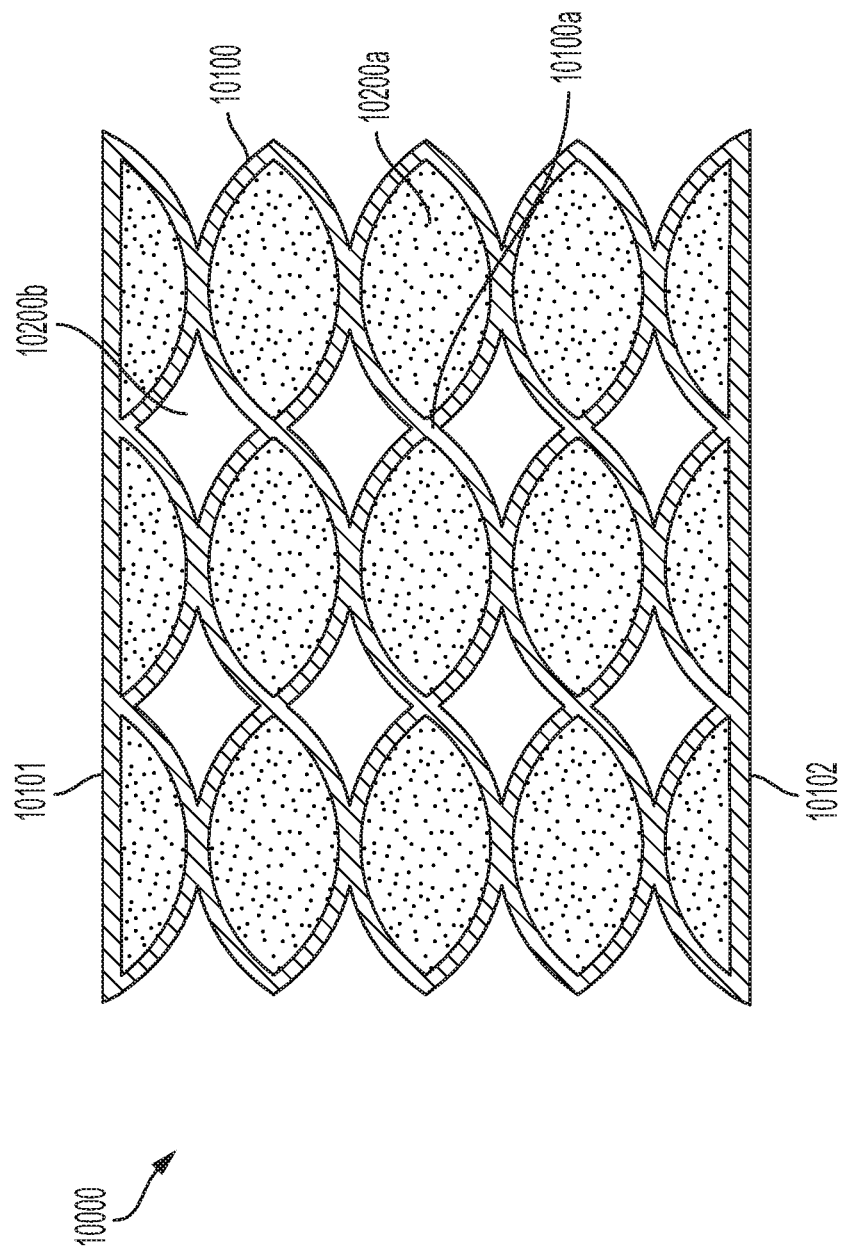
FIG. 65 is a cross section cut of an in-situ printed motion-sparing implant including a lattice structure formed of a rigid material and a fillable structure formed of a pliable material.

FIG. 65 is a cross section cut of an in-situ printed motion-sparing implant that may include a lattice structure 10100 formed of a rigid material composed of one or more repeating unit cells. In some embodiments, lattice structure 10100 may be formed of a repeating pattern of oval shaped cells 10200a and diamond shaped cells 10200b. In the illustrated embodiment, a pair of oval shaped cells 10200a and diamond shaped cells include strut like elements that are connected at nodes 10100a. The repeating pattern of lattice structure 10100 may be broken at end surfaces 10101 and 10102. The end surfaces 10101, 10102 may be formed of the same material as the rest of lattice structure 10100 or they may be formed of an alternate material. Furthermore, end surfaces 10101, 10102 may have textured high friction surfaces on the outside surfaces thereof (extending through the page) that are configured to facilitate placement and retention between vertebrae 120, 122. However, the embodiment of FIG. 65 is exemplary in nature and in-situ printed motion-sparing implants disclosed herein may have a lattice structure 10100 including any repeating pattern of open cells having any desirable shape with or without textured high friction surfaces. In at least one embodiment, lattice structure 10100 includes a plurality of relatively long singular tubes (cylinders) extending in one direction that when positioned against one result in diamond shaped spaces therebetween that also extend in the one direction and define the interstitial space between the relatively long singular tubes. The tubes may be printed individually and then layered or adhered together at the various contact points. Additionally, the tubes and diamond shaped spaces therebetween may be printed integrally. Additionally, some embodiments may include a lattice structure 10100 that is viewable by the naked eye, i.e., a lattice structure 10100 on the macro scale. However, in other embodiments the lattice structure may not be viewable by the naked eye, i.e., a lattice structure 10100 on the micro scale. Moreover, lattice structure 10100 and cells 10200a, 10200b may be printed or formed by any above disclosed in-situ additive manufacturing technique.

In the disclosed embodiment, lattice structure 10100 may be formed of a rigid material or semi-rigid material capable of bending or flexing, at least partially, and at least one of cells 10200a and 10200b may be filled with a pliable material. For example, lattice structure 10100 may be formed of or include PMMA, PTFE, polyurethanes, PEEK, PEKK, and even other biocompatible materials and/or fibers and cells 10200a, 10200b may be formed of or include silicone, polyurethanes, hydrogels, polyvinyl, and other relevant biocompatible materials. In the illustrated embodiment, cells 10200a are filled and cells 10200b are open cells, i.e., not filled. However, in some embodiments, the lattice structure 10100 may confine pliable material of cells 10200a and 10200b. For example, each of cells 10200a and 10200b may be filled with a pliable material and each of cells 10200a, 10200b may be filled with a different type of pliable material.

Figure 67:
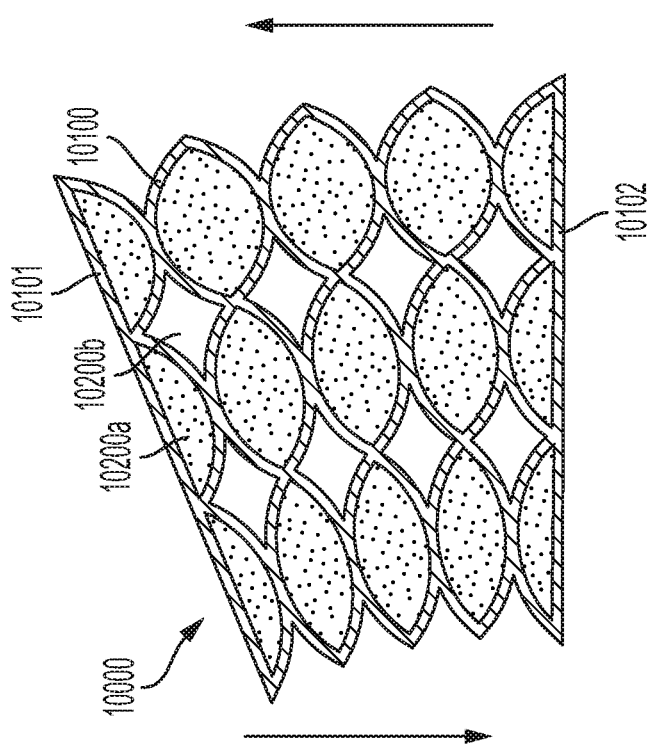
FIG. 67 is a cross section cut of an in-situ printed motion-sparing implant including a lattice structure formed of a rigid material and a fillable structure formed of a pliable material undergoing tension on a first end and compression on a second end opposite the first end.
Figure 66:
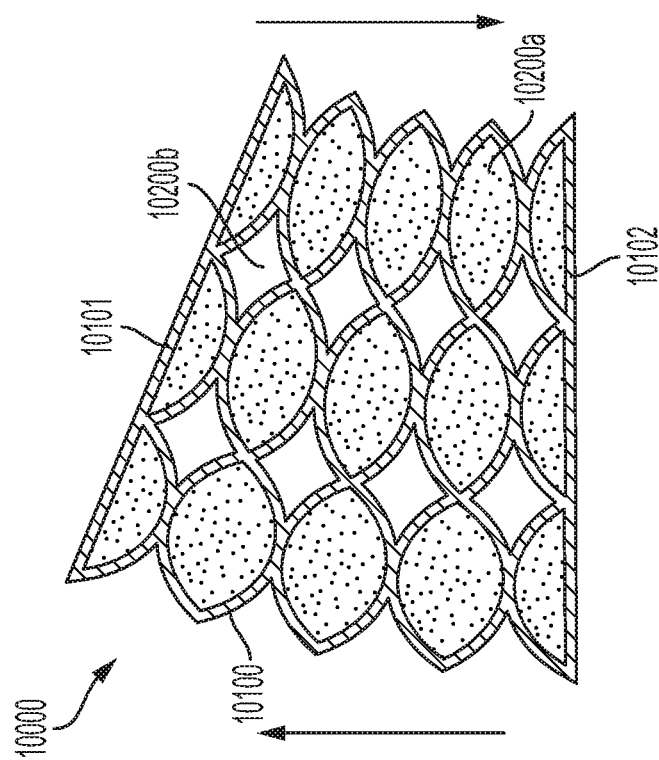
FIG. 66 is a cross section cut of an in-situ printed motion-sparing implant including a lattice structure formed of a rigid material and a fillable structure formed of a pliable material undergoing compression on a first end and tension on a second end opposite the first end.

FIG. 66 is a cross section cut of the in-situ printed motion-sparing implant 10000 including a lattice structure 10100 formed of a rigid material including a plurality of repeating cells 10200a, 10200b that may be filled with a pliable material undergoing compression on a first end (represented by downward arrow on right) and tension on a second end (represented by upward arrow on left) opposite the first end. FIG. 67 is a cross section cut of the in-situ printed motion-sparing implant 10000 including a lattice structure 10100 formed of a rigid material including a plurality of repeating cells 10200a, 10200b that may be filled with a pliable material undergoing compression on a second end (represented by downward arrow on left) and tension on a first end (represented by upward arrow on right) opposite the first end. As illustrated, the relatively thin sections of rigid material of the lattice structure 10100 may flex to facilitate motion and the cells 10200a, 10200b of pliable material (or semi-rigid material) may allow motion and also provide support for the rigid material sections of lattice structure 10100. In this way, the controller 150 may determine an appropriate amount of support and movement for a particular motion sparing implant that may be driven by the material stiffness of the filler material of cells 10200a, 10200b (or lack thereof) in relation to the material stiffness, thickness, length, and cross sectional geometry of lattice structure 10100.

Figure 68A:
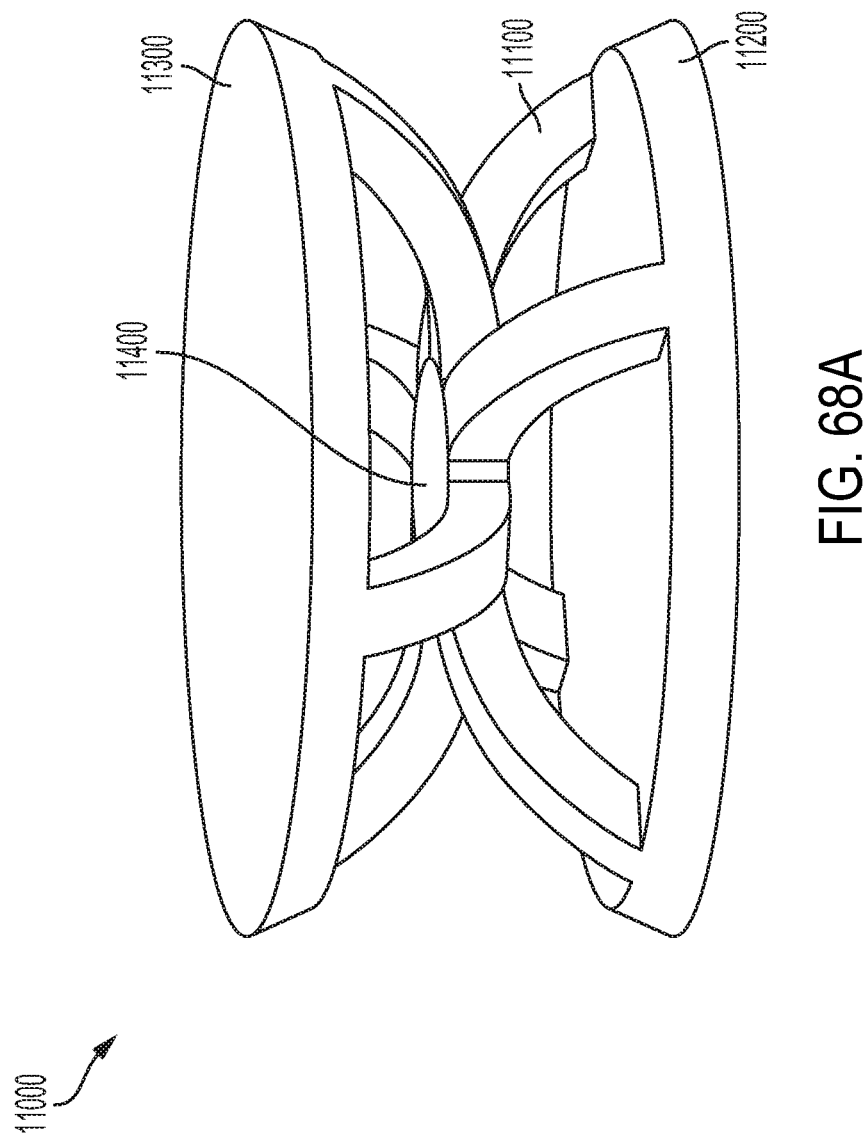
FIG. 68A is a perspective view of an in-situ printed motion-sparing implant including a first endplate and a second endplate coupled to a central portion by a plurality of flexible arms.
Figure 68B:
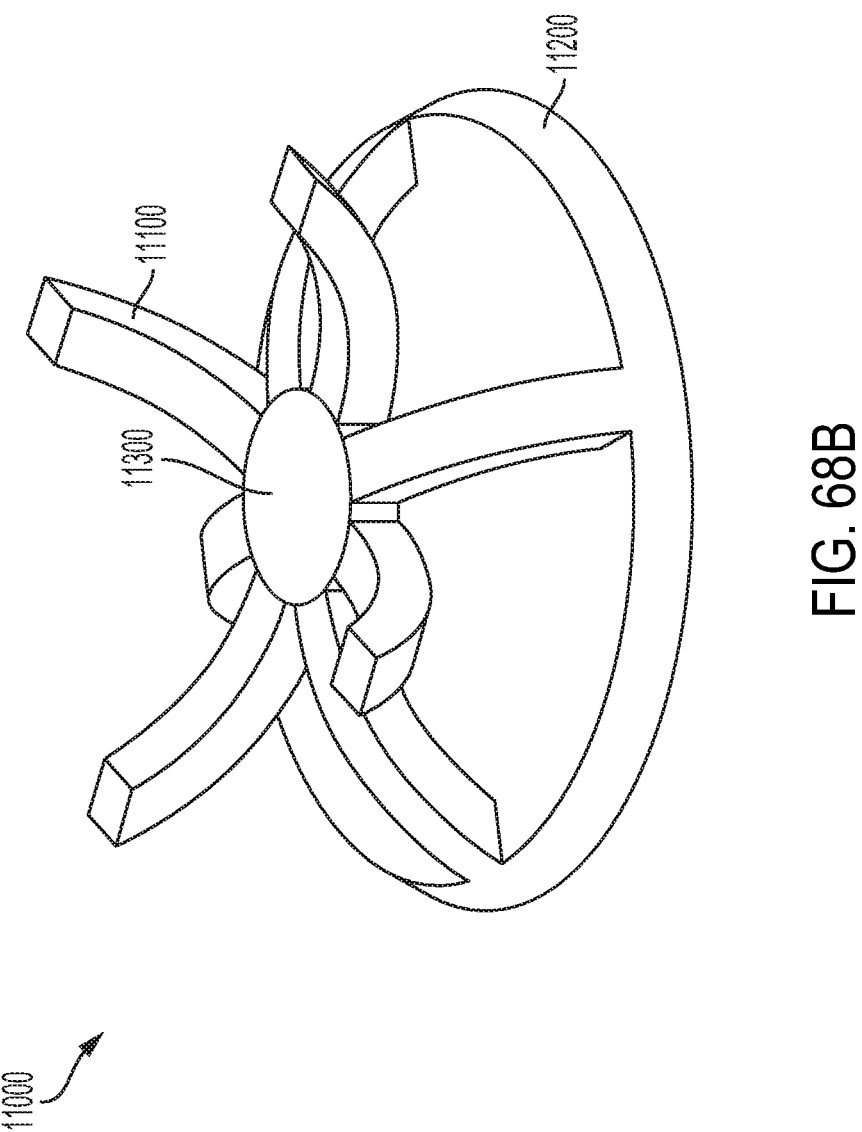
FIG. 68B is a perspective view of the in-situ printed motion-sparing implant of FIG. 68A with one of the first and second endplates removed.

FIG. 68A is a perspective view of an in-situ printed motion-sparing implant 11000 including a first endplate 11200 (superior endplate) and a second endplate 11300 (inferior endplate) coupled to a central portion 11400 by a plurality of flexible arms 11100. FIG. 68B is a perspective view of the embodiment of FIG. 68A with the top endplate 11300 removed for ease of understanding. In the exemplary embodiment, first endplate 11200, second endplate 11300, central portion 11400, and flexible arms 11100 may be printed or formed according to any above disclosed in-situ additive manufacturing technique. In some embodiments, each of first endplate 11200, second endplate 11300, central portion 11400 and flexible arms 11100 may be printed of the same material. In other embodiments, first endplate 11200, second endplate 11300, central portion 11400 and flexible arms 11100 may be printed of a variety of materials having varying material properties and various layering as represented generally by the alternating hatching of FIG. 69A. For example, in some embodiments, first endplate 11200, second endplate 11300, and central portion 11400 may be printed of a rigid or semi-rigid material having at least one layer or a plurality of layers and flexible arms 11100 may be printed of an alternate material that is pliable or at least relatively flexible compared to endplates 11200, 11300. In the disclosed embodiment, four uppermost curved flexible arms 11100 may be coupled to a disc shaped central connecting portion 11400 and a first endplate 11100 to thereby define a dome shaped interior space therebetween. Similarly, four lowermost curved flexible arms 11100 may be coupled to the disc shaped central connecting portion 11400 and a second endplate 11200 to thereby define a dome shaped interior space therebetween. In some embodiments, the flexible arms 11100, endplates 11200, 11300, and connecting portion 11400 are printed separable of one another and adhered to one another at corresponding end portions by epoxy. In some embodiments, the plurality of flexible arms 11100, central portion 11400, and/or infilled pliable material may be referred to as a shock absorbing portion.

Figure 69A:
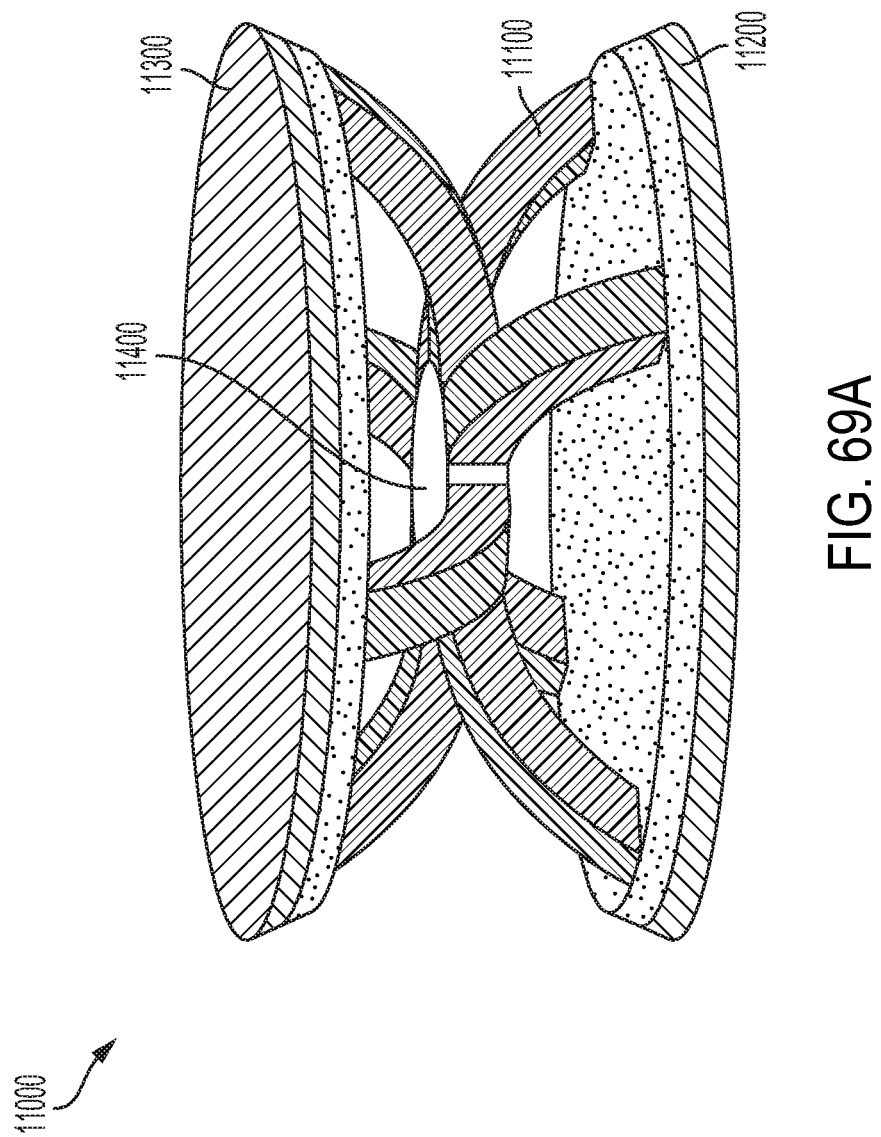
FIG. 69A is a perspective view of an in-situ printed motion-sparing implant including a first endplate and a second endplate including a plurality of different material compositions.
Figure 69B:
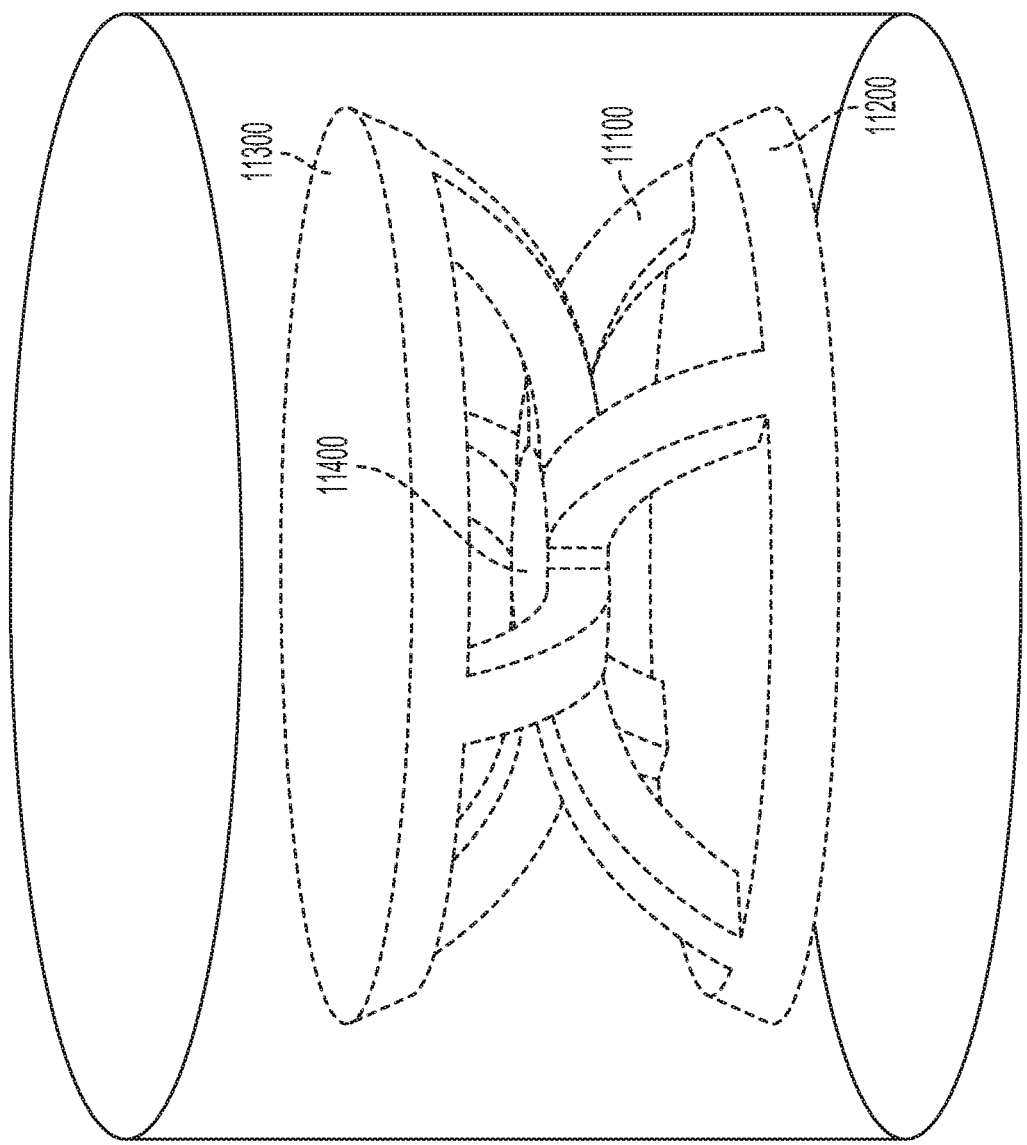

In some embodiments, it may be advantageous for first endplate 11200, second endplate 11300, central portion 11400 and flexible arms 11000 to be printed of a rigid material, for flexible arms 11000 to be relatively thin such that they may flex, and for the interstitial area between endplates 11200 and 11300 to be filled with a pliable material. For example, as illustrated in FIG. 69B, first endplate 11200, second endplate 11300, central portion 11400 and flexible arms 11000 (shown with skeleton lines for ease of understanding) may be surrounded by a correspondingly shaped pliable material (shown with solid lines for ease of understanding). Similarly, in other embodiments, the dome shaped area between first endplate 11300, the uppermost arms 11000, and a central disc shaped connecting portion 11400 may be filled with a pliable material and the dome shaped area between second endplate 11400, the lowermost arms 11000, and the central disc shaped connecting portion 11400 may be filled with a pliable material. However, it shall be understood that discrete portions defined by relevant components may be selectively filled with pliable material, rigid material, or any combination thereof. Furthermore, any of the relevant components may have a lattice like structure 10100 defining a plurality of repeating cells 11200*a*, 11200*b* filled with a pliable material consistent with the above disclosure.

Figure 70:
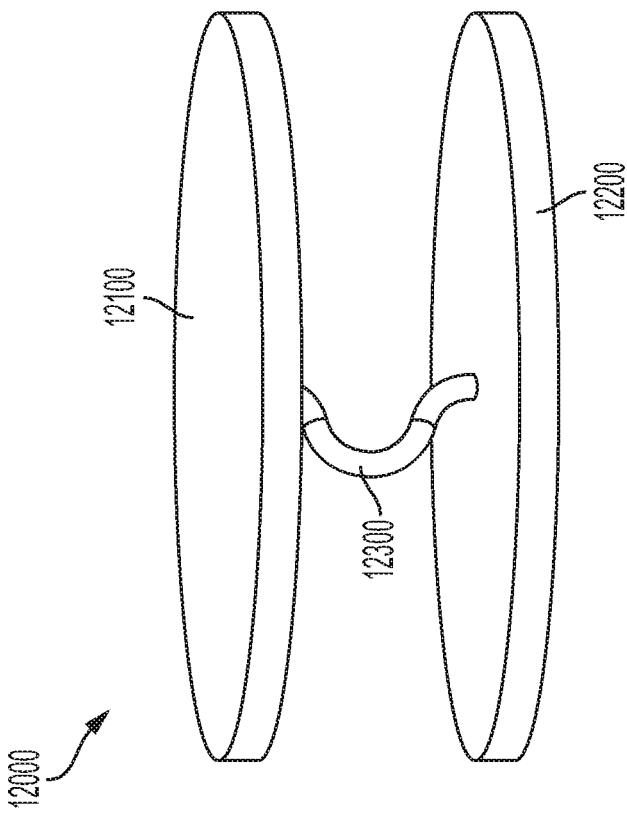
FIG. 70 is a perspective view of an in-situ printed motion-sparing implant including a first endplate and a second endplate coupled together by a tether.

FIG. 70 is a perspective view of an in-situ printed motion-sparing implant 12000 including a first endplate 12100 and a second endplate 12200 coupled together by a tether 12300. In the exemplary embodiment, first endplate 12100, second endplate 12200, and tether 12300 may be printed or formed according to any above disclosed in-situ additive manufacturing technique. In some embodiments, first endplate 12100, second endplate 12200, and tether 12300 may be printed of the same material. In other embodiments, first endplate 12100, second endplate 12200, and tether 12300 may be printed of a variety of materials having varying material properties.

In the disclosed embodiment, tether 12300 may be a fiber or exhibit fiber like material properties in that tether 12300 may exhibit relatively strong tensile strength and relatively lower compressive strength. Endplates 12100, 12200 may be formed of a rigid material. Tether 12300 may be coupled to endplates 12100, 12200 by epoxy or other bonding agent or mechanically. Consistent with above disclosed embodiments, controller 1050 may determine, according to an in-situ printing plan and in-situ material selection plan, that the endplates 12100, 12200 should have a sizing corresponding to intervertebral disc space of a patient and the tether 12300 should have a length corresponding to the desired spacing between adjacent vertebrae 120, 122 (while also accounting for the relevant width of endplates 12100, 12200). Therefore, a combined height of an in situ printed motion-sparing implant 12000 may correspond to a target spacing between adjacent vertebrae as determined by controller 1050.

Figure 71:
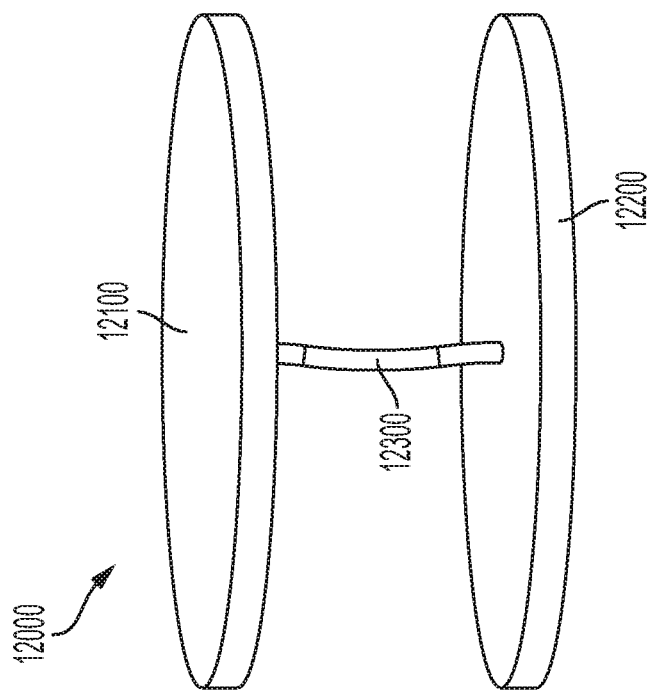
FIG. 71 is a perspective view of an in-situ printed motion-sparing implant including a first endplate and a second endplate coupled together by a tether.

At least one advantage of the embodiment of FIGS. 70 and 71 is that the endplates 12100, 12200 of in-situ printed motion-sparing implant 12000 may be collapsed (FIG. 70) to initially position the in-situ printed motion-sparing implant 12000 between vertebrae 120, 122, e.g., by armature 112. After positioning in-situ printed motion-sparing implant 12000 between vertebrae 120, 122 the armature 112 may position dispensing component 110 in the disc space of the patient and between endplates 12100, 12200 for further printing. For example, dispensing component 110 may dispense a printing material, e.g., a pliable material to fill and/or expand the spacing between endplates 12100, 12200. In some embodiments, dispensing component 110 may dispense an expanding foam like material that expands during a curing process over time to fill the space between endplates 12100, 12200, e.g., a polystyrene or polyurethane foam which may be selectively mixed by a mixing component or mixing portion coupled to dispensing component 110. For example, an expanding foam like material may be a self-expanding or automatically-expanding foam that expands due to a chemical process or interaction between materials over time and/or by being originally under pressure and allowed to expand after being dispensed by dispensing component. Furthermore, motion-sparing implant 12000, or portions thereof, may be provided off-the-shelf and implanted as explained above, then the controller 150 may direct dispensing component 110 to print pliable material around the motion sparing implant 12000 according to the needs of the patient or surgeon. One advantage of the tether, is that it may prevent the over extension or over expansion of endplates 12100, 12200. For example, in some embodiments, tether 12300 is preloaded such that it is in tension and actively preventing the over extension of the disc space beyond pre-designed criteria. In some embodiments, endcaps 12100, 12200 may be pre-formed and the disclosed in-situ additive manufacturing system may determine an appropriate length of an adjustable tether 12300 and then adjust tether 12300 to the appropriate length or provide instructions to a surgeon to perform the same. Thereafter, endcaps 12100, 12200 and the adjusted tether 12300 may be placed in the intervertebral space of a patient and the void space between endcaps 12100, 12200 may be filled with a pliable material, semi-rigid material, an expanding foam, or any combination thereof.

Additionally, although the example embodiment is shown with a single tether 12300 and the first and second endplate 12100, 12200 have lateral surfaces projecting parallel to one another; other embodiments may include a plurality of tethers 12300 where first and second endplates 12100, 12200 have lateral surfaces inclined with respect to one another. For example, in some embodiments, a first group of tethers 12300 may have a first length and be disposed radially between a left portion of endplates 12100, 12200 and a second group of tethers 12300 may have a second length, greater than the first length, and be disposed radially between a right portion of endplates 12100, 12200. Consistent with above disclosed embodiments, the area between endplates 12100, 12200 may be filled with a pliable material putting the tethers in tension and expanding a spacing between endplates 12100, 12200. In having tethers 12300 of varying lengths first and second endplates 12100, 12200 may be inclined with respect to one another. At least one advantage of this arrangement is that a patient's spine may be corrected and/or otherwise aligned in the coronal or sagittal plane.

Consistent with the above disclosure with respect to implants 10000, 11000, and 12000 each implant may further be configured with at least one aperture configured to receive an anchor, e.g., a bone screw or the like, for anchoring into an adjacent vertebrae. The anchor may help maintain the corresponding implant 10000, 11000, 12000 in contact with the adjacent vertebrae to facilitate load distribution.

Additional Example Aspects

Further regarding protecting the patient during the procedure, as mentioned above, in various embodiments, such as those involving application of chemical and/or heat in implant formation, care should be taken to ensure that patient tissue is not exposed to undesirable affects, including by not limited to undesirable levels of heat. It is also considered that the process could include cold fusing of materials. One example of such includes leveraging a cement reaction. These are other ways to protect the patient from extreme temperatures or conditions.

Further regarding customizing implant formation and structure to patient anatomy, as mentioned above, gauge(s) can be used to facilitate registering patient bone quality and adjusting the implant accordingly. For instance, if the gauge senses weak, or relatively weaker bone material adjacent the dispensing component 110, the system 100 (e.g., computing controller 1050) could apply material accordingly, such as in higher volume or in a special configuration to better address the weakness, such as by a configuration that covers more surface area at, in, or adjacent the weak area. And as mentioned the converse can be true. That is, less material or a special configuration can be used when strong bone is detected, such as by using less material, which can save material and time, and so cost, and be less invasive. In an additional aspect, the system 100 can in response to gauge recordings or other patient anatomy data (from imaging, etc.), form more or less channeling or voids, to guide bone growth into the implant more selectively, such as by promoting more bone growth in certain areas of the patient/implant.

Further regarding positive, or protruding features, as mentioned, the implant could be printed with protrusions, such as spikes, such that moving the adjacent vertebral body/ies to contact the implant would drive the protrusions into the vertebral body/ies, promoting implant securement in place. Along with or instead of spikes, these positive features (versus negative features like channels, holes, etc.) can include, for instance, teeth, ridges, detents, convexities, one-way teeth, the like, or other.

In a contemplated embodiment, positive features and negative features are formed and function together. A channel within an implant according to the present technology could have formed on its wall/s, for instance, a positive feature, such as a protrusion. Such positive feature/s within a negative feature can provide benefits such as promoting stronger bone in-growth to implant connectivity, and stronger resulting implant construct. Conversely, any implant positive feature, such as an outer surface protrusions, could have negative features formed therein, such as dimpling, holes, micro-channels, or the like. Benefits can include improved gripping (implant to patient), or increased bone in-growth to the implant, for example.

Any of the features disclosed with respect to any embodiments can be implemented with any of the other embodiments provided herein. Printing-material options described herein according to one or more embodiments can be used for implementing any of the other embodiments, for instance.

Any features from one or more embodiments can be implemented with any features described with respect to any other embodiment.

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

Any disclosure or claim herein referencing direction is not meant to limit interpretation of the disclosure, unless the disclosure or claim requires expressly such limitation. Reference, for instance, to depositing material on a vertebral surface is not limited to including printing on top of a generally horizontally disposed vertebral surface, and can include, for instance, printing on a partially or fully vertically disposed vertebral surface, for instance. As another example, references to a top or bottom of a grown or formed implant are not limited to indicating only an upper and a lower surface of the implant in a standing-patient reference frame.

Further regarding indications of direction, positioning and movement described in connection with components including but not limited to the dispensing component 110 are not restricted to the positioning and movement shown by way of examples in the figures. Actual positions and movements of the system 100 in use can be determined, pre-procedure or intra-procedure, by the computing controller 1050 and/or the surgeon or other surgical staff, and may differ from the positions and movements described or illustrated.

In addition, while certain aspects of this disclosure are described as being performed by a single module or unit for purposes of clarity, it should be understood that the techniques of this disclosure may be performed by a combination of units or modules. And aspects described as being performed by multiple modules or units, may be performed by a single module or unit in alternative embodiments.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed:

1. A motion-sparing spinal implant formed in-situ, within a patient, comprising:
   a first endcap formed of a rigid material and having a size corresponding to a first vertebral body;
   a second endcap formed of a rigid material and having a size corresponding to a second vertebral body; and
   a pliable material configured to fill an interior space between the first and second endcaps, the pliable material being dispensed by a dispensing component and cured in-situ within the disc space of a patient;
   wherein the first endcap and second endcap are formed of rigid material dispensed by the dispensing component.

2. The motion-sparing spinal implant of claim 1, wherein the first endcap and second endcap are provided from pre-formed rigid material.

3. The motion-sparing spinal implant of claim 1, wherein the first endcap and second endcap are coupled to the pliable material.

4. The motion-sparing spinal implant of claim 1, wherein the first endcap and second endcap are configured to confine the pliable material therebetween.

5. The motion-sparing spinal implant of claim 1, wherein the first endcap and second endcap are coupled together by a tether configured to define a height of the interior space between the first and second endcaps.

6. The motion-sparing spinal implant of claim 5, wherein the pliable material is an expanding material configured to expand the interior space between the first and second endplates thereby placing the tether under tension.

7. The motion-sparing spinal implant of claim 1, wherein:
the first endcap and second endcap are coupled together by at least one first tether disposed along a first radial side and at least one second tether disposed along a second radial side opposite the first radial side, and
the at least one first tether is longer than the at least one second tether.

8. The motion-sparing spinal implant of claim 7, wherein the pliable material is an expanding material configured to expand the interior space between the first and second endplates thereby placing the at least one first tether and the at least one second tether under tension and thereby inclining the first endplate with respect to the second endplate.

9. An additive-manufacturing system for printing spinal implants in-situ, within a patient, comprising:
a robotic sub system including:
scanning and imaging equipment configured to scan a patient's anatomy; and
an armature including at least one dispensing nozzle configured to selectively dispense at least one rigid material and at least one pliable material;
a controller apparatus having a processor and a non-transitory computer-readable medium storing computer-executable instructions configured to when executed by the processor cause the controller to:
control the scanning and imaging equipment to determine a target alignment of a patients spine;
develop an in-situ-printing plan including an in-situ material selection plan based on the target alignment of the patients spine, an interbody access space, and a disc space between adjacent vertebra of the patients spine; and
execute the in-situ-printing plan to:
control the armature to dispense the at least one material chosen from the at least one rigid material and the at least one pliable material to form at least one motion-sparing implant;
wherein the computer-executable instructions are further configured to, when executed by the processor, cause the controller to form at least one motion-sparing implant comprising:
a first endcap formed of a rigid material and having a size corresponding to a first vertebral body;
a second endcap formed of a rigid material and having a size corresponding to a second vertebral body; and
a pliable material configured to fill an interior space between the first and second endcaps, the pliable material being dispensed by the at least one dispensing nozzle and cured in-situ within the disc space of a patient;
wherein the first endcap and second endcap are formed of the at least one rigid material dispensed by the at least one dispensing nozzle.

10. The additive-manufacturing system of claim 9, further comprising a provisioning component for affecting a rate of flow of printing material and a type of printing material through the at least one dispensing nozzle,
wherein the controller is further configured to control the provisioning component on the basis of the in-situ-printing plan and the in-situ material selection plan.

11. The additive-manufacturing system of claim 9, wherein the controller is further configured to control forming the at least one motion-sparing implant from a plurality of different printing materials chosen from the at least one rigid material and the at least one pliable material.

12. The additive-manufacturing system of claim 9, further comprising a mixing component configured to selectively mix materials chosen from the at least one rigid material, the at least one pliable material, and at least one adhesive material.

13. The additive-manufacturing system of claim 9, wherein the computer-executable instructions are further configured to, when executed by the processor, cause the controller to form a lattice structure having a repeating pattern of cells from the at least one rigid material and fill the cells with the at least one pliable material.

* * * * *